United States Patent

Antane et al.

Patent Number: 5,780,505
Date of Patent: Jul. 14, 1998

[54] SUBSTITUTED N-ARYLMETHYLAMINO DERIVATIVES OF CYCLOBUTENE-3, 4-DIONES

[75] Inventors: Madelene M. Antane, Lawrenceville, N.J.; David R. Herbst, Wayne, Pa.; Geraldine R. McFarlane, Monmouth Junction; Eric G. Gundersen, Plainsboro, both of N.J.; Bradford H. Hirth, Littleton, Mass.; Dominick A. Quagliato, Bridgewater, N.J.; Russell F. Graceffa, Plainsboro, N.J.; John A. Butera, Clarksburg, N.J.

[73] Assignee: American Home Products Corporation, Madison, N.J.

[21] Appl. No.: 889,166

[22] Filed: Jul. 7, 1997

Related U.S. Application Data

[60] Provisional application No. 60/022,188, Jul. 17, 1996.

[51] Int. Cl.⁶ ............................................. A61K 31/275
[52] U.S. Cl. ............................. 514/522; 514/524; 514/538; 514/534; 514/604; 514/605; 514/617; 514/625; 514/627; 514/629; 514/655; 560/27; 564/84; 564/90; 564/99; 564/207; 564/180; 564/184; 564/218; 564/345; 564/384
[58] Field of Search ........................... 558/413, 414; 564/84, 90, 99, 207, 180, 184, 218, 345, 384; 560/27; 514/524, 522, 538, 534, 604, 605, 617, 625, 627, 629, 655

[56] References Cited

U.S. PATENT DOCUMENTS

| | | |
|---|---|---|
| 4,390,701 | 6/1983 | Algieri et al. |
| 4,673,747 | 6/1987 | Nobara et al. |
| 5,240,946 | 8/1993 | Kinney et al. |
| 5,354,746 | 10/1994 | Chandrakumar et al. |
| 5,397,790 | 3/1995 | Butera et al. |
| 5,401,753 | 3/1995 | Butera et al. |
| 5,403,853 | 4/1995 | Butera et al. |
| 5,403,854 | 4/1995 | Butera et al. |
| 5,464,867 | 11/1995 | Antane et al. |
| 5,466,712 | 11/1995 | Butera et al. |
| 5,506,252 | 4/1996 | Butera et al. |
| 5,512,585 | 4/1996 | Autane et al. |
| 5,530,025 | 6/1996 | Antane et al. |
| 5,532,245 | 7/1996 | Butera et al. |
| 5,536,731 | 7/1996 | Antane et al. |
| 5,536,741 | 7/1996 | Antane et al. |

FOREIGN PATENT DOCUMENTS

| | | |
|---|---|---|
| 426379 | 10/1990 | European Pat. Off. |
| 496561 | 1/1992 | European Pat. Off. |
| 645385 | 3/1995 | European Pat. Off. |

OTHER PUBLICATIONS

Tietze et al., Chem. Berg., 1991, 124, 1215–1221.
Tietze et al., Bioconjugate Chem., 1991, 2, 148–153.
Ehrhardt et al., Chem. Ber., 1977, 110, 2506–2523.
Neuse et al., Liebigs Ann. Chem., 1973, 619–632.
Takeno et al. Public Patent Disclosure Bull. No. 6–92915 (Japan).
Reid et al., Liebigs Ann. Chem., 1981, 402.
Kinney et al., J. Med. Chem., 1992, 35, 4720.

Primary Examiner—James H. Reamer
Attorney, Agent, or Firm—Rebecca R. Barrett

[57] ABSTRACT

The compounds of the formula:

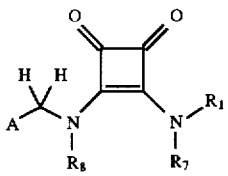

(I)

wherein $R_1$ is straight chain alkyl, branched chain alkyl, cycloalkyl, hydroxyalkyl, fluoroalkyl or polyfluoroalkyl; $R_7$ and $R_8$ are, independently, hydrogen or an acyl substituent selected from the group consisting of formyl, alkanoyl, alkenoyl, alkoxycarbonyl, alkylsulfonyl, aroyl, arylalkenoyl, arylsulfonyl, arylalkanoyl or arylalkylsulfonyl; A is a phenyl group with either two or three substituents of the following formula:

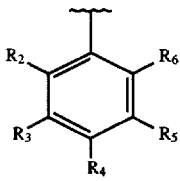

wherein the positions of substitution are $R_2,R_3$-, $R_2,R_4$-, $R_2,R_5$-, $R_2,R_6$-, $R_3,R_4$-, $R_3,R_5$-, and $R_2,R_4,R_6$- and $R_2$ is methyl, ethyl, fluoro, chloro, methoxy or trifluoromethyl; $R_3$ is methyl, ethyl, fluoro, chloro, methoxy or trifluoromethyl; $R_4$ is methyl, fluoro, bromo, methoxy or cyano; $R_5$ is methyl, fluoro, chloro, methoxy, cyano or trifluoromethyl; $R_6$ is methyl, fluoro, chloro, or methoxy; or a pharmaceutically acceptable salt thereof, relax smooth muscles.

35 Claims, No Drawings

SUBSTITUTED N-ARYLMETHYLAMINO DERIVATIVES OF CYCLOBUTENE-3, 4-DIONES

BACKGROUND OF INVENTION

This application claims the benefit of U.S. application No. 60/022,118, filed Jul. 17, 1996 and is a continuation-in-part of that prior application which is incorporated by reference herein in its entirety.

The present invention relates to novel 1,2-diamino derivatives of cyclobutene 3,4-diones having pharmacological activity, to a process for their preparation, to pharmaceutical compositions containing them and to their use, via potassium channel modulation, in the treatment of disorders associated with smooth muscle contraction. Such disorders include, but are not limited to, urinary incontinence, hypertension, asthma, premature labor, irritable bowel syndrome, congestive heart failure, angina and cerebral vascular disease.

Stemp et al. (EP-426379) disclose a class of amino substituted cyclobutenedione derivatives of chromans described as having blood pressure lowering activity and bronchodilatory activity . Takeno et al. (Public Patent Disclosure Bulletin No. 6-92915) report a series of diaminocyclobuten-3,4-diones. Our own efforts in this area have been disclosed in the following U.S. Pat. Nos.: 5,354, 763, 5,397,790, 5,401,753, 5,403,853, 5,403,854, 5,506, 252; 5,466,712, 5,532,245; 5,464,867, 5,512,585, 5,530, 025, 5,536,731, 5,536,741. Several series of 1-amino-2-phenylalkylamino-cyclobutene-3,4-diones are reported as H-2 receptor antagonists by Algieri et al. in U.S. Pat. No. 4,390,701. Several related 1-amino-2-phenoxyalkylamino derivatives are disclosed by Nohara et al. in U.S. Pat. No. 4,673,747. Additionally, U.S. Pat. No. 5,240,946 and EP-496561 disclose diaminocyclobuten-3,4-diones useful as NMDA antagonists.

The syntheses of variously substituted 1,2-diamino-cyclobutene-3,4-diones are described in the following publications: Tietze et al., Chem Ber. 1991, 124, 1215; Tietze et al., Bioconjugate Chem. 1991, 2, 148; Ehrhardt et al., Chem. Ber. 1977, 110, 2506, Neuse et al., Liebigs Ann. Chem. 1973, 619, Ried et al., Liebigs Ann. Chem. 1973, 619, Kinney et al., J. Med. Chem. 1992, 35, 4702.

DESCRIPTION OF THE INVENTION

In accordance with the present invention there is provided a group of compounds of the formula (I):

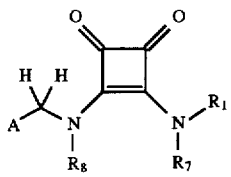

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_7$ and $R_8$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_8$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms $R_7$ must be hydrogen.

A is a phenyl group with either two or three substituents of the following formula:

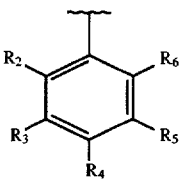

wherein:

the positions of substitution are $R_2,R_3$-, $R_2$, $R_4$-, $R_2,R_5$-, $R_2,R_6$-, $R_3,R_4$, $R_3,R_5$-, and $R_2$, $R_4,R_6$- and $R_2$ is methyl, ethyl, fluoro, chloro, methoxy or trifluoromethyl;

$R_3$ is methyl, ethyl, fluoro, chloro, methoxy or trifluoromethyl;

$R_4$ is methyl, fluoro, bromo, methoxy or cyano;

$R_5$ is methyl, fluoro, chloro, methoxy, cyano or trifluoromethyl;

$R_6$ is methyl, fluoro, chloro, or methoxy; or a pharmaceutically acceptable salt thereof.

A preferred aspect of this invention involves those compounds which have demonstrated activity at a concentration of less than 100 μM in the relaxation of smooth muscle represented by formula (I) wherein:

$R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_8$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_7$ must be hydrogen.

A is a phenyl group with either two or three substituents of the following formula:

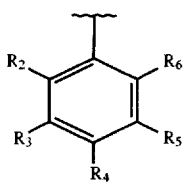

wherein:

the positions of substitution are $R_2,R_3$-, $R_2,R_4$-, $R_2,R$-, $R_2,R_6$-, $R_3,R_4$-, $R_3,R_5$-, and $R_2,R_4,R_6$-positions and $R_2$ is methyl, ethyl or chloro;

$R_3$ is methyl, ethyl or chloro;

$R_4$ is methyl, bromo or cyano;

$R_5$ is cyano, chloro, or methyl;

$R_6$ is methyl or choro; or a pharmaceutically acceptable salt thereof.

For the same reason, those compounds are favored when the substitutional variations at position combinations $R_2,R_4$- and $R_3,R_4$- are as follows:

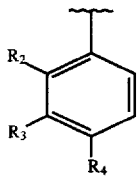

where $R_2$ is trifluoromethyl, fluoro or chloro;

$R_3$ is fluoro or chloro;

$R_4$ is fluoro; or a pharmaceutically acceptable salt thereof.

In addition, those compounds are favored when the substitutional variations at position combinations $R_2,R_5$-, $R_2,R_6$-, and $R_3,R_5$- are as follows:

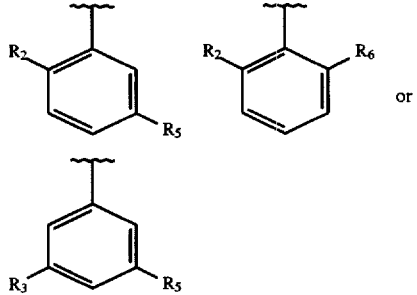

where $R_2$ is methyl, fluoro or chloro;

$R_3$ is fluoro;

$R_5$ is fluoro or trifluoromethyl;

$R_6$ is fluoro; or a pharmaceutically acceptable salt thereof.

A more preferred aspect of this invention involves those compounds that exhibit activity at a concentration less than 30 μM in the relaxation of smooth muscle, represented by the formula (I) wherein:

$R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxy-carbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_2,R_3$-, $R_2,R_4$- and $R_2,R_4,R_6$-:

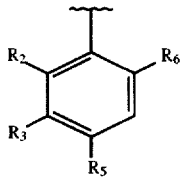

where $R_2$ is methyl, ethyl or chloro;

$R_3$ is methyl or chloro;

$R_4$ is methyl, bromo or cyano;

$R_6$ is methyl or chloro; or a pharmaceutically acceptable salt thereof.

Similarly, the potency of compounds at below 30 μM categorizes the following compounds as preferred with substitution combinations at $R_3,R_4$-, $R_3,R_5$-, $R_2,R_5$-, and $R_2,R_6$-positions.

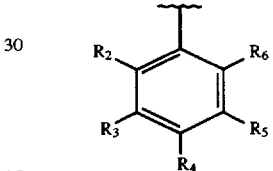

where the groups representing $R_2$, $R_3$, $R_4$, $R_5$, and $R_6$, independently, are selected from the following:

$R_2$ is methyl or chloro;

$R_3$ is methyl, ethyl or chloro;

$R_4$ is cyano or methyl;

$R_5$ is cyano, chloro, or methyl;

$R_6$ is methyl or chloro; or a pharmaceutically acceptable salt thereof.

Likewise, as mentioned supra, preferred substitution combinations in the $R_2,R_4$- and $R_3,R_4$-positions, where $R_2$, $R_3$ and $R_4$, independently, are selected from the following:

$R_2$ is trifluoromethyl, fluoro or chloro;

$R_3$ is fluoro or chloro;

$R_4$ is fluoro; or a pharmaceutically acceptable salt thereof.

And, as mentioned supra, preferred substitution combinations in the $R_2,R_5$-, $R_2,R_6$- and $R_3,R_5$-positions, where $R_2$, $R_3$, $R_5$, $R_6$, independently, are selected from the following:

$R_2$ is methyl, fluoro or chloro;

$R_3$ is fluoro;

$R_5$ is fluoro or trifluoromethyl;

$R_6$ is fluoro; or a pharmaceutically acceptable salt thereof.

The most preferred aspect of this invention resides in those compounds with activity at concentrations less than 10 μM in relaxation of smooth muscle, represented by formula (I) wherein:

$R_1$ is α,α-substituted branched chain alkyl of 4 to 10 carbon atoms;

$R_7$ is hydrogen;

$R_8$ is hydrogen, or alkanoyl of 2 to 4 carbon atoms;

A is a phenyl group with either two or three substituents of the following formula:

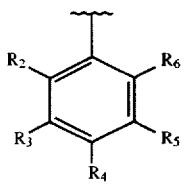

wherein
the preferred substitution combinations are selected from the following:

| $R_2$ | Me | Me | Cl | Me | Me | Et | Cl | Me | Cl | Cl | Cl |
|---|---|---|---|---|---|---|---|---|---|---|---|
| $R_3$ | Me | Cl | Cl | H | H | H | H | H | H | H | H |
| $R_4$ | H | H | H | Me | CN | CN | CN | H | H | H | H |
| $R_5$ | H | H | H | H | H | H | H | Me | Cl | H | H |
| $R_6$ | H | H | H | H | H | H | H | H | H | Cl | Me |
| $R_2$ | Me | H | H | H | H | H | H | Me | Me | Me | Me |
| $R_3$ | H | Cl | Et | Me | Cl | Me | Me | H | H | H | H |
| $R_4$ | H | CN | CN | Me | H | H | H | Me | Me | Br | CN |
| $R_5$ | H | H | H | H | Cl | Me | CN | H | H | H | H |
| $R_6$ | Me | H | H | H | H | H | H | Me | Cl | Me | Cl |
| $R_2$ | $CF_3$ | F | Cl | Cl | F | F | F | H | H | H | H |
| $R_3$ | H | H | H | H | H | H | H | Cl | F | F | F |
| $R_4$ | F | F | F | H | H | H | H | F | F | H | H |
| $R_5$ | H | H | H | F | F | $CF_3$ | H | H | H | F | $CF_3$ |
| $R_6$ | H | H | H | H | H | H | F | H | H | H | H | or a pharmaceutically acceptable salt thereof.

It is understood that the definition of the compounds of formula (I), when $R_1$, $R_7$, or $R_8$ contain asymmetric carbons, encompass all possible stereoisomers and mixtures thereof which possess the activity discussed below. In particular, the compounds of formula I include racemic mixtures and any optical isomers which possess the indicated activity. Optical isomers may be obtained in pure form by standard separation techniques. α,α-Substituted branched chain alkyl refers to an alkyl chain in which the carbon adjacent to the nitrogen is tertiary, such as t-butyl, 1,1-dimethylpropyl, 3-methyl-3-pentyl, 3-ethyl-3-pentyl, 2,3-dimethyl-2-butyl, 2,3,3-trimethyl-2-butyl, 2,3-dimethyl-3-pentyl, and any similarly substituted branched alkyl chain. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids.

The present invention also provides a process for the preparation of a compound of formula (I). More particularly, the compounds of formula (I) may be prepared by reacting a compound of formula (II):

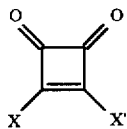
(II)

wherein X and X' is a suitably designed leaving group such as methoxy, ethoxy, butoxy, isopropoxy, halogeno or a similar leaving group, with a compound of formula (III):

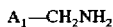
(III)

wherein $A_1$ is A, as defined hereinbefore or a group of atoms convertible thereto, followed by treatment with a compound of formula (IV):

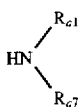
(IV)

wherein $R_{a1}$ and $R_{a7}$ are $R_1$ and $R_7$, respectively, as defined hereinbefore or a group of atoms convertible thereto, in a solvent such as ethanol, acetonitrile, or the appropriate amine (IV) at elevated temperatures or room temperature. Dichloromethane can be used as a cosolvent. The order of addition of the compound of formula (III) and the compound of formula (IV) to the compound of formula (II) may be reversed. Furthermore reaction of the sodium, potassium, or lithium salt of compound of formula (II) where X is $NHCH_2$-A attached to the cyclobutene group through the nitrogen where A is defined above, and X' is $NHR_1$ attached to the cyclobutene group through the nitrogen where $R_1$ is as defined above, with the appropriate anhydride in tetrahydrofuran and/or N,N-dimethylformamide allows for the attachment of $R_8$. Reaction of sodium, potassium, or lithium salt of compound of formula (II), where X is a leaving group such as methoxy, ethoxy, butoxy, isopropoxy, or similar leaving group and X' is $NHR_1$ attached to the cyclobutene group through the nitrogen where $R_1$ is as defined above, with the appropriate anhydride in dichloromethane, tetrahydrofuran and/or N,N-dimethylformamide or any other suitable solvent, followed by treatment with a compound of formula (III) as defined above in a solvent such as acetonitrile at room temperature allows for the attachment of the acyl groups represented by $R_7$.

Alternatively, reaction of sodium, potassium or lithium salt of a compound of formula (II), where X is a leaving group such as methoxy, ethoxy, butoxy, isopropoxy, or similar leaving group; and X' is $NHCH_2$-A attached to the cyclobutene group through the nitrogen where A is as defined above, with the appropriate dialkyl dicarbonate in the presence of triethylamine, 4-dimethylaminopyridine and a suitable solvent such as dichloromethane, tetrahydrofuran and/or N,N-dimethylformamide, followed by treatment with a compound of formula (IV) as defined above in a solvent such as acetonitrile or tetrahydrofuran at room temperature allows for the attachment of the alkoxycarbonyl groups represented by $R_8$.

As mentioned previously, the compounds of formula (I) have been found to relax smooth muscle. They are active at concentrations below 300 μM. They are useful in the treatment of disorders associated with smooth muscle contraction, disorders involving excessive smooth muscle contraction of the urinary tract (such as incontinence), or of the gastrointestinal tract (such as irritable bowel syndrome), asthma, and hair loss. Furthermore, the compounds of formula (I) are active as potassium channel activators which render them useful for treatment of peripheral vascular disease, hypertension, congestive heart failure, stroke, anxiety, cerebral anoxia and other neurodegenerative disorders.

The present invention also provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patient suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

The present invention further provides a compound of the invention for use as an active therapeutic substance. Compounds of formula (I) are of particular use in the induction of smooth muscle relaxation.

The present invention further provides a method of treating smooth muscle disorders in mammals including man, which comprises administering to the afflicted mammal an effective amount of a compound or a pharmaceutical composition of the invention.

The following examples are presented to illustrate rather than limit the scope of the invention.

EXAMPLE 1

3-Butoxy-4-tert-butylamino-cyclobut-3-ene-1,2-dione

A solution of 3,4-dibutoxy-3-cyclobutene-1,2-dione (11.31 g, 50 mmol) and tert-butylamine (3.66 g, 50 mmol) in tetrahydrofuran (80 mL) was stirred at room temperature for 71 hours. The solvent was removed and a solution of the residue in chloroform was washed with water and dried (anhydrous $Na_2SO_4$). Removal of the solvent and chromatographic (gravity, chloroform/hexane) purification of the amber liquid residue on a column of neutral, activity III silica (350 g) provided 9.83 g (87%) of a white solid product, mp 67.0°–68.5° C. Two recrystallizations of an aliquot (800 mg) afforded 551 mg of the title compound as a white solid: mp 68°–69° C. (softens 67° C.); $^1$H NMR (DMSO-$d_6$) δ8.75 and 8.59 (two br s, 1H, rotamers), 4.66 (br m, 2H), 1.72 (m, 2H), 1.40 (m, 2H), 1.31 (m, 9H), 0.91 (t, 3H) ppm. IR (KBr): 3140, 1780, 1700 cm$^{-1}$; MS (m/z) 225 (M$^+$).

Elemental analysis for $C_{12}H_{19}NO_3$ Calc'd: C, 63.98; H, 8.50; N, 6.22. Found: C, 64.13; H, 8.60; N, 6.24.

EXAMPLE 2

4-[(2-tert-Butylamino-3,4-dioxo-cyclobut-1-enylamino)-methyl]-3-chloro-benzonitrile Step 1) Preparation of 2-Chloro-4-cyanobenzyl bromide A mixture of 3-chloro-4-methylbenzonitrile (22.74 g, 150 mmol), N-bromosuccinimide (32.04 g, 180 mmol) and 2,2'-azobis-2-methylpropionitrile (2.46 g, 15 mmol) in carbon tetrachloride (120 mL) was carefully warmed to reflux temperature whereupon a moderate exotherm occurred and refluxing proceeded for approximately 10 minutes without external heating. Heating was then resumed and refluxing continued for 26 hours. The hot reaction mixture was suction filtered and the insolubles were rinsed with carbon tetrachloride (3×25 mL). The combined carbon tetrachloride fractions were washed with water and dried (anhydrous $Na_2SO_4$). Removal of solvent gave a yellow mush which was crystallized from hexane (charcoal). The product again was recrystallized from hexane to yield 20.44 g (59%) of the white bromide: mp 80.5°–83.5° C. (softens 71.5° C.) (lit. mp 85°–85.5° C. (B. Gogolimska, Acta Pol. Pharm., 25 (4), 391 (1968) [C.A., 70, 87493e (1969)].)); $^1$H NMR (DMSO-$d_6$) δ8.10 (d, 1H), 7.82 (m, 2H), 4.69 (s, 2H) ppm. IR (KBr): 2220 cm$^{-1}$.

Step 2) Preparation of N-(2-chloro-4-cyanobenzyl) phthalimide

A mixture of product from Example 2, Step 1 (20.29 g, 88.0 mmol) and potassium phthalimide (17.92 g, 96.8 mmol) in N,N-dimethylformamide (200 mL) was stirred as the reaction temperature rose to approximately 36° C. during approximately 5 minutes with formation of a tan suspension. The temperature then receded and stirring was continued for 2 hours. After removal of solvent, the residue was triturated thoroughly with water and dried.

The buff solid product was treated with approximately 500 mL boiling ethyl acetate, gravity filtered to remove a small amount of white insoluble material, heated to boiling, treated with charcoal and filtered. Concentration and cooling of the filtrate afforded (after drying) 20.26 g (78%) of the title compound phthalimide as a white solid: mp 172.5°–173.0° C. (softens 170.5° C.); $^1$H NMR (DMSO-$d_6$) δ8.10 (d, 1H), 7.90 (m, 4H), 7.75 (dd, 1H), 7.52 (d, 1H), 4.88 (s, 2H) ppm. IR (KBr): 2220, 1770, 1715 cm$^{-1}$.

Step 3) Preparation of 2-chloro-4-cyanobenzylamine

A mechanically stirred suspension of product from Example 2, Step 2 (18.99 g, 64 mmol) in absolute ethanol (150 mL) was treated with hydrazine hydrate (6.41 g, 128 mmol) and the mixture was stirred and refluxed for 1 hour and then was allowed to stand at room temperature for approximately 16.5 hours. With stirring 2N HCl (90 mL) was added slowly, and after 10 minutes of further stirring the mixture was filtered. The insolubles were triturated thoroughly with ethanol and then with water. The combined filtrate and triturates were freed of solvent and the residue in approximately 250 mL ice-$H_2O$ was basified with 2.5N NaOH (90 mL). The mass was extracted thoroughly with chloroform and the extracts were washed with water, with brine and dried (anhydrous $Na_2SO_4$). Removal of solvent gave a cream-colored solid which was recrystallized from hexane to provide 6.85 g (64%) of a white amine: mp 85.0°–87.0° C. (soften 82.5° C.); $^1$H NMR (DMSO-$d_6$) δ7.96 (d, 1H), 7.82 (dd, 1H), 7.77 (m, 1H), 3.82 (s, 2H), 2.12 (br m, 2H) ppm. IR (KBr): 3380, 3320, 2230 cm$^{-1}$.

Step 4) 4-[(2-tert-Butylamino-3,4-dioxo-cyclobut-1-enylamino)-methyl]-3-chloro-benzonitrile Tetrahydrofuran (50 mL), 3-butoxy-4-tert-butylamino-cyclobut-3-ene-1,2-dione (6.76 g, 30 mmol, Example 1) and the product of Example 2, Step 3 (5.00 g, 30 mmol) were refluxed for 6 hours and allowed to stand at room temperature for 16 hours. Following removal of solvent from the reaction mixture, the residue was triturated thoroughly with diethyl ether and dried to give a buff solid. This material in approximately 1.4 L of boiling acetone, was filtered to remove a small amount of white solid. The hot filtrate was treated with charcoal, filtered, concentrated and cooled to afford 6.521 g of a cream-colored solid. Two additional recrystallizations of this material from acetone gave 4.779 g (50%) of the title compound as a white solid: mp 243.5°–245.° C. (softens 241.0° C.); $^1$H NMR (DMSO-$d_6$)

δ8.10 (d, 1H), 7.88 (dd, 1H), 7.82 (m, 1H), 7.66 (s, br, 1H), 7.61 (d, 1H), 4.88 (d, 2H), 1.34 (s, 9H) ppm. IR (KBr): 3320, 3230, 2240, 1780, 1665 cm$^{-1}$; MS (m/z) 317/319 (M$^+$). HPLC indicates a major component (99.6%).

Elemental analysis for $C_{16}H_{16}ClN_3O_2$ Calc'd: C, 60.48; N, 5.08; N, 13.22; Cl, 11.16. Found: C, 60.08; H, 4.97; N, 13.06; Cl, 10.82, 10.71.

The following is another method for the preparation of 4-[(2-tert-butylamino-3,4-dioxo-cyclobut-1-enylamino)-methyl]-3-chloro-benzonitrile. To a solution of 4-[(2-butoxy-3,4-dioxo-cyclobut-1-enylamino)-methyl]-3-chlorobenzonitrile (0.638 g, 2 mmol, Example 92) in tetrahydrofuran (8 mL) was added t-butylamine (0.146 g, 2 mmol). After stirring overnight at room temperature, the mixture was refluxed for 6.5 hours. Additional t-butylamine (0.146g, 2 mmol) was added and the mixture was stirred overnight at room temperature. Removal of solvent gave a yellow solid that was recrystallized from acetone to afford 0.217 g of the title compound: mp 244°–246° C. (dec.). MS (m/z) 317/319 (M$^+$). Based on NMR DMSO-d$_6$ spectral comparison, this product is the same as that described in Example 2, Step 4.

EXAMPLE 3

3-Butoxy-4-(1,1-dimethyl-propylamino)-cyclobut-3-ene-1,2-dione

A solution of 3,4-dibutoxy-3-cyclobutene-1,2-dione (4.53 g, 20 mmol) and 1,1-dimethylpropylamine (1.74 g, 20 mmol) in tetrahydrofuran (20 mL) was stirred at room temperature for approximately 19.5 hours. The solvent was removed and the residue was chromatographed (gravity, chloroform/hexane) on neutral, activity III silica (150 g). The white solid isolated from the appropriate eluates was recrystallized from hexane to give 4.105 g (86%) of a white product: mp 56.5°–57.5° C. (softens 55.5° C.).

One gram of this material was recrystallized twice from hexane to provide 0.794 g of the title compound as a white solid: mp 56°–57° C. (softens 55° C.); $^1$H NMR (DMSO-d$_6$) δ8.63 and 8.48 (two br s, 1H, rotamers), 4.67 (br m, 2H), 1.67 (br m, 4H), 1.39 (m, 2H), 1.26 (br m, 6H), 0.91 (t, 3H), 0.78 (t, 3H) ppm. IR (KBr): 3170, 1790, 1700 cm$^{-1}$; MS (m/z) 239 (M$^+$).

Elemental analysis for $C_{13}H_{21}NO_3$ Calc'd: C, 65.24; H, 8.85; N, 5.85 Found: C, 65.12; H, 8.90; N, 5.77

EXAMPLE 4

3-(2,6-Dichloro-benzylamino)-4-(1,1-dimethyl-propylamino)-cyclobut-3-ene-1,2-dione Step 1) Preparation of N-(2,6-dichlorobenzyl)phthalimide To α,2,6-trichlorotoluene (19.55 g, 100 mmol) in N,N-dimethylformamide (130 mL) was added with stirring potassium phthalimide (18.54 g, 100 mmol) and stirring was continued for 22 hours. Solvent was removed and the residue was dissolved in chloroform (400 mL)/water (350 mL). The chloroform extract was washed with water, with brine and dried (anhydrous Na$_2$SO$_4$). Removal of solvent and drying gave 28.98 g of a white solid. Recrystallization of the crude product from ethyl acetate provided 24.63 g (81%) of white phthalimide: mp 147°–150° C. (The preparation of this compound is given in U.S. Pat. No. 4,146,647 (Mar. 27, 1979, to Laboratoire L. Lafon) but no physical constants are reported); $^1$H NMR (DMSO-d$_6$): δ7.83 (s, 4H), 7.47 (m, 2H), 7.35 (m, 1H), 5.00 (s, 2H) ppm. IR (KBr): 1770, 1715 cm$^{-1}$; MS (m/z) 306/308/310 ([M+H]$^+$).

Step 2) Preparation of 2,6-dichlorobenzylamine hydrochloride

The phthalimide from Example 4, Step 1 (6.13 g, 20 mmol), ethanol (90 mL) and hydrazine monohydrate (3.00 g, 60 mmol) were refluxed for 1.25 hours. After cooling to room temperature the mixture was filtered and the insolubles were rinsed with ethanol (3×50 mL). The combined filtrate and rinsings were freed of solvent and the residue was shaken with ethyl acetate and 10% aqueous sodium carbonate solution. The ethyl acetate fraction was washed successively with 10% w/v aqueous sodium carbonate solution, brine and dried (anhydrous Na$_2$SO$_4$). Removal of solvent and drying of the residue gave 3.17 g of a pale yellow oil.

Dissolution of 3.15 g of the preceding oil in diethyl ether and addition of isopropanolic hydrogen chloride gave a white solid that was collected, rinsed with diethyl ether and dried. The crude hydrochloride was recrystallized from isopropanol in the presence of several drops of isopropanolic hydrogen chloride, rinsed with diethyl ether and dried to afford 2.70 g (64% overall) of white hydrochloride: mp 260°–261° C. (dec.) (lit. mp 237°–238° C. (S. Angyal et al., J. Chem. Soc., 1949, 2704; The preparation of this compound is given in U.S. Pat. No. 4,146,647 (Mar. 27, 1979, to Laboratoire L. Lafon) but no physical constants are reported)); $^1$H NMR (DMSO-d$_6$): δ8.54 (s, br, 3H), 7.58 (m, 2H), 7.48 (m, 1H), 4.23 (s, 2H) ppm. IR (KBr): 2860 cm$^{-1}$; MS (m/z) 174/176/178 (M$^+$).

Step 3) 3-(2,6-Dichloro-benzylamino)-4-(1,1-dimethyl-propylamino)-cyclobut-3-ene-1,2-dione To 2,6-dichlorobenzylamine hydrochloride of Example 4, Step 2 (1.06 g 5.0 mmol) in tetrahydrofuran (10 mL) was added triethyl amine (0.505 g, 5.0 mmol) followed by 3-butoxy-4-(1,1-dimethyl-propylamino)-cyclobut-3-ene-1,2-dione (1.20 g, 5.0 mmol, Example 3) and stirring was continued at room temperature for approximately 16 hours. The reaction mixture was freed of solvent and the residue was triturated successively with water and with diethyl ether, and then dried. The resulting light yellow solid was recrystallized from acetonitrile three times to provide 0.755 g (44%) of the title compound as a white solid: mp 239°–241° C. (dec); $^1$H NMR (DMSO-d$_6$): δ7.57 (m, 1H), 7.55 (m, 1H), 7.52 (br m, 1H),m 7.43 (m, 1H), 7.30 (s, br, 1H), 5.07 (d, 2H), 1.65 (q, 2H), 1.28 (s, 6H), 0.80 (t, 3H) ppm. IR (KBr): 3250, 1785, 1660 cm$^{-1}$; MS (m/z) 340/342/344 (M$^+$). HPLC indicates a major component (99.7%).

Elemental analysis for $C_{16}H_{18}Cl_2N_2O_2$ Calc'd: C, 56.32; H, 5.32; N, 8.21. Found: C, 56.17; H, 5.27; N, 8.17.

EXAMPLE 5

3-Butoxy-4-(1,2,2-trimethyl-propylamino)-cyclobut-3-ene-1,2-dione

Tetrahydrofuran (15 mL), 3,4-dibutoxy-3-cyclobutene-1,2-dione (2.26 g, 10 mmol) and 2-amino-3,3-dimethylbutane (1.01 g, 10 mmol) were stirred together for approximately 65 hours at room temperature. The waxy solid remaining after removal of solvent was dissolved in chloroform (15 mL) and chromatographed (flash, ethyl acetate/hexane) on silica. The appropriate fractions were freed of solvent to yield 2.41 g (95%) of cream-colored waxy solid: mp 90°–9° C.° (softens 85° C.).

Two recrystallization of 1.1 g of this material from hexane provided 0.833 g of the title compound as a white solid: mp 90°–93C° (softens 88C°); $^1$H NMR: (DMSO-d$_6$): δ8.73 and 8.50 (two br d, 1H, rotamers), 4.64 (m, 2H), 3.92 and 3.41 (two m, 1H, rotamers), 1.71 (m, 2H), 1.38 (m, 2H), 1.11 (m, 3H), 0.91 (t, 3H), 0.84 (m, 9H). IR(KBr): 3135, 1800, 1690 cm$^{-1}$; MS (m/z) 253 (M$^+$).

Elemental analysis for C$_{14}$H$_{23}$NO$_3$ Calc'd: C, 66.37; H, 9.15; N, 5.53. Found: C, 66.47; H, 9.20; N, 5.50.

EXAMPLE 6

3-Chloro-4-{|3,4-dioxo-2-(1,2,2-trimethyl-propylamino)-cyclobut-1-enylamino|-methyl}-benzonitrile A solution of 3-butoxy-4-(1,2,2-trimethyl-propylamino) cyclobut-3-ene-1,2-dione (1.27 g, 5.0 mmol, Example 5), 2-chloro-4-cyanobenzylamine (0.833 g, 5.0 mmol, Example 2, Step 3) and tetrahydrofuran (8 mL) was stirred at room temperature for 23 hours, refluxed for 4 hours and allowed to stand at room temperature for approximately 62 hours. The mixture was freed of solvent and the residue was triturated with diethyl ether and dried. The resulting white solid (1.096 g) was recrystallized three times from methanol to yield 771 mg (45%) of the title compound as a faintly pink solid: mp 250.0°–251.5° C. (softens 248.0° C.); $^1$H NMR (DMSO-d$_6$) δ8.10 (d, 1H), 7.88 (m, 1H), 7.70 (br m, 1H), 7.61 (d, 1H), 7.37 (br m, 1H), 4.88 (m, 1H), 3.91 (br m, 1H), 1.11 (d, 3H), 0.86 (s, 9H) ppm IR (KBr): 3200, 2230, 1790, 1635 cm$^{-1}$; MS (m/z) 345/347 (M$^+$). HPLC indicates a major component (98.7%).

Elemental analysis for C$_{18}$H$_{10}$ClN$_3$O$_2$ Calc'd: C, 62.52; H, 5.83; N, 12.15. Found: C, 62.57; H, 5.74; N, 12.00.

EXAMPLE 7

3-{|2-(1,1-Dimethyl-propylamino)-3,4-dioxo-cyclobut-1-enylamino|-methyl}-5-methyl-benzonitrile Step 1) Preparation of 3-cyano-5-methylbenzyl bromide N-Bromosuccinimide (3.56 g, 20 mmol), 3,5-dimethylbenzonitrile (2.62 g, 20 mmol) and 2,2'-azobis-2-methylpropionitrile (0.328 g, 2.0 mmol) in carbon tetrachloride (25 mL) were refluxed for 23 hours. The hot mixture was filtered (twice) and the filtrate was freed of solvent to give a yellow oil that was chromatographed (flash, silica, ethyl acetate/hexane). From the appropriate eluates 2.587 g of a white solid were isolated. Recrystallization of this material from methanol provided 1.51 g (36%) of bromide: mp 82°–85° C. (softens 75° C.) (lit mp 92°–93° C. (T. H. Fisher et al , J. Org. Chem., 55, 1040 (1990)); 87°–88° C. (E. Gryszkiewicz-Trochimowski et al. Bull. Soc. Chem. Fr., 1948, 593 [C.A., 42, 7240h (1948)])); $^1$H NMR (DMSO-d$_6$) δ7.72 (s, 1H), 7.61 (s, 1H), 4.68 (s, 2H), 2.33 (s, 3H) ppm. IR (KBr): 2230 cm$^{-1}$; MS (m/z) 209/211 (M$^+$).

Step 2) Preparation of N-(3-cyano-5-methyl)phthalimide

A mixture of 3-cyano-5-methylbenzyl bromide from Example 7, Step 1 (15.79 g, 75.16 mmol) and potassium phthalimide (15.31 g, 82.68 mmol) in N,N-dimethylformamide (150 mL) was vigorously stirred for 4 hours. The reaction mixture was freed of solvent and the residue was dissolved in chloroform (200 mL)/water (400 mL). The chloroform fraction was separated and the aqueous phase was extracted with chloroform (2×75 mL). The combined chloroform fractions were washed with water, with brine and dried (anhydrous Na$_2$SO$_4$). Removal of solvent gave 20.2 g of crude product which was recrystallized from acetonitrile to yield 13.12 g (63%) of white phthalimide: mp 180°–184° C.; $^1$H NMR (DMSO-d$_6$) δ7.87 (br m, 4H), 7.60 (s, br, 1H), 7.56 (s, br, 1H), 7.47 (s, br, 1H) 4.78 (s, 2H), 2.32 (s, 3H) ppm. IR (KBr): 2240, 1770, 1720 cm$^{-1}$; MS (m/z) 276 (M$^+$).

Step 3) Preparation of 3-cyano-5-methylbenzylamine

A suspension of N-(3-cyano-5-methyl)phthalimide from Example7, Step 2 (1.11 g, 4.0 mmol), hydrazine monohydrate (0.24 g, 4.8 mmol) and ethanol (20 mL) was refluxed for 3 hours, diluted with water (60 mL) and the mixture was acidified with conc. HCl (0.5 mL). After brief stirring, the mixture was filtered and the filtrate was basified with conc. sodium hydroxide and extracted with ethyl acetate (3×25 mL). The combined extracts were washed with water, with brine and dried (anhydrous Na$_2$SO$_4$). Removal of solvent gave 0.386 g (66%) of amine as a clear oil: $^1$H NMR (DMSO-d$_6$) δ7.57 (m, 1H), 7.47 (m, 2H), 3.70 (s, 2H), 2.33 (s, 3H) ppm. IR (KBr): 3380, 3300, 2220 cm$^{-1}$; MS (m/z) 146 (M$^+$).

Step 4) 3-(|2-(1,1-Dimethyl-propylamino)-3,4-dioxo-cyclobut-1-enylamino|-methyl)-5-methyl-benzonitrile A solution of 3-butoxy-4-(1,1-dimethyl-propylamino) cyclobut-3-ene-1,2-dione (1.44 g, 6.0 mmol, Example 3) and 3-cyano-5-methylbenzylamine from Example 7, Step 3 (6.0 mmol) and tetrahydrofuran (15 mL) were stirred at room temperature for approximately 20 hours. An additional 7 mL of tetrahydrofuran were added and stirring continued for an additional 48 hours. The solvent was removed and the residue was recrystallized twice from methanol to provide 1.251 g (67%) of the title compound as a white solid: mp 231°–133° C. (softens 229° C.); $^1$H NMR (DMSO-d$_6$) δ7.78 (m, 1H), 7.62 (m, 2H), 7.51 (s, 1H), 7.41 (s, br, 1H), 4.74 (d, 2H), 2.35 (s, 3H), 1.67 (m, 2H), 1.30 (s, 6H), 0.82 (m, 3H) ppm. IR (KBr): 3290, 2240, 1780, 1670 cm$^{-1}$; MS (m/z) 311 (M$^+$). HPLC indicates a major component (99.7%).

Elemental analysis for C$_{18}$H$_{21}$N$_3$O$_2$ Calc'd: C, 69.43; H, 6.80; N, 13.49. Found: C, 69.25; H, 6.72; N, 13.60.

EXAMPLE 8

3-tert-Butylamino-4-(2,4-dimethyl-benzylamino)-cyclobut-3-ene-1,2-dione

A solution of 3-butoxy-4-tert-butylamino-cyclobut-3-ene-1,2-dione (1.13 g, 5.0 mmol, Example 1) and 2,4-dimethylbenzylamine (0.68 g, 5.0 mmol, a mixture of 2,4- and 2,6-dimethylbenzylamine isomers) in tetrahydrofuran (10 mL) was stirred at room temperature for approximately 16 hours. Removal of solvent, thorough trituration of the residue with diethyl ether and drying provided 1.07 g of crude product. Three recrystallizations of this material from acetonitrile gave 0.67 g (47%) of the title compound as a white solid: mp 228°–229° C.; $^1$H NMR (DMSO-d$_6$) δ7.57 (m, 1H), 7.48 (s, br, 1H), 7.17 (d, 1H), 7.03 (s, br, 1H), 7.00 (d, br, 1H), 4.69 (d, 2H), 2.27 (s, 3H), 2.24 (s, 3H), 1.35 (s, 9H) ppm. IR (KBr): 3310, 1785, 1670 cm$^{-1}$; MS (m/z) 286 (M$^+$). HPLC indicates a major component (98.7%).

Elemental analysis for C$_{17}$H$_{22}$N$_2$O$_2$. Calc'd: C, 71.30; H, 7.74; N, 9.78. Found: C, 71.29; H, 7.79; N, 9.82.

EXAMPLE 9

3-tert-Butylamino-4-(2,4,6-trimethyl-benzylamino)-cyclobut-3-ene-1,2-dione

Step 1) Preparation of N-(2,4,6-trimethylbenzyl) phthalimide

N,N-Dimethylformamide (50 mL), 2,4,6-trimethylbenzyl chloride (5.06 g, 30 mmol) and potassium phthalimide (6.11 g, 33 mmol) were combined with stirring. After an initial reaction temperature rise from approximately 25° C. to 34° C. during 15 minutes, the temperature receded to room temperature and stirring was continued for approximately 17 hours. Solvent then was removed and the residue was thoroughly triturated with water and dried. The 7.62 g crude product was recrystallized from ethyl acetate and dried to yield 5.62 g of white phthalimide: mp 204.5°–206.5° C. (softens 196.5° C.) (lit. mp 209.5°–210° C. (R. T. Fuson and J. J. Denton, J. Am. Chem. Soc., 63, 654 (1941))); $^1$H NMR (DMSO-d$_6$) δ7.82 (s, 4H), 6.78 (s, 2H), 4.72 (s, 2H), 2.28 (s, 6H), 2.17 (s, 3H). IR(KBr): 1765, 1710 cm$^{-1}$; MS (m/z) 279 (M$^+$).

Step 2) Preparation of 2,4,6-trimethylbenzylamine hydrochloride

The phthalimide from Example 9, Step 1 (5.52 g, 19.8 mmol), ethanol (90 mL) and hydrazine monohydrate (2.97 g, 59.4 mmol) were refluxed for 1.3 hours. After cooling to room temperature the mixture was filtered and the insolubles were rinsed with ethanol (3×50 mL). The combined filtrate and rinsings were freed of solvent and the residue was dissolved in ethyl acetate. The solution was washed with 10% w/v aq. Na$_2$CO$_3$ solution, with water and dried. Removal of solvent gave 2.68 g of yellow oil.

Dissolution of the preceding oil in diethyl ether, filtration and addition of isopropanolic hydrogen chloride afforded a solid that was collected, rinsed with diethyl ether and dried. The crude salt was recrystallized from absolute ethanol in the presence of several drops of isopropanolic hydrogen chloride, rinsed with diethyl ether and dried to provide 1.25 g (37%) of off-white hydrochloride: mp>320° C. (dec) (lit. mp 315° C. (dec) (R. C. Fuson and J. J. Denton, J. Am. Chem. Soc., 63, 654 (1941)); $^1$H NMR (DMSO-d$_6$) δ8.05 (s, br, 3H), 6.90 (s, 2H), 2.34 (s, 6H), 2.21 (s, 3H) ppm. IR (KBr): 2900 br, 1880 br cm$^{-1}$; MS (m/z) 149 (M$^+$).

Step 3) 3-tert-Butylamino-4-(2,4,6-trimethyl-benzylamino)-cyclobut-3-ene-1,2-dione Tetrahydrofuran (10 mL), 2,4,6-trimethylbenzylamine hydrochloride from Example 9, Step 2 (0.610 g, 3.29 mmol), triethylamine (0.334 g, 3.3 mmol) and 3-butoxy-4-tert-butylamino-cyclobut-3-ene-1,2-dione (0.741 g, 3.29 mmol, Example 1) were stirred together at room temperature for approximately 65 hours. After removal of solvent, the residue was triturated with water, with diethyl ether and dried to provide 0.633 g white solid. Three recrystallizations of this material from acetonitrile gave 0.256 g (26%) of title compound as a cream-colored solid: mp 309°–310° C. dec; $^1$H NMR (DMSO-d$_6$) δ7.37 (s, 1H), 7.24 (m, 1H), 6.89 (s, 2H), 4.74 (d, 2H), 2.30 (s, 6H), 2.21 (s, 3H), 134 (s, 9H) ppm. IR (KBr): 3280, 1780, 1660 cm$^{-1}$; MS (m/z) 300 (M$^+$). HPLC indicates a major component (99%).

Elemental analysis for C$_{18}$H$_{24}$N$_2$O$_2$ Calc'd: C, 71.97; H, 8.05; N, 9.33. Found: C, 72.05; H, 8.02; N, 9.32.

EXAMPLE 10

3-tert-Butylamino-4-(2,6-dichloro-benzylamino)-cyclobut-3-ene-1,2-dione

To 2,6-dichlorobenzylamine hydrochloride from Example 5, Step 2 (1.06 g, 5.0 mmol) in tetrahydrofuran (10 mL) was added triethylamine (0.505 g, 5.0 mmol) followed by 3-butoxy-4-tert-butylamino-cyclobut-3-ene-1,2-dione (1.13 g, 5.0 mmol, Example 1) and stirring was continued for approximately 16 hours. The reaction mixture was freed of solvent and the residue was triturated with water, with diethyl ether and dried. The white solid thus isolated was crystallized twice from methanol to give 0.623 g (38%) of the title compound as a white solid: mp 265°–6° C. dec (softens 263° C.); $^1$H NMR (DMSO-d$_6$) δ7.55 (d, 2H), 7.49 (br m, 1H), 7.42 (m, 2H), 5.05 (d, 2H), 1.34 (s, 9H) ppm. IR (KBr): 3185, 1785, 1660 cm$^{-1}$; MS (m/z) 326/328/330 (M$^+$). HPLC indicates a major component (99.9%).

Elemental analysis for C$_{15}$H$_{16}$N$_2$O$_2$ Calc'd: C, 55.06; H, 4.93; N, 8.56. Found: C, 54.70; H, 4.84; N, 8.45.

EXAMPLE 11

3-Butoxy-4-(1-ethyl-propylamino)-cyclobut-3-ene-1,2-dione

A solution of 3,4-dibutoxy-3-cyclobut-3-ene-1,2-dione (2.26 g, 10 mmol) and 1-ethylpropylamine (0.872 g, 10 mmol) in tetrahydrofuran (8 mL) was stirred at room temperature for 2.5 hours. The residue remaining after removal of solvent was dissolved in chloroform and the solution was washed with water and dried (anhydrous Na$_2$SO$_4$). Removal of solvent gave a waxy solid that was chromatographed (flash, chloroform/hexane) on silica. The solid isolated from the appropriate fractions was recrystallized twice from hexane to yield 0.896 g (37%) of the title compound: mp 65°–66° C.; $^1$H NMR (DMSO-d$_6$) δ8.63 and 8.40 (two d, 1H, rotamers), 4.64 (m, 2H), 3.74 and 3.30 (two m, 1H, rotamers), 1.71 (m, 2H), 1.54 (m, 2H), 1.39 (m, 4H), 0.90 (m, 3H), 0.82 (m, 6H) ppm. IR (KBr): 3140, 1790, 1720 cm$^{-1}$; MS (m/z) 239 (M$^+$).

Elemental analysis for C$_{13}$H$_{21}$NO$_3$ Calc'd: C, 65.25; H, 8.85; N, 5.85. Found: C, 65.37; H, 9.07; N, 5.87.

EXAMPLE 12

3-{[3,4-Dioxo-2-(1,2,2-trimethyl-propylamino)-cyclobut-1-enylamino]-methyl}-5-methyl-benzonitrile This compound was prepared in a manner similar to Example 7, Step 4 using appropriate starting materials to afford 3-{[3,4-dioxo-2-(1,2,2-trimethyl-propylamino)-cyclobut-1-enylamino]-methyl}-5-methyl-benzonitrile 0.03 ethanolate as a white solid: mp 244°–247° C.

EXAMPLE 13

3-{[2-(1-Ethyl-propylamino)-3,4-dioxo-cyclobut-1-enylamino]-methyl}-5-methyl-benzonitrile This compound was prepared in a manner similar to Example 7, Step 4 using appropriate starting materials to afford 3-{[2-(1-ethyl-propylamino)-3,4-dioxo-cyclobut-1-enylamino]-methyl}-5-methyl-benzonitrile as a white solid: mp 248°–250° C.

EXAMPLE 14

3-(3,4-Dimethoxy-benzylamino)-4-(1-ethyl-propylamino)-cyclobut-3-ene-1,2-dione

This compound was prepared in a manner similar to Example 8 using appropriate starting materials to afford 3-(3,4-dimethoxy-benzylamino)-4-(1-ethyl-propylamino)-cyclobut-3-ene-1,2-dione as a white solid: mp 223°–224° C.

EXAMPLE 15

3-tert-Butylamino-4-(2,4,6-trimethoxy-benzylamino)-cyclobut-3-ene-1,2-dione

This compound was prepared in a manner similar to Example 4, Step 3 using appropriate starting materials and pyridine as the solvent to afford 3-tert-butylamino-4-(2,4,6- trimethoxy-benzylamino)-cyclobut-3-ene-1,2-dione as a white solid: mp partially melts and resolidifies at 225.5°–227.0° C., then decomposes 294°–306° C.

EXAMPLE 16

3-[(2-tert-Butylamino-3,4-dioxo-cyclobut-1-enylamino)-methyl]-5-methyl-benzonitrile This compound was prepared in a manner similar to Example 2 using appropriate starting materials to afford 3-[(2-tert-butylamino-3,4-dioxo-cyclobut-1-enylamino)-methyl]-5-methyl-benzonitrile as a white solid: mp 253°–255° C.

EXAMPLE 17

3-tert-Butylamino-4-(2,4-dimethoxy-benzylamino)-cyclobut-3-ene-1,2-dione

This compound was prepared in a manner similar to Example 4, Step 3 using appropriate starting materials to afford 3-tert-butylamino-4-(2,4-dimethoxy-benzylamino)-cyclobut-3-ene-1,2-dione as a white solid: mp 225°–226° C.

EXAMPLE 18

3-tert-Butylamino-4-(2,4-difluoro-benzylamino)-cyclobut-3-ene-1,2-dione

This compound was prepared in a manner similar to Example 8 using appropriate starting materials to afford 3-tert-butylamino-4-(2,4-difluoro-benzylamino)-cyclobut-3-ene-1,2-dione as a white solid: mp 227°–228° C. (dec).

EXAMPLE 19

3-tert-Butylamino-4-(2,6-difluoro-benzylamino)-cyclobut-3-ene-1,2-dione

This compound was prepared in a manner similar to Example 8 using appropriate starting materials to afford 3-tert-butylamino-4-(2,6-difluoro-benzylamino)-cyclobut-3-ene-1,2-dione as an off-white solid: mp 269° C. (dec).

EXAMPLE 20

3-tert-Butylamino-4-(2,3-dimethoxy-benzylamino)-cyclobut-3-ene-1,2-dione

This compound was prepared in a manner similar to Example 8 using appropriate starting materials to afford 3-tert-butylamino-4-(2,3-dimethoxy-benzylamino)-cyclobut-3-ene-1,2-dione as a solid: mp 215°–216° C. (dec).

EXAMPLE 21

3-tert-Butylamino-4-(2,5-difluoro-benzylamino)-cyclobut-3-ene-1,2-dione

This compound was prepared in a manner similar to Example 8 using appropriate starting materials to afford 3-tert-butylamino-4-(2,5-difluoro-benzylamino)-cyclobut-3-ene-1,2-dione as an off-white solid: mp 273°–274° C. (dec).

EXAMPLE 22

3-tert-Butylamino-4-(3,5-dimethoxy-benzylamino)-cyclobut-3-ene-1,2-dione

This compound was prepared in a manner similar to Example 8 using appropriate starting materials to afford 3-tert-butylamino-4-(3,5-dimethoxy-benzylamino)-cyclobut-3-ene-1,2-dione as a white solid: mp 222°–223° C.

EXAMPLE 23

3-tert-Butylamino-4-(2,3-dimethyl-benzylamino)-cyclobut-3-ene-1,2-dione

This compound was prepared in a manner similar to Example 80 using appropriate starting materials to afford 3-tert-butylamino-4-(2,3-dimethyl-benzylamino)-cyclobut-3-ene-1,2-dione as a white solid: mp 237°–239° C.

EXAMPLE 24

4-[(2-Butylamino-3,4-dioxo-cyclobut-1-enylamino)-methyl]-3-ethyl-benzonitrile

Step 1) Preparation of 3-ethoxy-4-(2-ethyl-4-cyano-benzylamino)-cyclobut-3-ene-1,2-dione 4-Cyano-2-ethylbenzaldehyde oxime (0.17 g, 0.98 mmol, synthesized by the procedure of Jolad et al., Org. Syntheses, Coll. Vol. V, 139 (1973), Example 29, Step 1) was dissolved in glacial acetic acid. Zinc powder (0.13 g, 2.0 mmol) was added. The slurry was heated at 50° C. for 30 minutes, then a second portion of zinc powder (0.13 g, 2.0 mmol) was added. The slurry was heated at 60° C. for 30 minutes. The reaction mixture was cooled, diluted with ethanol (30 mL), and filtered through Celite®. The filtrate was treated with 3,4-diethoxy-3-cyclobutene-1,2-dione (0.14 mL, 0.95 mmol), and the solution was left under vacuum (100 mm) overnight. The resulting reddish residue was combined with the crude product from another similar reaction in which 4-cyano-2-ethylbenzaldehyde oxime (0.17 g, 0.98 mmol) was used. The combined residues were triturated six times with 5% ethyl acetate in hexane to give 0.47 g (90%) of a pale pink solid: $^1$H NMR (DMSO-$d_6$) δ9.28 and 9.05 (two br m, 1H, rotamers), 7.68 (m, 2H), 7.43 (m, 1H), 4.90–4.50 (m, 4H), 2.67 (m, 2H), 1.37 and 1.25 (two t, 3H, rotamers), 1.16 (t, 3H) ppm. MS (m/z) 284 (M$^+$).

Step 2) 4-[(2-Butylamino-3,4-dioxo-cyclobut-1-enylamino)-methyl]-3-ethyl-benzonitrile The product of Example 24, Step 1 (0.18 g, 0.63 mmol) and n-butylamine (0.15 mL, 1.55 mmol) was placed in absolute ethanol (3.5 mL) and dichloromethane (2 mL). The clear solution was allowed to stand at room temperature for 24 hours. The resulting solid slurry was filtered, rinsed with hexane:ethyl acetate (1:1), and dried to give 0.10 g (50%) of the title compound as a white solid: $^1$H NMR (DMSO-$d_6$) δ7.70 (overlapping m and br m, 3H), 7.45 (d, 1H), 7.38 (br m, 1H), 4.83 (d, 2H), 3.90 (q, 2H), 2.69 (q, 2H), 1.49 (quintet, 2H), 1.29 (sextet, 2H), 1.17 (t, 3H), 0.88 (t, 3H) ppm. IR (KBr): 3280,2950, 2200, 1800, 1650 cm$^{-1}$; MS (m/z) 311 (M$^+$).

Elemental analysis for $C_{18}H_{21}N_3O_2$ Calc'd: C, 69.43; H, 6.80; N, 13.49. Found: C, 68.67; H, 6.72; N, 13.33.

EXAMPLE 25

3-Ethyl-4-[(2-isopropylamino-3,4-dioxo-cyclobut-1-enylamino)-methyl-benzonitrile This compound was prepared according to the procedure described in Example 24, Step 2. From the product of Example 24, Step 1 (0.18 g, 0.63 mmol) and isopropylamine (0.13 mL, 1.55 mmol) in absolute ethanol (3.5 mL) and dichloromethane (2 mL) there was obtained 0.17 g (89%) of the title compound as a pale orange solid: $^1$H NMR (DMSO-d$_6$) δ7.70 (m, 2H), 7.65 (br m, 1H), 7.46 (d, 1H), 7.41 (br m, 1H), 4.83 (d, 2H), 3.30 (m, 1H), 2.69 (q, 2H), 1.19 (overlapping d and t, 9H) ppm. IR (KBr): 3280, 2960, 2200, 1800, 1650 cm$^{-1}$; MS (m/z) 297 (M$^+$).

Elemental analysis for C$_{17}$H$_{19}$N$_3$O$_2$ Calc'd: C, 68.67; H, 6.44; N, 14.13. Found: C, 68.47; H, 6.43; N, 14.21.

EXAMPLE 26

3-Ethyl-4-{[(2-(1-ethyl-propylamino)-3,4-dioxo-cyclobut-1-enylamino]-methyl}-benzonitrile This compound was prepared according to the procedure described in Example 24, Step 2. From the product of Example 24, Step 1 (0.18 g, 0.63 mmol) and 1-ethylpropylamine (0.18 mL, 1.55 mmol) in absolute ethanol (3.5 mL) and dichloromethane (2 mL) there was obtained 0.16 g (76%) of the title compound as an off-white solid: $^1$H NMR (DMSO-d$_6$) δ7.70 (m, 2H), 7.59 (br m, 1H), 7.46 (d, 1H), 7.23 (br d, 1H), 4.85 (d, 2H), 3.30 (m, 1H), 2.69 (q, 2H), 1.56 (m, 2H), 1.43 (m, 2H), 1.17 (t, 3H), 0.85 (t, 6H) ppm. IR (KBr): 3180, 2970, 2210, 1795, 1650 cm$^{-1}$; MS (m/z) 325 (M$^+$).

Elemental analysis for C$_{19}$H$_{23}$N$_3$O$_2$ Calc'd: C, 70.13; H, 7.12; N, 12.91. Found: C, 69.66; H, 7.06; N, 12.89.

EXAMPLE 27

4-[(2-tert-Butylamino-3,4-dioxo-cyclobut-1-enylamino)-methyl]-3-ethyl-benzonitrile The product of Example 24, Step 1 (0.45 g, 1.58 mmol) in t-butylamine (8 mL) was heated at 80° C. under argon for 2 hours. The reaction mixture was cooled to room temperature and concentrated under reduced pressure. The residue was triturated with ethyl acetate to give 0.25 g of a solid, which was further purified by chromatography (silica gel, 3% methanol in dichloromethane. The resulting solid was suspended in 10% ethyl acetate in hexane, filtered, and rinsed with 10% ethyl acetate in hexane to yield 0.18 g (37%) of a pale yellow solid: mp 224°–228° C. (softens 229° C.); $^1$H NMR (DMSO-d$_6$) δ7.76–7.69 (m, 3H), 7.57 (br s, 1H), 7.47 (br d, 1H), 4.85 (d, 2H), 2.69 (q, 2H), 1.36 (s, 9H), 1.18 (t, 3H) ppm. IR (KBr): 3210, 2980, 2210, 1790, 1650 cm$^{-1}$; MS (m/z) 311 (M$^+$).

Elemental analysis for C$_{18}$H$_{21}$N$_3$O$_2$ Calc'd: C, 69.43; H, 6.80; N, 13.49. Found: C, 69.12; H, 6.79; N, 13.69.

EXAMPLE 28

4-{[3,4-Dioxo-2-(1,2,2-trimethyl-propylamino)-cyclobut-1-enylamino]-methyl}-3-ethyl-benzonitrile Step 1) Preparation of 4-Cyano-2-ethylbenzaldehyde oxime 4-Cyano-2-ethylbenzaldehyde oxime was prepared by the procedure of Jolad et al., *Org. Syntheses, Coll.* Vol. V, 139 (1973). A mixture of paraformaldehyde (2.8 g, 93 mmol) and hydroxylamine hydrochloride (6 g, 86 mmol) in water (39 mL) was heated in a 500 mL 3-necked flask. When a clear, colorless solution was obtained, sodium acetate trihydrate (11.8 g, 87 mmol) was added. The solution was heated for 15 minutes, then cooled in an ice-salt bath to approximately 5°–10° C. To this solution was added copper sulfate (0.97 g, 6.08 mmol), sodium sulfite (0.23 g, 1.82 mmol) and sodium acetate trihydrate (37 g, 272 mmol) in water (42 mL). The resulting green solution was cooled to an internal temperature of approximately 5°–10° C. A diazonium salt solution of 4-amino-3-ethylbenzonitrile was previously prepared as follows: A mixture of 4-amino-3-ethylbenzonitrile (8.32 g, 57 mmol), concentrated hydrochloric acid (13.2 mL), ice (23 g), and water (11.6 mL) was cooled in an ice-salt bath. While maintaining the internal temperature below 10° C., a solution of sodium nitrite (4.2 g, 61 mmol) in water (5.8 mL) was added dropwise. The resulting slurry was stirred at 5°–10° C. for an additional 15 minutes. Then a solution of sodium acetate trihydrate (5.1 g, 37 mmol) in water (8.1 mL) was added. This solution of the diazonium salt was siphoned under the surface of the 10% formaldoxime solution. The reaction mixture was stirred vigorously and allowed to slowly warm to room temperature as the ice-salt bath melted. After 2 hours the reaction mixture was diluted with brine (100 mL), extracted with dichloromethane (2×400 mL), and dried (Na$_2$SO$_4$). Purification by chromatography (silica gel, hexane:ethyl acetate (7:1)) gave 2.97 g (30%) of a solid: $^1$H NMR (DMSO-d$_6$) δ11.80 (s, 1H), 8.45 (s, 1H), 8.00–7.60 (m, 3H), 2.90 (m, 2H), 1.20 (m, 3H).

Step 2) Preparation of 4-Cyano-2-ethylbenzyl alcohol

The product from Example 28, Step 1(2.9 g, 17 mmol) and 2N hydrochloric acid (142 mL) was stirred at room temperature. Acetone (100 mL) was added to produce a homogeneous solution. After 5 days the reaction mixture was diluted with ethyl acetate (500 mL) and solid sodium chloride was added until the aqueous layer was saturated. After stirring at room temperature for 1 hour, the ethyl acetate layer was separated and dried (Na$_2$SO$_4$). Concentration under reduced pressure yielded 7 g of a solid which was chromatographed (silica gel) with hexane, then hexane:ethyl acetate (8:1). This gave 2.0 g (75%) of 4-cyano-2-ethylbenzaldehyde, which was used without further purification. 4-Cyano-2-ethylbenzaldehyde (2.0 g, 13 mmol) in methanol (63 mL) was cooled to 0° C. Solid sodium borohydride (0.48 g, 13 mmol) was added. The reaction mixture was stirred at 0° C. for 1 hour. A second portion of sodium borohydride (0.48 g, 13 mmol) was added, and the reaction mixture was stirred at 0° C. for 40 minutes. A third portion of sodium borohydride (0.48 g, 13 mmol) was added and the reaction mixture was stirred at 0° C. for 20 minutes. The ice bath was then removed and the reaction mixture was stirred at room temperature for 1 hour. Water (28 mL) was then added and the reaction mixture was stirred at room temperature for 24 hours. The solution was then diluted with ethyl acetate (100 mL) and divided into two portions, which were each extracted with ethyl acetate (300 mL) and brine (40 mL). The combined ethyl acetate layers were concentrated under reduced pressure and the resulting residue was chromatographed (silica gel) with hexane:ethyl acetate (7:1), then hexane:ethyl acetate (3:1) to yield 1.53 g (75%) of a solid: $^1$H NMR (DMSO-d$_6$) δ7.70–7.50 (m, 3H), 5.39 (br m, 1H), 4.59 (s, 2H), 2.60 (q, 2H), 1.18 (t, 3H).

Step 3) Preparation of N-(4-Cyano-2-ethylbenzyl) phthalimide

The product of Example 28, Step 2 (0.95 g, 5.9 mmol), phthalimide (1.05 g, 7.1 mmol), triphenylphosphine (1.85 g, 7.1 mmol), and tetrahydrofuran (39 mL) were mixed and cooled to 0° C. in an ice bath. Diethylazodicarboxylate (1.09 mL, 6.9 mmol) was added dropwise. The reaction mixture was allowed to warm to room temperature as the ice bath melted. After 24 hours the reaction mixture was concentrated under reduced pressure and the resulting residue was chromatographed (silica gel) with hexane:ethyl acetate (5:1), hexane:ethyl actate (3:1), then hexane:ethyl acetate (2:1) to yield 1.85 g (108%) of a solid: $^1$H NMR (DMSO-d$_6$) δ8.00–7.80 (m, 4H), 7.70 (s, 1H), 7.59 (d, 1H), 7.30 (d, 1H), 4.86 (s, 2H), 2.81 (q, 2H), 1.22 (t, 3H).

Step 4) Preparation of 4-Cyano-2-ethylbenzylamine

The product of Example 28, Step 3 (1.73 g, 6.0 mmol), 35% hydrazine (1.07 mL, 12 mmol), and absolute ethanol (105 mL) were mixed and heated at 65° C. under argon for 3 hours. Then the reaction was heated at 85° C. for 5 hours. The reaction mixture was concentrated under reduced pressure, resuspended in absolute ethanol (35 mL), filtered and rinsed with absolute ethanol (2×30 mL). Concentration under reduced pressure yielded a solid, which was suspended in ethyl acetate (100 mL) and filtered. The filtrate was concentrated under reduced pressure to give 0.77 g (81%) of a wet solid: $^1$H NMR (CDCl$_3$) δ7.50 (m, 3H), 3.94 (s, 2H), 2.70 (m, 2H), 1.43 (br m, 2H), 1.21 (t, 3H).

Step 5) 4-{[3,4-Dioxo-2-(1,2,2-trimethyl-propylamino)-cyclobut-1-enylamino]-methyl}-3-ethyl-benzonitrile The product of Example 28, Step 4 (0.21 g, 1.3 mmol) was placed in absolute ethanol (5.5 mL). (R)-3-Ethoxy-4-(1,2,2-trimethyl-propylamino)-cyclobut-3-ene-1,2-dione (0.3 g, 1.3 mmol, prepared in a manner similar to Example 5 from 3,4-diethoxy-3-cyclobutene-1,2-dione and (R)-2-amino-3,3-dimethylbutane in ethanol) was added, followed by dichloromethane (5 mL). The clear solution was stirred at room temperature for 5 days. The reaction mixture was concentrated under reduced pressure and the resulting solid was chromatographed (silica gel) with 1% methanol in dichloromethane, then 3% methanol in dichloromethane. This gave 0.19 g (43%) of the (R) isomer of the title compound as a light tan solid: mp 208°–212° C.; $[\alpha]^{25}_D$=+13.440 (8.6 mg/mL, DMSO) $^1$H NMR (DMSO-d$_6$) δ7.71 (m, 2H), 7.60 (br m, 1H), 7.48 (br d, 1H), 7.27 (br d, 1H), 4.85 (m, 2H), 3.90 (m, 1H), 2.69 (q, 2H), 1.17 (t, 3H), 1.10 (d, 3H), 0.86 (s, 9H) ppm. IR (KBr): 3200, 2970, 2230, 1800, 1650 cm$^{-1}$; MS (m/z) 339 (M$^+$).

Elemental analysis for C12H$_{25}$N$_3$O$_2$ Calc'd: C, 70.77; H, 7.42; N, 12.38. Found: C, 70.05; H, 7.29; N, 12.13.

EXAMPLE 29

3-(2-Chloro-6-methyl-benzylamino)-4-(1,2,2-trimethyl-propylamino)-cyclobut-3-ene-1,2-dione This compound was prepared according to the procedure described in Example 28, Step 5. From (R)-3-ethoxy-4-(1,2,2-trimethyl-propylamino)-cyclobut-3-ene-1,2-dione (0.3 g, 1.3 mmol) and 2-chloro-6-methylbenzylamine (0.2 g, 1.3 mmol) in absolute ethanol (2.7 mL) there was obtained a solid, which was diluted with acetonitrile (4 mL), filtered, rinsed with acetonitrile (2×2 mL), and dried. This gave 0.42 g (96%) of the (R) isomer of the title compound as a white solid: mp 288°–292° C. (dec); $[\alpha]^{25}_D$=+24.92° (10.0 mg/mL, DMSO); $^1$H NMR (DMSO-d$_6$) δ7.40–7.20 (m, 4H), 7.15 (br d, 1H), 4.93 (m, 2H), 3.90 (m, 1H), 2.40 (s, 3H), 1.09 (d, 3H), 0.85 (s, 9H) ppm. IR (KBr): 3150, 2980, 2230, 1800, 1650 cm$^{-1}$; MS (m/z) 334/336 (M$^+$).

Elemental analysis for C$_{18}$H$_{23}$ClN$_2$O$_2$ Calc'd: C, 64.57; H, 6.92; N, 8.37. Found: C, 64.28; H, 6.76; N, 8.16.

EXAMPLE 30

(R)-3-Chloro-4-{[3,4-dioxo-2-(1,2,2-trimethyl-propylamino)-cyclobut-1-enylamino]-methyl}-benzonitrile 2-Chloro-4-cyano-benzylamine (0.30 g, 1.80 mmol, Example 2, Step 3) and (R)-3-ethoxy-4-(1,2,2-trimethyl-propylamino)-cyclobut-3-ene-1,2-dione (0.406 g, 1.80 mmol) were stirred in ethanol (10 mL) at 70° C. for 18 hours. The reaction was cooled and diluted with diethyl ether. Filtration afforded 0.49 g (79%) of (R)-3-chloro-4-{[3,4-dioxo-2-(1,2,2-trimethyl-propylamino)-cyclobut-1-enylamino]-methyl}-benzonitrile which was collected as a white solid: mp 237°–241° C.; $[\alpha]^{25}_D$=+27.30° (10.99 mg/mL, DMSO); $^1$H NMR (DMSO-d$_6$) δ8.10 (d, 1H), 7.89 (dd, 1H), 7.68 (m, 1H), 7.69 (d, 1H), 7.36 (br d, 1H), 4.87 (m, 2H), 3.90 (m, 1H), 1.12 (d, 3H), 0.86 (s, 9H) ppm. IR (KBr): 3100, 2950, 2250, 1800 cm$^{-1}$. MS (m/z) 345/347 (M$^+$).

Elemental analysis for C$_{18}$H$_{20}$ClN$_3$O$_2$ Calc'd: C, 62.52; H, 5.83; N, 12.15. Found: C, 62.78; H, 6.17; N, 11.90.

EXAMPLE 31

3-tert-Butylamino-4-(2-chloro-6-methyl-benzylamino)-cyclobut-3-ene-1,2-dione

A mixture of 3,4-diethoxy-3-cyclobutene-1,2-dione (5 g, 29 mmol) and 2-chloro-6-methylbenzylamine (4.57 g, 29 mmol) in absolute ethanol (147 mL) was allowed to stand at room temperature for 4 days. The reaction mixture was concentrated under reduced pressure and suspended in dichloromethane (200 mL). The slurry was stirred at room temperature for 18 hours, filtered, rinsed with dichloromethane, and concentrated under reduced pressure to give 6.42 g (78%) of a solid. A portion of this solid, 3-(2-chloro-6-methyl-benzylamino)-4-ethoxy-cyclobut-3-ene-1,2-dione, (0.4 g, 1.43 mmol) was placed in t-butylamine (4 mL) and dichloromethane (4 mL) and allowed to stand at room temperature for 6 days. The solid was filtered, rinsed several times with ethyl acetate, and dried. This gave 0.31 g (71%) of the title compound as a white solid: mp 254°–257° C.; $^1$H NMR (DMSO-d$_6$) δ7.46 (br s, 1H), 7.42 (br t, 1H), 7.38–7.22 (m, 3H), 4.93 (d, 2H), 2.40 (s, 3H), 1.34 (s, 9H) ppm. IR (KBr): 3200, 2960, 1790, 1650 cm$^{-1}$; MS (m/z) 306/308 (M$^+$).

Elemental analysis for C$_{16}$H$_{19}$ClN$_2$O$_2$ Calc'd: C, 62.64; H, 6.24; N, 9.13. Found: C, 62.40; H, 6.29; N, 9.08.

EXAMPLE 32

3-(2-chloro-6-methyl-benzylamino)-4-(1,1-dimethyl-propylamino)-cyclobut-3-ene-1,2-dione 3-(2-Chloro-6-methyl-benzylamino)-4-ethoxy-cyclobut-3-ene-1,2-dione (0.4 g, 1.43 mmol) was placed in 1,1-dimethylpropylamine (5 mL) and dichloromethane (2 mL) and refluxed for 14 hours. The solvent was removed under reduced pressure to give 0.37 g of a solid, which was placed in isopropanol, filtered and concentrated under reduced pressure. This was repeated with ethyl acetate. The residue was placed in 5% ethanol in water, filtered, rinsed with water, then ethyl acetate, and dried in vacuo (0.4 mm, 70° C.) to yield 0.27 g (59%) of the title compound as a solid: mp 224°–226° C. (softens 192° C.); $^1$H NMR (DMSO-d$_6$) δ7.44 (br t, 1H), 7.39–7.22 (m, 4H), 4.93 (d, 2H), 2.40 (s, 3H), 1.65 (q, 2H), 1.28 (s, 6H), 0.80 (t, 3H) ppm. IR (KBr): 3200, 2970, 1800, 1650 cm$^{-1}$; MS (m/z) 320/322 (M$^+$).

Elemental analysis for C$_{17}$H$_{21}$ClN$_2$O$_2$ Calc'd: C, 63.65; H, 6.60; N, 8.73. Found: C, 63.37; H, 6.56; N, 8.58.

EXAMPLE 33

3-Chloro-4-{[2-(1,1-dimethyl-propylamino)-3,4-dioxo-cyclobut-1-enylamino]-methyl}-5-methyl-benzonitrile Step 1) Preparation of 3-(2-chloro-4-cyano-6-methyl-benzylamino)-4-ethoxy-cyclobut-3-ene-1,2-dione To 2-chloro-4-cyano-6-methylbenzaldehyde oxime (1.2 g, 6.2 mmol, prepared according to the procedure of Example 28, Step 1) in glacial acetic acid (12.3 mL) was added zinc powder (1.6 g, 24 mmol). The slurry was heated to boiling. When the bubbling subsided, a second portion of zinc powder (1.6 g, 24 mmol) was added and the slurry was heated to boiling. When the reaction had cooled to room temperature, it was diluted with absolute ethanol, filtered through Celite®, rinsed with absolute ethanol, and concentrated under reduced pressure. The resulting residue was mixed with 3,4-diethoxy-3-cyclobutene-1,2-dione (0.91 mL, 6.2 mmol) and absolute ethanol, then allowed to stand at room temperature for 18 hours. The solid precipitate was filtered and rinsed with ethyl acetate to give 0.51 g of a solid. This solid was dissolved in dichloromethane, filtered, rinsed with dichloromethane, and the filtrate concentrated under reduced pressure to give 0.19 g of a solid: $^1$H NMR (DMSO-$d_6$) $\delta$8.97 and 8.74(br m, 1H, rotamers), 7.92 (s, 1H), 7.74 (s, 1H), 4.93 (br m, 1H), 4.78–4.60 (br m, 3H), 2.43 (s, 3H), 1.36 (br m, 3H) ppm. MS (m/z) 304/306 (M$^+$).

Step 2) 3-Chloro-4-{[2-(1,1-dimethyl-propylamino)-3,4-dioxo-cyclobut-1-enylamino]-methyl}-5-methyl-benzonitrile The product from Example 33, Step 1 (0.24 g, 0.79 mmol) was placed in 1,1-dimethylpropylamine (5 mL) and dichloromethane (3 mL) and refluxed for 8 hours. The solvent was removed under reduced pressure to give a solid, which was placed in ethyl acetate, filtered, rinsed with ethyl acetate, and dried in vacuo (0.4 mm, 70° C.). This gave 0.17 g (62%) of the title compound as a solid: mp 258°–262° C. (dec); $^1$H NMR (DMSO-$d_6$) $\delta$7.99 (s, 1H), 7.78 (s, 1H), 7.51 (br t, 1H), 7.35 (s, 1H), 4.98 (d, 2H), 2.46 (s, 3H), 1.66 (q, 2H), 1.29 (s, 6H), 0.80 (t, 3H) ppm. IR (KBr): 3200, 2980, 2200, 1800, 1650 cm$^{-1}$; MS (m/z) 345/347 (M$^+$).

Elemental analysis for $C_{18}H_{20}ClN_3O_2$ Calc'd: C, 62.52; H, 5.83; N, 12.15. Found: C, 62.74; H, 5.87; N, 12.15.

EXAMPLE 34

3-Chloro-4-{[3,4-dioxo-2-(1,2,2-trimethyl-propylamino)-cyclobut-1-enylamino]-methyl}-5-methyl-benzonitrile The product from Example 33, Step 1 (0.19 g, 0.62 mmol) and (R)-2-amino-3,3-dimethylbutane (4.7 mL of a 0.2M solution in absolute ethanol, 0.94 mmol) was stirred at room temperature for 2 days. The slurry was filtered, rinsed with acetonitrile (3×3 mL), and dried. This gave 0.15 g (67%) of the (R) isomer of the title compound as a white solid: mp >300° C.; $^1$H NMR (DMSO-$d_6$) $\delta$7.98 (s, 1H), 7.77 (s, 1H), 7.38 (br m, 1H), 7.18 (br d, 1H), 4.97 (m, 2H), 3.90 (m, 1H), 2.46 (s, 3H), 1.08 (d, 3H), 0.84 (s, 9H) ppm. IR (KBr): 3180, 2980, 2250, 1800, 1640 cm$^{-1}$; MS (m/z) 359/361 (M$^+$).

Elemental analysis for $C_{19}H_{23}ClN_3O_2 \cdot 0.04$ $CH_2Cl_2$ Calc'd: C, 62.95; H, 6.13; N, 11.57. Found: C, 62.18; H, 6.09; N, 11.28.

EXAMPLE 35

3-(4-Bromo-2,6-dimethyl-benzylamino)-4-(1,2,2-trimethyl-propylamino)-cyclobut-3-ene-1,2-dione This compound was prepared according to the procedure described in Example 33. From 4-bromo-2,6-dimethylbenzaldehyde oxime (1.13 g, 4.95 mmol), two portions of zinc powder (1.3 g, 20 mmol), glacial acetic acid (19.8 mL), and subsequently 3,4-diethoxy-3-cyclobutene-1,2-dione (0.73 mL, 4.94 mmol) in absolute ethanol (25 mL) there was obtained after chromatography on silica gel (hexane:ethyl acetate (1:0.3), 3% methanol in dichloromethane) 1.11 g (66%) of a solid. From a portion of this solid, 3-(4-bromo-2,6-dimethyl-benzylamino)-4-ethoxy-cyclobut-3-ene-1,2-dione, (0.4 g, 1.18 mmol) and (R)-2-amino-3,3-dimethylbutane (20 mL of a 0.2M solution in absolute ethanol, 4.0 mmol) and dichloromethane (15 mL) there was obtained after 4 days at room temperature a solid, which was filtered, rinsed with absolute ethanol, and dried (0.4 mm, 40° C.). This gave 0.23 g (50%) of the (R) isomer of the title compound as a white solid: mp >300° C.; $^1$H NMR (DMSO-$d_6$) $\delta$7.32 (s, 2H), 7.18 (br m, 1H), 7.08 (br d, 1H), 4.76 (d, 2H), 3.89 (m, 1H), 2.35 (s, 6H), 1.09 (d, 3H), 0.85 (s, 9H) ppm. IR (KBr): 3160, 2950, 1800, 1650 cm$^{-1}$; MS (m/z) 392/394 (M$^+$).

Elemental analysis for $C_{19}H_{25}BrN_2O_2$ Calc'd: C, 58.02; H, 6.41; N, 7.12. Found: C, 57.91; H, 6.25; N, 7.00.

EXAMPLE 36

3-(4-Bromo-2,6-dimethyl-benzylamino)-4-tert-butylamino-cyclobut-3-ene-1,2-dione

A solution of 3-(4-bromo-2,6-dimethyl-benzylamino)-4-ethoxy-cyclobut-3-ene-1,2-dione (0.49 g, 1.45 mmol), t-butylamine (26 mL) and dichloromethane (8 mL) was allowed to stand at room temperature for 18 hours, then refluxed for 8 hours. The resulting solid was filtered, rinsed with acetonitrile, and dried (0.4 mm, 40° C.). This gave 0.33 g (62%) of the title compound as an off-white solid: mp 267°–271° C. (dec); $^1$H NMR (DMSO-$d_6$) $\delta$7.40 (br s, 1H), 7.32 (s, 2H), 7.30 (br t, 1H), 4.76 (d, 2H), 2.34 (s, 6H), 1.34 (s, 9H) ppm. IR (KBr): 3200, 2980, 1790, 1650 cm$^{-1}$; MS (m/z) 364/366 (M$^+$).

Elemental analysis for $C_{17}H_{21}BrN_2O_2$ Calc'd: C, 55.90; H, 5.80; N, 7.67. Found: C, 55.65; H, 5.63; N, 7.63.

EXAMPLE 37

3-(4-Bromo-2,6-dimethyl-benzylamino)-4-(1,1-dimethyl-propylamino)-cyclobut-3-ene-1,2-dione This compound was prepared according to the procedure described in Example 32. From 3-(4-bromo-2,6-dimethyl-benzylamino)-4-ethoxy-cyclobut-3-ene-1,2-dione (0.2 g, 0.59 mmol), 1,1-dimethylpropylamine (5 mL), acetonitrile (10 mL) and dichloromethane (10 mL) there was obtained after 7 days at room temperature, followed by refluxing for 8 hours and removal of solvent under reduced pressure 0.31 g of a solid. This was placed in 5% ethanol in water, filtered, rinsed with water, then ethyl acetate and dried (0.4 mm, 70° C.) to yield 0.16 g (71%) of the title compound as a solid: mp 246°–250° C. (dec) (softens 240° C.); $^1$H NMR (DMSO-$d_6$) $\delta$7.38–7.30 (m with overlapping s at 8 7.32, 3H), 7.26 (br s, 1H), 4.76 (d, 2H), 2.34 (s, 6H), 1.65 (q, 2H), 1.28 (s, 6H), 0.80 (t, 3H) ppm. IR (KBr): 3200, 2980, 1800, 1650 cm$^{-1}$; MS (m/z) 378/380 (M$^+$).

Elemental analysis for $C_{18}H_{23}BrN_2O_2$ Calc'd:C, 57.00; H, 6.11; N, 7.39. Found: C, 56.55; H, 6.08; N, 7.34.

EXAMPLE 38

3-(2-Chloro-4,6-dimethyl-benzylamino)-4-(1,2,2-trimethyl-propylamino)-cyclobut-3-ene-1,2-dione This compound was prepared according to the procedure described in Example 33. From 2-chloro-4,6-dimethylbenzaldehyde oxime (6.63 g, 36 mmol), zinc powder (9.4 g, 144 mmol), glacial acetic acid (72 mL), and 3,4-diethoxy-3-cyclobutene-1,2-dione (5.3 mL, 36 mmol) in absolute ethanol (180 mL) there was obtained after chromatography on silica gel (hexane:ethyl acetate, then 5% methanol in dichloromethane) followed by trituration with 10% ethyl acetate in hexane 5.32 g (50 %) of a solid. From a portion of this solid, 3-(2-chloro-4,6-dimethyl-benzylamino)-4-ethoxy-cyclobut-3-ene-1,2-dione, (0.4 g, 1.36 mmol) and (R)-2-amino-3,3-dimethylbutane (8.2 mL of a 0.2M solution in absolute ethanol, 1.64 mmol) and dichloromethane (3 mL), there was obtained after 4 days at room temperature a solid, which was filtered, rinsed with ethyl acetate, and dried. This gave 0.36 g (76%) of the (R) isomer of the title compound as a white solid: mp >300° C.; $^1$H NMR (DMSO-d$_6$) δ7.26 (br s, 1H), 7.19 (s, 1H), 7.14 (br d, 1H), 7.05 (s, 1H), 4.88 (d, 2H), 3.90 (m, 1H), 2.35 (s, 3H), 2.26 (s, 3H), 1.08 (d, 3H), 0.84 (s, 9H) ppm. IR (KBr): 3170, 2970, 1800, 1650 cm$^{-1}$; MS (m/z) 348/350 (M$^+$).

Elemental analysis for C$_{19}$H$_{25}$ClN$_2$O$_2$ Calc'd: C, 65.41; H, 7.22; N, 8.03. Found: C, 64.55; H, 7.15; N, 7.86.

EXAMPLE 39

3-tert-Butylamino-4-(2-chloro-4,6-dimethyl-benzylamino)-cyclobut-3-ene-1,2-dione This compound was prepared according to the procedure described in Example 36. From 3-(2-chloro-4,6-dimethyl-benzylamino)-4-ethoxy-cyclobut-3-ene-1,2-dione (0.40 g, 1.36 mmol), t-butylamine (2.7 mL) and dichloromethane (1 mL) there was obtained after 4 days at room temperature a solid which was filtered, rinsed with ethyl acetate and dried. This gave 0.28 g (64%) of the title compound as a white solid: mp 292°–294° C.; $^1$H NMR (DMSO-d$_6$) δ7.46 (br m, 1H), 7.38 (br t, 1H), 7.19 (s, 1H), 7.06 (s, 1H), 4.87 (d, 2H), 2.35 (s, 3H), 2.26 (s, 3H), 1.34 (s, 9H) ppm. IR (KBr): 3200, 2980, 1790, 1650 cm$^{-1}$; MS (m/z) 320/322 (M$^+$).

Elemental analysis for C$_{17}$H$_{21}$ClN$_2$O$_2$ Calc'd: C, 63.65; H, 6.60; N, 8.73. Found: C, 63.55; H, 6.61; N, 8.93.

EXAMPLE 40

3-(2-Chloro-4,6-dimethyl-benzylamino)-4-(1,1-dimethyl-propylamino)-cyclobut-3-ene-1,2-dione This compound was prepared according to the procedure described in Example 32. From 3-(2-chloro-4,6-dimethyl-benzylamino)-4-ethoxy-cyclobut-3-ene-1,2-dione (0.40 g, 1.36 mmol), 1,1-dimethylpropylamine (2.7 mL) and dichloromethane (1 mL) there was obtained after 4 days at room temperature a solution which was concentrated under reduced pressure to yield 0.34 g of a solid. This solid was washed with isopropanol, then hexane, and dried (0.4 mm, 70° C.) to give 0.12 g (26%) of the title compound as a white solid: mp 265°–271° C. (dec); $^1$H NMR (DMSO-d$_6$) δ7.41 (t, 1H), 7.32 (s, 1H), 7.19 (s, 1H), 7.06 (s, 1H), 4.89 (d, 2H), 2.35 (s, 3H), 2.26 (s, 3H), 1.65 (q 2H), 1.28 (s, 6H), 0.80 (t, 3H) ppm. IR (KBr): 3190, 2980, 1800, 1650 cm$^{-1}$; MS (m/z) 334/336 (M$^+$).

Elemental analysis for C$_{18}$H$_{23}$ClN$_2$O$_2$ Calc'd: C, 64.57; H, 6.92; N, 8.37. Found: C, 63.81; H, 7.26; N, 8.48.

EXAMPLE 41

3-(2-Chloro-4,6-dimethyl-benzylamino)-4-(2,2,3,3,3-pentafluoro-propylamino)-cyclobut-3-ene-1,2-dione From a solution of 3-(2-chloro-4,6-dimethyl-benzylamino)-4-ethoxy-cyclobut-3-ene-1,2-dione (0.30 g, 1.02 mmol), 2,2,3,3,3-pentafluoropropylamine (2.4 mL), absolute ethanol (2 mL), and dichloromethane (2 mL) there was obtained after 6 days at room temperature a solution which was concentrated under reduced pressure and triturated with dichloromethane to give 0.10 g (25%) of the title compound as a white solid: mp 273°–275° C.; $^1$H NMR (DMSO-d$_6$) δ7.64 (br m, 1H), 7.55 (br m, 1H), 7.19 (s, 1H), 7.05 (s, 1H), 4.87 (d, 2H), 4.43 (dt, 2H), 2.35 (s, 3H), 2.25 (s, 3H) ppm. IR (KBr): 3200, 2980, 1810, 1670 cm$^{-1}$; MS (m/z) 396/398 (M$^+$).

Elemental analysis for C$_{16}$H$_{14}$ClF$_5$N$_2$O$_2$ Calc'd: C, 64.57; H, 6.92; N, 8.37. Found: C, 63.81; H, 7.26; N, 8.48.

EXAMPLE 42

2-Chloro-4-{[3,4-dioxo-2-(1,2,2-trimethyl-pronylamino)-cyclobut-1-enylamino]-methyl}-benzonitrile This compound was prepared according to the procedure described in Example 33, Step 1. From 3-chloro-4-cyanobenzaldehyde oxime (1.26 g, 6.98 mmol), two portions of zinc powder (1.83 g, 28 mmol), glacial acetic acid (13.9 mL), and 3,4-diethoxy-3-cyclobutene-1,2-dione (1.0 mL, 6.76 mmol) in absolute ethanol there was obtained after chromatography on silica gel (hexane:ethyl acetate (1:0.3), 3% methanol in dichloromethane) 1.64 g (81%) of a solid. Following the procedure described in Example 34, a portion of this solid, 3-(3-chloro-4-cyano-benzylamino)-4-ethoxy-cyclobut-3-ene-1,2-dione (0.4 g, 1.38 mmol), (R)-2-amino-3,3-dimethylbutane (20 mL of a 0.2 M solution in absolute ethanol, 4.0 mmol), and dichloromethane (15 mL) was allowed to stand for 4 days at room temperature. The resulting solid was filtered, rinsed with absolute ethanol, and dried (0.4 mm, 40° C.). This gave 0.25 g (52%) of the (R) isomer of the title compound as a white solid: mp 298°–300° C. (dec); [α]$^{25}_D$+27.91° (10.0 mg/mL, DMSO); $^1$H NMR (DMSO-d$_6$) δ7.99 (d, 1H), 7.71 (overlapping s and br m, 2H), 7.49 (d, 1H), 7.33 (br d, 1H), 4.81 (m, 2H), 3.93 (m, 1H), 1.11 (d, 3H), 0.86 (s, 9H) ppm. IR (KBr): 3200, 2960, 2200, 1800, 1650 cm$^{-1}$; MS (m/z) 345/347 (M$^+$).

Elemental analysis for C$_{18}$H$_{20}$ClN$_3$O$_2$ Calc'd: C, 62.52; H, 5.83; N, 12.15. Found: C, 62.38; H, 5.64; N, 12.00.

EXAMPLE 43

4-[(2-tert-Butylamino-3,4-dioxo-cyclobut-1-enylamino)-methyl]-2-chloro-benzonitrile This compound was prepared according to the procedure described in Example 36. From 3-(3-chloro-4-cyano-benzylamino)-4-ethoxy-cyclobut-3-ene-1,2-dione (0.68 g, 2.34 mmol), t-butylamine (6 mL) and dichloromethane (6 mL) there was obtained after 4 days at room temperature a solid which was filtered, rinsed with acetonitrile and dried (0.4 mm, 40° C.). This gave 0.22 g (30%) of the title compound as a yellow solid: mp 276°–278° C. (dec); $^1$H NMR (DMSO-d$_6$) δ7.99 (d, 1H), 7.84 (br t, 1H), 7.72 (d, 1H), 7.61 (br s, 1H), 7.49 (dd, 1H), 4.81 (d, 2H), 1.36 (s, 9H) ppm. IR (KBr): 3220, 2950, 2200, 1795, 1650 cm$^{-1}$; MS (m/z) 317/319 (M$^+$).

Elemental analysis for C$_{16}$H$_{16}$ClN$_3$O$_2$ Calc'd: C, 60.48; H, 5.08; N, 13.22. Found: C, 60.66; H, 5.02; N, 13.11.

EXAMPLE 44

2-Chloro-4-{[2-(1,1-dimethyl-propylamino)-3,4-dioxo-cyclobut-1-enylamino)-methyl}-benzonitrile From a solution of 3-(1,1-dimethypropylamino)-4-ethoxy-cyclobut-3-ene-1,2-dione (0.51 g, 2.41 mmol) and 3-chloro-4-cyanobenzylamine (3.65 mmol) in absolute ethanol there was obtained after 24 hours at room temperature and followed by refluxing for 8 hours a solid. which was filtered. rinsed with ethyl acetate. then hexane. and dried. This gave 0.30 g of a solid which was suspended in 5% ethanol in water. filtered. and rinsed successively with 5% ethanol in water. ethyl acetate. then hexane. and dried (0.4 mm. room temperature) to give 0.26 g (32%) of the title compound as a pale yellow solid: mp 267°–271° C.; $^1$H NMR (DMSO-d$_6$) δ7.99 (d, 1H), 7.85 (br t, 1H), 7.72 (d, 1H), 7.49 (dd, 1H), 7.47 (br s, 1H), 4.81 (d, 2H), 1.67 (q, 2H), 1.30 (s, 6H), 0.82 (t, 3H) ppm. IR (KBr): 3220, 2980, 2250, 1800, 1660 cm$^{-1}$; MS (m/z) 332/334 ([M+H]$^+$).

Elemental analysis for C$_{17}$H$_{18}$ClN$_3$O$_2$ Calc'd: C, 61.54; H, 5.47; N, 12.66. Found: C, 60.91; H, 5.21; N, 12.54.

EXAMPLE 45

4-[{3,4-Dioxo-2-(1,2,2-trimethyl-propylamino)-cyclobut-1-enylamino|-methyl}-2-ethyl-benzonitrile This compound was prepared according to the procedure described in Example 24, Step 1. From 3-ethyl-4-cyanobenzaldehyde oxime (0.88 g, 5.05 mmol), zinc powder (1.32 g, 20 mmol), glacial acetic acid (10 mL), and 3,4-diethyoxy-3-cyclobutene-1,2-dione (0.75 mL, 5.07 mmol) in absolute ethanol (100 mL) there was obtained after chromatography on silica gel (hexane:ethyl acetate (1:1), 5% methanol in dichloromethane) 0.64 g (45%) of a solid. Following the procedure described in Example 34, a portion of this solid, 3-ethoxy-4-(3-ethyl-4-cyano-benzylamino)-cyclobut-3-ene-1,2-dione (0.38 g, 1.34 mmol), (R)-2-amino-3,3-dimethylbutane (10 mL of a 0.2M solution in absolute ethanol, 2.0 mmol), and dichloromethane was allowed to stand for 24 hours at room temperature. The resulting solid was filtered, rinsed with acetonitrile (5×1 mL) and dried. This gave 0.22 g (48%) of the (R) isomer of the title compound as a white solid: mp 251°–253° C.; [α]$^{25}_D$=+28.48° (4.2 mg/mL, DMSO); $^1$H NMR (DMSO-d$_6$) δ7.79 (d, 1H), 7.68 (br m, 1H), 7.44 (s, 1H), 7.34 ( d, 1H), 7.28 (br d, 1H), 4.78 (m, 2H), 3.91 (br m, 1H), 2.79 (q, 2H), 1.21 (t, 3H), 1.10 (d, 3H), 0.85 (s, 9H) ppm. IR (KBr): 3210, 2980, 2210, 1790, 1650 cm$^{-1}$; MS (m/z) 339 (M$^+$).

Elemental analysis for Q$_{20}$E$_{25}$N$_{3O2}$ Calc'd: C, 70.77; H, 7.42; N, 12.38. Found: C, 70.60; H, 7.37; N, 12.40.

EXAMPLE 46

4-[(2-tert-Butylamino-3,4-dioxo-cyclobut-1-enylamino)-methyl]-2-ethyl-benzonitrile This compound was prepared according to the procedure described in Example 36. From 3-ethoxy-4-(3-ethyl-4-cyano-benzylamino)-cyclobut-3-ene-1,2-dione (0.28 g, 0.98 mmol), t-butylamine (2 mL), and dichloromethane there was obtained after 24 hours at room temperature a solid which was filtered, rinsed with acetonitrile (5×1 mL) and dried to give 0.16 g (52%) of the title compound as a pale yellow solid: mp 239°–242° C.; $^1$H NMR (DMSO-d$_6$) δ7.83 (br m, 1H), 7.79 (d, 1H), 7.58 (br s, 1H), 7.45 (s, 1H), 7.34 (dd, 1H), 4.78 (d, 2H), 2.79 (q, 2H), 1.35 (s, 9H), 1.22 (t, 3H) ppm. IR (KBr): 3300, 3240, 2950, 2200, 1780, 1650 cm$^{-1}$; MS (m/z) 311 (M$^+$).

Elemental analysis for C$_{18}$H$_{21}$N$_3$O$_2$ Calc'd: C, 69.43; H, 6.80; N, 13.49. Found: C, 68.64; H, 6.89; N, 13.51.

EXAMPLE 47

3-(4-Bromo-2-ethyl-benzylamino)-4-(1,2,2-trimethyl-propylamino)-cyclobut-3-ene-1,2-dione This compound was prepared according to the procedure described in Example 33. From 4-bromo-2-ethylbenzaldehyde oxime (1.67 g, 7.32 mmol), two portions of zinc powder (1.9 g, 29 mmol), glacial acetic acid (14.6 mL), and 3,4-diethoxy-3-cyclobutene-1,2-dione (1.08 mL, 7.31 mmol) in absolute ethanol (37 mL) there was obtained after chromatography on silica gel (hexane:ethyl acetate (1:0.3), 5% methanol in dichloromethane) and trituration with 10% ethyl acetate in hexane 1.08 g (44%) of a solid. From a portion of this solid, 3-(4-bromo-2-ethyl-benzylamino)-4-ethoxy-cyclobut-3-ene-1,2-dione, (0.28 g, 0.83 mmol) and (R)-2-amino-3,3-dimethylbutane (20 mL of a 0.2M solution in absolute ethanol, 4.0 mmol) and dichloromethane (2 mL) there was obtained after 4 days at room temperature a solid, which was filtered, rinsed with ethyl acetate, and dried (0.4 mm, 40° C.). This gave 0.24 g (73%) of the (R) isomer of the title compound as a white solid: mp 217°–224° C.; |α|$^{25}_D$=+10.52° (9.51 mg/mL, DMSO); $^1$H NMR (DMSO-d$_6$) δ7.50 (br s, 1H), 7.46–7.40 (m with overlapping s at δ7.41, 2H), 7.26 (d, 1H), 7.19 (br d, 1H), 4.74 (d, 2H), 3.90 (m, 1H), 2.64 (q, 2H), 1.15 (t, 3H), 1.09 (d, 3H), 0.85 (s, 9H) ppm. IR (KBr): 3170, 2980, 1800, 1650 cm$^{-1}$; MS (m/z) 392/394 (M$^+$).

Elemental analysis for C$_{17}$H$_{21}$BrN$_2$O$_2$ Calc'd: C, 58.02; H, 6.41; N, 7.12. Found: C, 57.58; H, 6.35; N, 7.10.

EXAMPLE 48

3-(4-Bromo-2-ethyl-benzylamino)-4-tert-butylamino-cyclobut-3-ene-1,2-dione

This compound was prepared according to the procedure described in Example 36. From 3-(4-bromo-2-ethylbenzylamino)-4-ethoxy-cyclobut-3-ene-1,2-dione (0.40 g, 1.18 mmol), t-butylamine (5 mL) and dichloromethane (3 mL) there was obtained after 4 days at room temperature a solid which was filtered, rinsed with ethyl acetate, and dried (0.4 mm, 70° C.). This gave 0.16 g (37%) of the title compound as a pale yellow solid: mp 228°–232° C.; $^1$H NMR (DMSO-d$_6$) δ7.64 (br t, 1H), 7.51 (br s, 1H), 7.45–7.40 (m with overlapping s at δ 7.43, 2H), 7.26 (d, 1H), 4.74 (d, 2H), 2.64 (q, 2H), 1.35 (s, 9H), 1.15 (t, 3H) ppm. IR (KBr): 3210, 2990, 1800, 1660 cm$^{-1}$; MS (m/z) 364/366 (M$^+$).

Elemental analysis for C$_{17}$H$_{21}$BrN$_2$O$_2$ Calc'd: C, 55.90; H, 5.80; N, 7.67. Found: C, 55.99; H, 5.67; N, 7.64.

EXAMPLE 49

3-(4-Bromo-2-ethyl-benzylamino)-4-(1,1-dimethyl-propylamino)-cyclobut-3-ene-1,2-dione This compound was prepared according to the procedure described in Example 32. From 3-(4-bromo-2-ethylbenzylamino)-4-ethoxy-cyclobut-3-ene-1,2-dione (0.4 g, 1.18 mmol), 1,1-dimethylpropylamine (5 mL), and dichloromethane (2 mL) there was obtained after 4 days at room temperature and followed by removal of solvent under reduced pressure a solid. This was placed in acetonitrile, filtered, rinsed with acetonitrile, and dried (0.4 mm, 70° C.) to yield 0.30 g (67%) of the title compound as a white solid: mp 182°–186° C.; $^1$H NMR (DMSO-d$_6$) δ7.68 (br t, 1H), 7.45–7.40 (m with overlapping s at δ7.43, 2H), 7.38 (br s, 1H), 7.25 (d, 1H), 4.75 (d, 2H), 2.64 (q, 2H), 1.66 (q 2H), 1.29 (s, 6H), 1.15 (t, 3H), 0.80 (t, 3H) ppm. IR (KBr): 3210, 2980, 1800, 1650 cm$^{-1}$; MS (m/z) 378/380 (M$^+$).

Elemental analysis for C$_{18}$H$_{23}$BrN$_2$O$_2$ Calc'd:C, 57.00; H, 6.11; N, 7.38. Found: C, 56.23; H, 6.14; N, 7.35.

EXAMPLE 50

4-[(1,1-Dimethyl-propylamino-3,4-dioxo-cyclobut-1-enylamino)-methyl]-3-ethyl-benzonitrile From a solution of 3-(1,1-dimethypropylamino)-4-ethoxy-cyclobut-3-ene-1,2-dione (0.34 g, 1.61 mmol) and 4-cyano-2-ethylbenzylamine (7.7 mmol) in absolute ethanol there was obtained 9 days at room temperature and followed by removal of solvent under reduced pressure a solid. This solid was chromatographed on silica gel (5% methanol in dichloromethane) to give a residue, which was trituated with acetonitrile, filtered, rinsed with acetonitrile, and dried to yield 0.31 g (12%) of the title compound as an off-white solid: mp 183°–186° C.; $^1$H NMR (DMSO-d$_6$) δ7.80–7.70 (m with overlapping br t at δ7.75, 3H), 7.47 (d, 1H), 7.43 (br s, 1H), 4.85 (d, 2H), 2.69 (q, 2H), 1.66 (q, 2H), 1.30 (s, 6H), 1.17 (t, 3H), 0.81 (t, 3H) ppm. IR (KBr): 3210, 2980, 2240, 1800, 1650 cm$^{-1}$; MS (m/z) 326 (|M+H|$^+$).

Elemental analysis for C$_{19}$H$_{23}$N$_3$O$_2$ Calc'd: C, 70.13; H, 7.13; N, 12.91. Found: C, 70.18; H, 6.99; N, 12.82.

EXAMPLE 51

3-(2,6-Dimethyl-benzylamino)-4-(1,2,2-trimethyl-propylamino)-cyclobut-3-ene-1,2-dione Step 1) Preparation of 3-(2,6-dimethyl-benzylamino)-4-ethoxy-cyclobut-3-ene-1,2-dione This compound was prepared according to the procedure described in Example 24, Step 1. From 2,6-dimethylbenzaldehyde oxime (2.67 g, 18 mmol), zinc powder (4.68 g, 72 mmol), glacial acetic acid (35.7 mL), and 3,4-diethoxy-3-cyclobutene-1,2-dione (2.65 mL, 18 mmol) in absolute ethanol there was obtained after chromatography on silica gel (hexane:ethyl acetate (3:1), 5% methanol in dichloromethane) 2.0 g (43%) of a solid: $^1$H NMR (DMSO-d$_6$) δ8.90 and 8.70 (br m, 1H, rotamers), 7.20–7.00 (m, 3H), 4.90–4.50 (m, 4H), 2.30 (s, 6H), 1.38 (m, 3H).

Step 2) 3-(2,6-Dimethyl-benzylamino)-4-(1,2,2-trimethyl-propylamino)-cyclobut-3-ene-1,2-dione This compound was prepared according to the procedure described in Example 34. From the product of Example 51, Step 1 (0.3 g, 1.16 mmol) and (R)-2-amino-3,3-dimethylbutane (26 mL of a 0.2M solution in absolute ethanol, 5.2 mmol), there was obtained after 24 hours at room temperature, followed by refluxing for 4–5 hours, a solid, which was filtered, rinsed with acetonitrile (3×3 mL) and dried to give 0.33 g (90%) of the (R) isomer of the title compound as a white solid: mp 298°–301° C. (dec); $[\alpha]^{25}_D$= +15.38° (9.9 mg/mL, DMSO); $^1$H NMR (DMSO-d$_6$) δ7.17 (br m, 1H), 7.16–7.05 (m, 4H), 4.80 (d, 2H), 3.90 (m, 1H), 2.35 (s, 6H), 1.08 (d, 3H), 0.84 (s, 9H) ppm. IR (KBr): 3150, 2980, 1800, 1650 cm$^{-1}$; MS (m/z) 314 (M$^+$).

Elemental analysis for C$_{19}$H$_{26}$N$_2$O$_2$ Calc'd: C, 72.58; H, 8.34; N, 8.91. Found: C, 72.44; H, 8.41; N, 8.91.

EXAMPLE 52

3-tert-Butylamino-4-(2,6-dimethyl-benzylamino)-cyclobut-3-ene-1,2-dione

This compound was prepared according to the procedure described in Example 36. From the product of Example 51, Step 1 (0.32 g, 1.23 mmol), t-butylamine (2 mL), and dichloromethane there was obtained after 48 hours at room temperature a solid which was diluted with acetonitrile (4 mL), filtered, rinsed with acetonitrile (3×2 mL) and dried to give 0.17 g (48%) of the title compound as a white solid: mp 265°–267° C.; $^1$H NMR (DMSO-d$_6$) δ7.39 (br s, 1H), 7.29 (br t, 1H), 7.16–7.05 (m, 3H), 4.79 (d, 2H), 2.34 (s, 6H), 1.34 (s, 9H) ppm. IR (KBr): 3200, 2950, 1795, 1650 cm$^{-1}$; MS (m/z) 287 (|M+H|$^+$).

Elemental analysis for C$_{17}$H$_{22}$N$_2$O$_2$ Calc'd: C, 71.30; H, 7.74; N, 9.78. Found: C, 70.58; H, 7.75; N, 9.69.

EXAMPLE 53

3-(2,6-Dimethyl-benzylamino)-4-(1,1-dimethyl-propylamino)-cyclobut-3-ene-1,2-dione This compound was prepared according to the procedure described in Example 32. From the product of Example 51, Step 1 (0.4 g, 1.54 mmol), 1,1-dimethylpropylamine (5 mL), and dichloromethane (2 mL) there was obtained after refluxing for 8 hours and removal of solvent under reduced pressure 0.44 g of a solid, which was placed in isopropanol, filtered, and the filtrate was concentrated under reduced pressure. The resulting solid was placed in ethyl acetate, filtered, rinsed with ethyl acetate, and dried (0.4 mm, 70° C.). This gave 0.21 g (45%) of the title compound as a solid: mp 227°–231° C. (softens 199° C.); $^1$H NMR (DMSO-d$_6$) δ7.32 (br t, 1H), 7.26 (br s, 1H), 7.17–7.05 (m, 3H), 4.80 (d, 2H), 2.34 (s, 6H), 1.65 (q 2H), 1.28 (s, 6H), 0.79 (t, 3H) ppm. IR (KBr): 3200, 2980, 1800, 1650 cm$^{-1}$; MS (m/z) 300 (M$^+$).

Elemental analysis for C$_{18}$H$_{24}$N$_2$O$_2$ Calc'd: C, 71.97; H, 8.05; N, 9.33. Found: C, 71.65; H, 8.27; N, 9.30.

EXAMPLE 54

3-(2,6-Dimethyl-benzylamino)-4-(2,2,3,3,3-pentafluoro-propylamino)-cyclobut-3-ene-1,2-dione From a solution of 3-(2,6-dimethyl-benzylamino)-4-ethoxy-cyclobut-3-ene-1,2-dione (0.30 g, 1.16 mmol), 2,2,3,3,3-pentafluoropropylamine (2.4 mL), absolute ethanol (2 mL), and dichloromethane (2 mL) there was obtained after 6 days at room temperature a solution which was concentrated under reduced pressure and triturated with dichloromethane to give 0.05 g (12%) of the title compound as a white solid: mp 281°–283° C.; $^1$H NMR (DMSO-d$_6$) δ7.56 (br m, 1H), 7.46 (br m, 1H), 7.18–7.04 (m, 3H), 4.80 (d, 2H), 4.42 (dt, 2H), 2.34 (s, 6H) ppm. MS (m/z) 363 (|M+H|+).

Elemental analysis for C$_{16}$H$_{15}$F$_5$N$_2$O$_2$ Calc'd: C, 53.04; H, 4.17; N, 7.73. Found: C, 52.08; H, 4.06; N, 7.54.

EXAMPLE 55

4-{[3,4-Dioxo-2-(1,2,2-trimethyl-propylamino)-cyclobut-1-enylamino|-methyl}-3-methyl-benzonitrile This compound was prepared in a manner similar to Example 51 using appropriate starting materials to afford the (R) isomer of the title compound as a pale pink solid: mp 250°–258° C. (softens 242° C.); $^1$H NMR (DMSO-d$_6$) δ7.70 (m, 2H), 7.60 (br m, 1H), 7.45 (d, 1H), 7.27 (br d, 1H), 4.80 (m, 2H), 3.91 (m, 1H), 2.35 (s, 3H), 1.11 (d 3H), 0.86 (s, 9H) ppm. IR (KBr): 3180, 2950, 2200, 1790, 1650 cm$^{-1}$; MS (m/z) 325 (M$^+$).

Elemental analysis for C$_{19}$H$_{23}$N$_3$O$_2$ Calc'd: C, 70.13; H, 7.12; N, 12.91. Found: C, 69.81; H, 7.14; N, 12.96.

EXAMPLE 56

4-{[3,4-Dioxo-2-(1,2,2-trimethyl-propylamino)-cyclobut-1-enylamino|-methyl}-3-methoxy-benzonitrile This compound was prepared in a manner similar to Example 51 using appropriate starting materials to afford the (R) isomer of the title compound as a white solid: mp 172°–178° C.; $^1$H NMR (DMSO-d$_6$) δ7.61 (br m, 1H), 7.51 (s, 1H), 7.49–7.38 (m, 2H), 7.32 (br d, 1H), 4.73 (m, 2H), 3.89 (overlapping s and m, 4H), 1.10 (d, 3H), 0.86 (s, 9H) ppm. MS (m/z) 341 (M⁺).

Elemental analysis for C₁₉H₂₃N₃O₃ Calc'd: C, 66.84; H, 6.79; N, 12.31. Found: C, 66.38; H, 6.78; N, 12.16.

EXAMPLE 57

3-(2-Methoxy-6-methyl-benzylamino)-4-(1,2,2-trimethyl-propylamino)-cyclobut-3-ene-1,2-dione This compound was prepared in a manner similar to Example 51 using appropriate starting materials to afford the (R) isomer of the title compound as a white solid: mp 278°–280° C. (dec); $[\alpha]^{25}_D$=+28.76° (9.8 mg/mL, DMSO); ¹H NMR (DMSO-d₆) δ7.21 (t, 1H), 7.17 (m, 1H), 7.15 (m, 1H), 6.90 (d, 1H), 6.82 (d, 1H), 4.78 (m, 2H), 3.89 (m, 1H), 3.81 (s, 3H), 2.32 (s, 3H), 1.08 (d, 3H), 0.84 (s, 9H) ppm. IR (KBr): 3150, 2970, 1795, 1645 cm⁻¹; MS (m/z) 330 (M⁺).

Elemental analysis for C19H₂₆N₂O₃ Calc'd: C, 69.06; H, 7.93; N, 8.48. Found: C, 69.16; H, 7.99; N, 8.47.

EXAMPLE 58

3-tert-Butylamino-4-(2-ethyl-6-methyl-benzylamino)-cyclobut-3-ene-1,2-dione

This compound was prepared in a manner similar to Example 51 using appropriate starting materials to afford the title compound as a white solid: mp melts and resolidifies at 183°–186° C., then melts at 240°–244° C.; ¹H NMR (DMSO-d₆) δ7.39 (br s, 1H), 7.29 (br t, 1H), 7.22–7.06 (m, 3H), 4.80 (d, 2H), 2.67 (q, 2H), 2.35 (s, 3H), 1.34 (s, 9H), 1.13 (t, 3H) ppm. MS (m/z) 300 (M⁺).

Elemental analysis for C₁₈H₂₄N₂O₂ Calc'd: C, 71.97; H, 8.05; N, 9.33. Found: C, 71.32; H, 8.20; N, 9.17.

EXAMPLE 59

3-tert-Butylamino-4-(4-fluoro-2-trifluoromethyl-benzylamino)-cyclobut-3-ene-1,2-dione To a room temperature solution of (0.7 g, 3.55 mmol) of 3-ethoxy-4-(tert-butylamino)-cyclobut-3-ene-1,2-dione and THF (30 mL) was added (0.73 g, 3.78 mmol) of the 4-fluoro-2-trifluoromethylbenzylamine via a syringe. The resulting mixture was stirred at room temperature for 12 hours. After concentration in vacuo, the resulting white solid was recrystallized from hot acetonitrile to give 0.55 gm (52%) of 3-tert-butylamino-4-(4-fluoro-2-trifluoromethyl-benzylamino)-cyclobut-3-ene-1,2-dione as a white solid: mp 192°–194° C.; ¹H NMR (DMSO-d₆) δ1.36 (s, 9H), 4.88 (d, 2H) 7.67 (m, 5H) ppm; IR (KBr) 3250, 2900, 1800, 1580, 1530 cm⁻¹; MS (m/z) 345 ([M+H]⁺).

Elemental analysis for C₁₆H₁₆F₄N₂O₂ Calc'd: C, 55.82; H, 4.68; N, 8.14. Found: C, 55.68; H, 8.02; N, 8.02.

EXAMPLE 60

3-tert-Butylamino-4-(2-chloro-4-fluoro-benzylamino)-cyclobut-3-ene-1,2-dione

This compound was prepared according the procedure for Example 59. From 2-chloro-4-fluorobenzylamine and 3-ethoxy-4-(tert-butylamino)-cyclobut-3-ene-1,2-dione there was obtained a white solid (59%): mp 202°–204° C.; ¹H NMR (DMSO-d₆) δ1.36 (s, 9H), 3.34 (m, 1H), 4.80 (d, 2H), 7.28 (m, 1H), 7.53 (m, 2H), 7.67 (m, 1H) ppm; IR (KBr) 3260, 2950, 1800, 1660, 1570, 1530, 1500 cm⁻¹; MS (m/z) 311 ([M+H]⁺).

Elemental analysis for C₁₅H₁₆ClFN₂O₂ Calc'd: C, 57.98; H, 5.19; N, 9.01. Found: C, 58.13; H, 5.33; N, 8.46.

EXAMPLE 61

3-(4-Fluoro-2-trifluoromethyl-benzylamino)-4-(1,2,2-trimethyl-propylamino)-cyclobut-3-ene-1,2-dione This compound was prepared according to the procedure for Example 59. From (R)-3-ethoxy-4-(1,2,2-trimethyl-propylamino)-cyclobut-3-ene-1,2-dione and 4-fluoro-2-trifluoromethylbenzylamine in acetonitrile. After recrystallization from diethyl ether the (R) isomer of the title acompound was obtained as a white solid (54%): mp 208°–210° C.; IR (KBr) 3260, 2950, 1800, 1660, 1570, 1530, 1500 cm⁻¹; MS (m/z) 373 ([M+H]⁺).

Elemental analysis for C₁₈H₂₀F₄N₂O₂ Calc'd: C, 58.06; H, 5.41; N, 7.52. Found: C, 58.42; H, 5.62; N, 7.51.

EXAMPLE 62

3-(2,4-Difluoro-benzylamino)-4-(1,1-dimethyl-propylamino)-cyclobut-3-ene-1,2-dione This compound was prepared according to the procedure for Example 59. From 3-ethoxy-4-(1,1-dimethyl-propylamino)-cyclobut-3-ene-1,2-dione and 2,4-difluorobenzylamine in acetonitrile. The title compound was obtained, after recrystallization from diethyl ether, as a white solid (80%): mp 242°–244° C.; ¹H NMR (DMSO-d₆) δ0.82 (t, 3H), 1.30 (s, 6H), 1.68 (q, 2H), 4.76 (d, 2H), 7.09 (m, 1H), 7.27 (m, 1H), 7.50 (m, 2H), 7.80 (m, 1H) ppm; IR (KBr) 3250, 3150, 2970, 1790, 1652, 1580, 1538, 1510 cm⁻¹; MS (m/z) 309 ([M+H]⁺).

Elemental analysis for C₁₆H₁₈F₂N₂O₂ Calc'd: C, 62.33; H, 5.88; N, 9.09. Found: C, 62.29; H, 5.93; N, 8.90.

EXAMPLE 63

3-(2-Chloro-4-fluoro-benzylamino)-4-(1,1-dimethyl-propylamino)-cyclobut-3-ene-1,2-dione This compound was prepared according to the procedure for Example 59. From 2-chloro-4-fluorobenzylamine and 3-ethoxy-4-(1,1-dimethyl-propylamino)-cyclobut-3-ene-1,2-dione in acetonitrile. The title compound was obtained, after recrystallization from petroleum ether, as a white solid (60%); mp 201°–203° C.; ¹H NMR (DMSO-d₆) δ0.81 (t, 3H), 1.30 (s, 6H), 1.68 (q, 2H), 4.76 (d, 2H), 7.25 (m, 1H), 7.50 (m, 3H), 7.78 (m, 1H) ppm; IR (KBr) 3250, 3040, 1790, 1660, 1580, 1530, 1490 cm⁻¹; MS (m/z) 325 ([M+H]⁺).

Elemental analysis for C₁₆H₁₈ClFN₂O₂ Calc'd: C, 59.17; H, 5.59; N, 8.63. Found: C, 59.17; H, 5.50; N, 8.51.

EXAMPLE 64

3-tert-Butylamino-4-(2-fluoro-5-trifluoromethyl-benzylamino)-cyclobut-3-ene-1,2-dione This compound was prepared according to the procedure for Example 59. From 2-fluoro-5-trifluoromethylbenzylamine and 3-ethoxy-4-(tert-butylamino)-cyclobut-3-ene-1,2-dione the title compound was obtained as a white solid (66%): mp 225°–227° C.; ¹H NMR (DMSO-d₆) δ1.35 (s, 9H), 4.75 (d, 2H), 7.51 (m, 2H), 7.83 (m, 3H) ppm; IR (KBr) 3233, 3045, 1794, 1658, 1571, 1537, 1471 cm⁻¹; MS (m/z) 345 ([M+H]⁺).

Elemental analysis for C₁₆H₁₆F₄N₂O₂ Calc'd: C, 55.82; H, 4.68; N, 8.14. Found: C,55.74; H, 4.46; N, 7.95.

EXAMPLE 65

3-(2-Chloro-5-fluoro-benzylamino)-4-(1,2,2-trimethyl-propylamino)-cyclobut-3-ene-1,2-dione This compound was prepared according to the procedure for Example 59. From (R)-3-ethoxy-4-(1,2,2-trimethyl-propylamino)-cyclobut-3-ene-1,2-dione and 2-chloro-5-fluoro-benzylamine there was obtained after recrystallization from diethyl ether, the (R) isomer of the title compound as a white solid (80%): mp 218°–220° C.; $^1$H NMR (DMSO-d$_6$) δ0.87 (s, 9H), 1.11 (d, Hz, 3H), 3.91 (m, 1H), 4.80 (q, 2H), 7.30 (m, 2H), 7.50 (m, 2H), 7.60 (m, 1H) ppm; IR (KBr) 3194, 3063, 1797, 1654, 1578, 1541, 1492 cm$^{-1}$; MS (m/z) 339 (|M+H|$^+$).

Elemental analysis for C$_{17}$H$_{20}$ClFN$_2$O$_2$ Calc'd: C, 60.27; H, 5.95; N, 8.27. Found: C, 60.44; H, 6.01; N, 8.11.

EXAMPLE 66

3-(2,5-Difluoro-benzylamino)-4-(1,2,2-trimethyl-propylamino)-cyclobut-3-ene-1,2-dione This compound was prepared according to the procedure for Example 59. From (R)-3-ethoxy-4-(1,2,2-trimethyl-propylamino)-cyclobut-3-ene-1,2-dione and 2,5-difluorobenzylamine there was obtained after recrystallization from diethyl ether, the (R) isomer of the title compound as a white solid (85%): mp 265°–267° C.; $^1$H NMR (DMSO-d$_6$) δ0.87 (s, 9H), 1.11 (d, 3H), 3.91 (m, 1H), 4.80 (q, 2H), 7.25 (m, 4H), 7.60 (m, 1H) ppm; IR (KBr) 3195, 3068, 1798, 1653, 1577, 1543, 1494 cm$^{-1}$; MS: 323 ([M+H]$^+$).

Elemental analysis for C$_{17}$H$_{20}$F$_2$N$_2$O$_2$ Calc'd: C, 63.34; H, 6.25; N, 8.69. Found: C, 63.55; H, 6.30; N, 8.59.

EXAMPLE 67

3-tert-Butylamino-4-(3-chloro-4-fluoro-benzylamino)-cyclobut-3-ene-1,2-dione

This compound was prepared according to the procedure for Example 59. From 3-chloro-4-fluorobenzylamine and 3-ethoxy-4-(tert-butylamino)-cyclobut-3-ene-1,2-dione, the title compound was obtained as a white solid (59%): mp 288°–290° C.; $^1$H NMR (DMSO-d$_6$) δ1.36 (s, 9H), 4.80 (d, 2H) 7.44 (m, 2H), 7.60 (m, 2H) 7.75 (m, 1H) ppm; IR (KBr) 3233, 3039, 1792, 1652, 1571, 1537, 1501 cm$^{-1}$; MS (m/z) 311 ([M+H]$^+$).

Elemental analysis for C$_{15}$H$_{16}$ClFN$_2$O$_2$ Calc'd: C, 57.98; H, 5.19; N, 9.01. Found: C, 58.02; H, 5.24; N, 8.82.

EXAMPLE 68

3-tert-Butylamino-4-(3,4-difluoro-benzylamino)-cyclobut-3-ene-1,2-dione

This compound was prepared according to the procedure for Example 59. From 3,4-difluorobenzylamine and 3-ethoxy-4-(tert-butylamino)-cyclobut-3-ene-1,2-dione, the title compound was obtained as a white solid (77%): mp 296°–298° C.; $^1$H NMR (DMSO-d$_6$) δ1.36 (s, 9H), 4.72 (d, 2H) 7.22 (m, 1H), 7.56 (m, 3H), 7.77 (m, 1H) ppm; IR (KBr) 3235, 2970, 1790, 1650, 1570, 1540, 1490 cm$^{-1}$; MS (m/z) 295 ([M+H]$^+$)

Elemental analysis for C$_{15}$H$_{16}$F$_2$N$_2$O$_2$ Calc'd: C, 61.22; H, 5.48; N, 9.52. Found: C, 61.05; H, 5.40; N, 9.31.

EXAMPLE 69

3-(3-Chloro-4-fluoro-benzylamino)-4-(1,2,2-trimethyl-propylamino)-cyclobut-3-ene-1,2-dione This compound was prepared according to the procedure for Example 59. From (R)-3-ethoxy-4-(1,2,2-trimethyl-propylamino)-cyclobut-3-ene-1,2-dione and 3-chloro-4-fluorobenzylamine, the (R) isomer of the title compound was obtained after recrystallization from diethyl ether, as a white solid (73%): mp 270°–272° C.; $^1$H NMR (DMSO-d$_6$) δ0.87 (s, 9H), 1.11 (d, 3H), 3.91 (m, 1H), 4.80 (q, 2H), 7.45 (m, 3H), 7.60 (m, 2H) ppm; IR (KBr) 3201, 3062, 1798, 1650, 1575, 1492 cm$^{-1}$; MS (m/z) 339 (|M+H|$^+$).

Elemental analysis for C$_{17}$H$_{20}$ClFN$_2$O$_2$ Calc'd: C, 60.27; H, 5.95; N, 8.27. Found: C, 60.27; H, 6.32; N, 8.18.

EXAMPLE 70

3-(3,4-Difluoro-benzylamino)-4-(1,1-dimethyl-propylamino)-cyclobut-3-ene-1,2-dione This compound was prepared according to the procedure for Example 59. From 3-ethoxy-4-(1,1-dimethyl-propylamino)-cyclobut-3-ene-1,2-dione and 3,4-difluorobenzylamine in acetonitrile there was obtained after recrystallization from diethyl ether, the title compound as a white solid (62%): mp 273°–275° C.; $^1$H NMR (DMSO-d$_6$) d 0.82 (t, 3H), 1.30 (s, 6H), 1.68 (q, 2H) 4.71 (d, 2H), 7.21 (m, 1H), 7.44 (m, 3H), 7.81 (m, 1H) ppm; IR (KBr) 3290, 2970, 1790, 1652, 1570, 1538, 1510 cm$^{-1}$; MS (m/z) 309 ([M+H]$^+$).

Elemental analysis for C$_{16}$H$_{18}$F$_2$N$_2$O$_2$ Calc'd: C, 62.33; H, 5.88; N, 9.09. Found: C, 62.36; H, 5.83; N, 8.91.

EXAMPLE 71

3-tert-Butyl amino-4-(3,5-difluoro-benzylamino)-cyclobut-3-ene-1,2-dione

This compound was prepared according the procedure for Example 59. From 3,5-difluorobenzylamine and 3-ethoxy-4-(tert-butylamino)-cyclobut-3-ene-1,2-dione there was obtained the title compound as a white solid (77%): mp 287°–289° C.; $^1$H NMR (DMSO-d$_6$) δ1.37 (s, 9H), 4.74 (d, 2H), 7.08 (m, 2H), 7.12 (m, 1H), 7.60 (m, 1H), 7.80 (m, 1H) ppm; IR (KBr) 3280, 3080, 1793, 1656, 1571, 1538, 1470 cm$^{-1}$; MS (m/z) 294 ([M+H]$^+$).

Elemental analysis for C$_{15}$H$_{16}$F$_2$N$_2$O$_2$ Calc'd: C, 61.22; H, 5.48; N, 9.52. Found: C, 61.29; H, 5.63; N, 9.29.

EXAMPLE 72

3-tert-Butylamino-4-(3-fluoro-5-trifluoromethyl-benzylamino)-cyclobut-3-ene-1,2-dione This compound was prepared according to the procedure for Example 59. From 3-fluoro-5-trifluoromethylbenzylamine and 3-ethoxy-4-(tert-butylamino)-cyclobut-3-ene-1,2-dione there was obtained after recrystallization from diethyl ether, the title compound as a white solid (53%): mp 246°–248° C.; $^1$H NMR (DMSO-d$_6$) d 1.37 (s, 9H), 4.75 (d, 2H), 7.63 (m, 3H), 7.82 (m, 1H) ppm; IR (KBr): 3230, 3040, 1794, 1658, 1571, 1537, 1470 cm$^{-1}$; MS (m/z) 344 ([M+H]$^+$).

Elemental analysis for C$_{16}$H$_{16}$F$_4$N$_2$O$_2$ Calc'd: C, 55.82; H, 4.68; N, 8.14. Found: C, 55.81; H, 4.55; N, 8.13.

EXAMPLE 73

3-(3,5-Bis-trifluoromethyl-benzylamino)-4-tert-butylamino-cyclobut-3-ene-1,2-dione This compound was prepared according to the procedure for Example 59. From 3,5-bis-trifluoromethylbenzylamine and 3-ethoxy-4-(tert-butylamino)-cyclobut-3-ene-1,2-dione the title compound was obtained as a white solid (58%): mp 253°–255° C.; $^1$H NMR (DMSO-d$_6$) δ1.36 (s, 9H), 4.74 (d, 2H), 7.61 (s., 3H), 7.85 (s, 1H), 7.81 (m, 1H) ppm; IR (KBr) 3243, 3055, 1794, 1661, 1575, 1537, 1470 cm$^{-1}$; MS (m/z) 394 ([M+H]$^+$).

Elemental analysis for C$_{17}$H$_{16}$F$_6$N$_2$O$_2$ Calc'd: C, 51.78; H, 4.09; N, 7.10. Found: C, 52.70; H, 4.10; N, 7.15.

EXAMPLE 74

3-(3,5-Difluoro-benzylamino)-4-(1,1-dimethyl-propylamino)-cyclobut-3-ene-1,2-dione This compound was prepared according to the procedure for Example 59. From 3-ethoxy-4-(1,1,-dimethyl-propylamino)-cyclobut-3-ene-1,2-dione and 3,5-difluorobenzylamine the title compound was obtained after recrystallization from diethyl ether, as a white solid (81%): mp 264°–266° C.; $^1$H NMR (DMSO-d$_6$) δ0.83 (t, 3H), 1.31 (s, 6H), 1.68 (q, 2H), 4.75 (d, 2H), 7.07 (m, 2H), 7.18 (m, 1H), 7.43 (s, 1H), 7.82 (m, 1H) ppm. IR (KBr): 3294, 2977, 1796, 1655, 1574, 1538, 1465 cm$^{-1}$; MS (m/z) 309 ([M+H]$^+$).

Elemental analysis for C$_{16}$H$_{11}$F$_2$N$_2$O$_2$ Calc'd: C, 62.33; H, 5.88; N, 9.09. Found: C, 62.37; H, 5.97; N, 8.95.

EXAMPLE 75

3-Chloro-4-{[2-(2-fluoro-1,2-dimethyl-propylamino)-34-dioxo-cyclobut-1-enylamino]-methyl}-benzonitrile

Step 1) 3-Fluorovalinol

To a solution of lithium borohydride (1.61 g, 74 mmol) in tetrahydrofuran (40 mL) under a nitrogen atmosphere was added trimethylsilyl chloride (18.8 mL, 148 mmol) via pipet. A precipitate quickly formed. After 3 minutes, 3-fluorovaline (5 g, 37 mmol) was added in three portions. This mixture was stirred for 24 hours. The reaction was quenched by the dropwise addition of methanol. The methanol and tetrahydrofuran were removed on a rotary evaporator (30 degree water bath) and water (25 mL) was added. The aqueous mixture was made basic with 2.5N aqueous sodium hydroxide and was then extracted with dichloromethane (4×50 mL). The combined organics were dried (Na$_2$SO$_4$), filtered and evaporated to give 3.83 g of 3-fluorovalinol: $^1$H NMR (CDCl$_3$) δ3.71 (dd, 1H), 3.36 (m, 1H), 2.90 (m,1H), 2.10 (br, 2H), 1.38 (d, 3H), 1.33 (d, 3H) ppm.

Step 2) N-Butoxycarbonyl-3-fluorovalinol

To a solution of 3-fluorovalinol (3.79 g, 31.4 mmol) in chloroform (35 mL) under a nitrogen atmosphere was added a solution of di-t-butyl dicarbonate (6.84 g, 31.4 mmol) in chloroform (15 mL). The mixture was stirred at room temperature for four hours, then the solvent was removed on a rotary evaporator. The residue was dissolved in diethyl ether (100 mL), washed with 20% phosphoric acid (1×50 mL), brine (1×50 mL), saturated aqueous sodium bicarbonate (1×50 mL), brine (1×50 mL), and then dried (MgSO$_4$). Filtration and concentration under reduced pressure gave 6.34 g of N-butoxycarbonyl-3-fluorovalinol as a white solid: $^1$H NMR (CDCl$_3$) δ5.08 (br, 1H), 3.82 (m, 1H), 3.68 (m, 1H), 1.46 (s, 9H), 1.46 (d, 3H), 1.39 (d, 3H) ppm.

Step 3) N-Butoxycarbonyl-1-iodo-2-amino-3-fluoro-3-methyl-n-butane

To a well-stirred mixture of polystyryl supported triphenylphosphine (29.3 mmol) in dry dichloromethane (40 mL) under a nitrogen atmosphere was added iodine (7.44 g, 29.3 mmol). After ten minutes, imidazole (2.0 g, 29.3 mmol) was added, followed in ten minutes by a solution of N-butoxycarbonyl-3-fluorovalinol (13.3 mmol) in dichloromethane (200 mL). The mixture was heated to reflux for two hours. The cooled mixture was filtered through celite and the filtrate was evaporated. The residue was dissolved in diethyl ether (150 mL), and this solution was washed with dilute aqueous sodium thiosulfate (1×75 mL) and water (2×75 mL). The organic layer was dried (Na$_2$SO$_4$), filtered through a pad of silica gel and evaporated to afford 3.46 g of N-butoxycarbonyl-1-iodo-2-amino-3-fluoro-3-methyl-n-butane: $^1$H NMR (CDCl$_3$) δ4.72 (br d, 1H), 3.86 (br m, 1H), 3.56 (dd, 1H), 1.47 (s, 9H), 1.43 (m, 6H) ppm.

Step 4) N-Butoxycarbonyl-2-amino-3-fluoro-3-methyl-n-butane

A Parr bottle was charged with palladium (II) hydroxide (800 mg), a solution of N-butoxycarbonyl-1-iodo-2-amino-3-fluoro-3-methyl-n-butane (3.26 g, 9.8 mmol) in ethanol (80 mL) and triethylamine (0.99 g, 9.8 mmol). The reaction mixture was placed under hydrogen gas (50 psig) and shaken for 20 hours. The mixture was filtered through Celite® and evaporated. The residue was dissolved in diethyl ether (100 mL) and washed with 1N aqueous HCl (2×50 mL), water (2×50 mL), and then dried (MgSO$_4$). Filtration and evaporation gave a residue that was chromatographed (silica gel, diethyl ether/hexane (3/1)) to afford 1.80 g of N-butoxycarbonyl-2-amino-3-fluoro-3-methyl-n-butane: $^1$H NMR (CDCl$_3$) δ4.65 (br, 1H), 3.70 (br m, 1H), 1.45 (s, 9H), 1.39 (d, 3H), 1.32 (d, 3H), 1.18 (d, 3H) ppm.

Step 5) 3-Ethoxy-4-(N-3-fluoro-3-methyl-n-butyl-2-amine)-3-cyclobutene-1,2-dione A mixture of N-butoxycarbonyl-2-amino-3-fluoro-3-methyl-n-butane (1.75 g, 8.5 mmol), dichloromethane (5 mL), trifluoroacetic acid (4 mL), and methanol (0.75 mL) were warmed to 45° C. for five hours. The volatile components were removed on a rotary evaporator and the syrupy residue was used without further purification. To a solution of 3-fluoro-3-methyl-n-butyl-2-amine trifluoroacetate salt (8.5 mmol) in ethanol (42.5 mL) was added 3,4-diethoxy-3-cyclobutene-1,2-dione (1.44 g, 8.5 mmol) followed by triethylamine (2.58 g, 25.5 mmol). The reaction mixture was stirred under a nitrogen atmosphere at room temperature for two hours then the temperature was raised to 50° C. for five hours. The mixture was cooled and the solvents removed on a rotary evaporator. The residue was dissolved in diethyl ether (90 mL) and washed with water (1×60 mL), 1N aqueous HCl (1×60 mL), water 1×60 mL). The organic layer was dried (MgSO$_4$), filtered, and evaporated. The residue was chromatographed (silica gel, diethyl ether) to afford 1.65 g of 3-ethoxy-4-(N-3-fluoro-3-methyl-n-butyl-2-amine)-3-cyclobutene-1,2-dione as a white solid: $^1$H NMR (CDCl$_3$) δ6.21 (br, 1H), 4.77 (br m, 2H), 3.80 (br, 1H), 1.47 (t, 3H,), 1.43 (d, 3H), 1.36 (d, 3H), 1.32 (d, 3H) ppm.

Step 6) 3-Chloro-4-{[2-(2-fluoro-1,2-dimethyl-propylamino)-3,4-dioxo-cyclobut-1-enylamino]-methyl)-benzonitrile To a solution of 3-ethoxy-4-(N-3-fluoro-3-methyl-n-butyl-2-amine)-3-cyclobutene-1,2-dione (0.573 g, 2.5 mmole) in dry tetrahydrofuran(8 mL) was added 2-chloro-4-cyanobenzylamine (0.458 g, 2.75 mmole). The mixture was heated to 70° C. under a nitrogen atmosphere for 18 hours. The mixture was cooled to room temperature with stirring and vacuum filtered through a fritted glass filter. The solid was washed well with several portions of an ethanol/diethyl ether (1/1) solvent mixture. The solid was air dried then heated to 77° C. under high vacuum for 16 hours. This afforded 0.49 g of the title compound as a white solid: $^1$H NMR (DMSO-d$_6$) δ8.10 (d, 1H), 7.88 (dd, 1H), 7.75 (br, 1H), 7.60 (d, 1H), 7.60 (br, 1H), 4.87 (m, 2H), 4.17 (br, 1H), 1.35 (s, 3H), 1.29 (s, 3H), 1.20 (d, 3H) ppm. IR (KBr): 2220, 1850 cm$^{-1}$; MS (m/z) 350 (|M+H|$^+$).

EXAMPLE 76

3-Chloro-4-}|2-(1,1-dimethyl-propylamino)-3,4-dioxo-cyclobut-1-enylamino|-methyl}-benzonitrile Tetrahydrofuran (10 mL), 3-butoxy-4-(1,1-dimethylpropylamino)-cyclobut-3-ene-1,2-dione (0.957 g, 4 mmol, Example 3) and 2-chloro-4-cyanobenzylamine (0.666 g, 4 mmol, Example 2, Step 3) were stirred together at room temperature for 138 hours. Removal of solvent, through trituration of the residue with diethyl ether and drying provided a white solid. Recrystallization of this solid from acetonitrile (charcoal) followed by a second recrystallization from acetonitrile gave 0.863 g of title compound as a white solid: mp 215.5°–219.5° C. (softens 212.5° C.); $^1$H NMR (DMSO-d$_6$) δ8.11 (d, 1H), 7.89 (m, 1H), 7.86 (m, 1H), 7.61 (d, 1H), 7.53 (s, 1H), 4.90 (d, 2H), 1.68 (q, 2H), 1.30 (s, 6H), 0.82 (t, 3H) ppm. IR (KBr): 3300, 2230, 1790, 1660 cm$^{-1}$; MS (m/z) 331/333 (M$^+$). HPLC indicates a major component (99.6%).

Elemental analysis for C$_{12}$H$_{18}$ClN$_3$O$_2$ Calc'd: C, 61.54; H, 5.47; N, 12.66. Found: C, 60.81; H, 5.40; N, 12.52. C, 60.81; H, 5.35; N, 12.86.

EXAMPLE 77

N-(2-Chloro-4-cyano-benzyl)-N-|2-(1,1-dimethyl-propylamino)-3,4-dioxo-cyclobut-1-enyl)-acetamide A solution of 3-chloro-4-{|2-(1,1-dimethyl-propylamino)-3,4-dioxo-cyclobut-1-enylamino|-methyl}-benzonitrile (0.829 g, 2.50 mmol, Example 76) in tetrahydrofuran (10 mL) and N,N-dimethylformamide (5 mL) was treated with sodium hydride (0.066 g, 2.75 mmol) and stirring was continued for 15 minutes. Acetic anhydride (0.281 g, 2.75 mmol) was added. After stirring 40 minutes at room temperature, solvent was removed and the residue was partitioned between ethyl acetate and brine, and the brine fraction was extracted with ethyl acetate. The combined ethyl acetate fractions were washed with dilute, aqueous sodium carbonate solution, with brine and dried (anhydrous sodium sulfate). Removal of solvent gave a yellow solid that was chromatographed (gravity, chloroform) on silica. The appropriate fractions were freed of solvent and the foamy residue was solidified by addition-rotoevaporation of hexane (twice). Recrystallization (twice) of the solid from acetone-hexane gave 513 mg of the title compound as a white solid: mp 150.5°–151.0° C. (softens 149.5° C.); $^1$H NMR (DMSO-d$_6$) δ7.90–9.22 (broad hump, 1H), 8.10 (s, 1H), 7.84 (m, 1H), 7.51 (d, 1H), 5.29 (br s, 2H), 2.16 (s, 3H), 1.71 (q, 2H), 1.35 (s, 6H), 0.85 (t, 3H) ppm. IR (KBr): 3300, 3080, 2230, 1790, 1720, 1680 cm$^{-1}$. MS (m/z) 373/375 (M$^+$). HPLC indicates a major component (>99%).

Elemental analysis for C$_{19}$H$_{20}$ClN$_3$O$_3$ Calc'd: C, 61.04; H, 5.39; N, 11.24. Found: C, 60.67; H, 5.26; N, 11.17.

EXAMPLE 78

N-(2-Chloro-4-cyano-benzyl-N-|2-(1,1-dimethyl-propylamino)-3,4-dioxo-cyclobut-1-enyl|-butylamine Employing the procedure of Example 77, 3-chloro-4-{|2-(1,1-dimethyl-propylamino)-3,4-dioxo-cyclobut-1-enylamino|-methyl}-benzonitrile (0.929 g, 2.80 mmol, Example 76) was reacted with sodium hydride (0.074 g, 3.08 mmol) and then with butyric anhydride (0.487 gm 3.08 mmol) to yield, after chromatographic purification (gravity, chloroform) on silica, 928 mg of a pale yellow solid. Two recrystallizations of the crude product from diisopropyl ether afforded 0.646 g of the title compound as a white solid: mp 105.5°–111.0° C. (softens 104.0° C.). MS (m/z) 402 |M+H|$^+$.

Elemental analysis for C$_{21}$H$_{24}$ClN$_3$O$_3$ Calc'd: C, 62.76; H, 6.02; N, 10.46. Found: C, 62.56; H, 5.65, N, 10.46.

EXAMPLE 79

3-(2,4-Dimethyl-benzylamino)-4-(1,1-dimethyl-propylamino)-cyclobut-3-ene-1,2-dione Employing a procedure similar to that of Example 8, 3-butoxy-4-(1,1-dimethyl-propylamino)-cyclobut-3-ene-1,2-dione (1.20 g, 5 mmol, Example 3) and 2,4-dimethylbenzylamine (0.68 g, 5.0 mmol, a mixture of 2,4- and 2,6-dimethylbenzylamine isomers) in tetrahydrofuran (8 mL) was reacted to give 1.09 g of a cream-colored solid. Three recrystallizations of this material gave 0.677 g of a white solid. A 0.496 g portion of this solid was purified by HPLC and the solid isolated from the appropriate eluates was recrystallized from acetonitrile to yield 0.278 g of the title compound as a white solid: mp 177°–178° C. (softens 160° C.); $^1$H NMR (DMSO-d$_6$) δ7.61 (br m, 1H), 7.35 (br s, 1H), 7.17 (d, 1H), 7.03 (s, 1H), 7.00 (m, 1H), 4.70 (d, 2H), 2.27 (s, 3H), 2.25 (s, 3H), 1.65 (q, 2H), 1.29 (s, 6H), 0.80 (t, 3H) ppm. IR (KBr): 3210, 1790, 1640 cm$^{-1}$. M (m/z) 300 (M$^+$). HPLC indicates a major component (99.1%).

Elemental analysis for C$_{18}$H$_{24}$N$_2$O$_2$ Calc'd: C, 71.97; H, 8.05; N, 9.32. Found: C, 71.87; H, 7.99; N, 9.32.

EXAMPLE 80

3-(2,3-Dimethyl-benzylamino)-4-(1,1-dimethyl-propylamino)-cyclobut-3-ene-1,2-dione Tetrahydrofuran (15 mL), 3-butoxy-4-(1,1-dimethyl-propylamino)-cyclobut-3-ene-1,2-dione (1.20 g, 5 mmol), 2,3-dimethylbenzylamine hydrochloride (0.858 g, 5 mmol, prepared according to the procedure of R. Fuller et al., J. Med. Chem., 16 (2), 101 (1973)) and triethylamine (0.506 g, 5 mmol) were refluxed 22.5 hours and then processed in a manner similar to that of Example 4, Step 3, to provide 1.337 g of crude product. Recrystallization (twice) of this material from methanol afforded 0.777 g of the title compound as a white solid: mp 196°–198° C. MS (m/z) 300 (M$^+$).

Elemental analysis for C$_{18}$H$_{24}$N$_2$O$_2$ Calc'd: C, 71.97; H, 8.05; N, 9.33. Found: C, 71.80; H, 8.23; N, 9.23.

EXAMPLE 81

3-(1,1-Dimethyl-propylamino)-4-(2,4,6-trimethyl-benzylamino)-cyclobut-3-ene-1,2-dione Tetrahydrofuran (15 mL), 3-butoxy-4-(1,1-dimethyl-propylamino)-cyclobut-3-ene-1,2-dione (1.20 g, 5 mmol), 2,4,6-trimethylbenzylamine hydrochloride (0.928 g, 5 mmol, Example 9, Step 2) and triethylamine (0.506 g, 5 mmol) were stirred together at room temperature for 3 days. The mixture was then prepared as in Example 9, Step 3. Three recrystallization of the crude product from acetonitrile provided 0.664 g of the title compound as a white solid: mp 284°–5° C. (dec) (softens 282° C.). MS (m/z) 314 (M$^+$).

Elemental analysis for C$_{19}$H$_{26}$N$_2$O$_2$ Calc'd: C, 72.58; H, 8.33; N, 8.91. Found: C, 72.61; H, 8.46; N, 9.01.

EXAMPLE 82

3-tert-Butylamino-4-(2,5-dichloro-benzylamino)-cyclobut-3-ene-1,2-dione

Employing the procedure of Example 2, Step 4, and a reaction period of 23 hours, 2,5-dichlorobenzylamine (0.88 g, 5 mmol) and 3-butoxy-4-tert-butylamino-cyclobut-3-ene-1,2-dione (1, 13 g, 5 mmol) in tetrahydrofuran (15 mL) were converted to 1.52 g of a cream-colored solid. Recrystallization of this material from acetonitrile (twice) and from methanol provided 0.853 g of the tide compound as a white solid: mp 236° C. (softens 216° C.). MS (m/z) 326/328/330 (M$^+$).

Elemental analysis for $C_{15}H_{16}Cl_2N_2O_2$ Calc'd: C, 55.06; H, 4.93; N, 8.56. Found: C, 55.29; H, 4.76; N, 8.55.

EXAMPLE 83

3-(2,5-Dichloro-benzylamino)-4-(1,1-dimethyl-propylamino)-cyclobut-3-ene-1,2-dione Tetrahydrofuran (13 mL), 3-butoxy-4-(1,1-dimethyl-propylamino)-cyclobut-3-ene-1,2-dione (1.20 g, 5 mmol) and 2,5-dichlorobenzylamine (0.88 g, 5 mmol) were stirred together for approximately 64.5 hours. Removal of solvent and thorough trituration of the residue with diethyl ether gave 1.51 g of a light yellow solid. As purification of this material by three recrystallizations from acetonitrile was unrewarding, the recovered crude product was subjected to HPLC. The solid isolated from the appropriate fractions was recrystallized from acetonitrile to afford 0.598 g of the title compound as a white solid: mp 195°–196° C. MS (m/z) 340/342/344 (M$^+$). HPLC indicates a major component (>99%).

Elemental analysis for $C_{16}H_{18}Cl_2N_2O_2$ Calc'd: C, 56.32; H, 5.32; N, 8.21. Found: C, 56.31; H, 5.26; N, 8.22.

EXAMPLE 84

3-tert-Butylamino-4-(3,4-dimethyl-benzylamino)-cyclobut-3-ene-1,2-dione

Tetrahydrofuran (17 mL), 3-butoxy-4-tert-butylamino-cyclobut-3-ene-1,2-dione (1.13 g, 5 mmol, Example 1) and 3,4-dimethylbenzylamine (0.68 g, 5 mmol) were stirred together at room temperature for 2 days. Removal of solvent and trituration of the residue with diethyl ether gave 1.06 g of a light yellow solid. Four recrystallizations of this material from acetonitrile provided 0.394 g of the tide compound as a white solid: mp 264°–264° C. (softens 260° C.). MS (m/z) 286 (M$^+$). HPLC indicates a major component (96%).

Elemental analysis for $C_{17}H_{22}N_2O_2$ Calc'd: C, 71.30; N, 7.74; N, 9.78. Found: C, 71.28; H, 7.71; N, 9.61.

EXAMPLE 85

3-(3,4-Dimethyl-benzylamino)-4-(1,1-dimethyl-propylamino)-cyclobut-3-ene-1,2-dione Tetrahydrofuran (12 mL), 3-butoxy-4-(1,1-dimethyl-propylamino)-cyclobut-3-ene-1,2-dione (1.20 g, 5 mmol), and 3,4-dimethylbenzylamine (0.68 g, 5 mmol) were stirred together at room temperature for 17 hours. Removal of solvent and trituration of the residue with diethyl ether provided 1.04 g of a cream-colored solid. Recrystallization of the crude product from acetonitrile (twice) and from methanol (twice) gave 0.45 g of the title compound as a fluffy, white soid: mp 248° C. (softens 246° C.). MS (m/z) 300 (M$^+$). HPLC indicates a major component (97%).

Elemental analysis for $C_{18}H_{24}N_2O_2$ Calc'd: C, 71.97; H, 8.05; N, 9.33. Found: C, 71.91; H, 8.13; N, 9.37.

EXAMPLE 86

3-tert-Butylamino-4-(3,5-dimethyl-benzylamino)-cyclobut-3-ene-1,2-dione

Step 1) Preparation of 3,5-dimethylbenzylamine hydrochloride

The reduction of 3,5-dimethylbenzonitrile with diborane was conducted according to the procedure of R. Fuller et al., J. Med. Chem., 16 (2), 101 (1973), and the amine was converted to the hydrochloride salt with isopropanolic HCl. Recrystallization of the crude salt from methanol-acetonitrile in the presence of several drops of isopropanolic HCl, provided the title compound as a white solid: mp 251°–255° C. MS (m/z) 135 (M$^+$, base).

M. Konawalow, Chem. Ber., 28, 1852 (1895) reported mp 245°–246° C. (dec) for this hydrochloride.

Step 2) 3-tert-Butylamino-4-(3,5-dimethyl-benzylamino)-cyclobut-3-ene-1,2-dione

The product from Example 86, Step 1 (0.858 g, 5 mmol), 3-butoxy-4-tert-butylamino-cyclobut-3-ene-1,2-dione (1.13 g, 5 mmol, Example 1), triethylamine (0.506 g, 5 mmol), and tetrahydrofuran (15 mL) were refluxed 17 hours and then a processed in a manner similar to that of Example 4, Step 3 to give 0.833 g of crude product. Recrystallization (twice) of this material from methanol gave 0.715 g of the title compound as a white solid: mp 246°–248° C. MS (m/z) 286 (M$^+$).

Elemental analysis for $C_{17}H_{22}N_2O_2$ Calc'd: C, 71.30; H, 7.74; N, 9.78. Found: C, 71.23; H, 7.79; N, 9.81.

EXAMPLE 87

3-(3,5-Dimethyl-benzylamino)-4-(1,1-dimethyl-propylamino)-cyclobut-3-ene-1,2-dione The product from Example 86, Step 1 (0.858 g, 5 mmol), triethylamine (0.506 g, 5 mmol), 3-butoxy-4-(1,1-dimethyl-propylamino)-cyclobut-3-ene-1,2-dione (1.20 g, 5 mmol, Example 3), and tetrahydrofuran was refluxed approximately 19 hours in a manner similar to that of Example 4, Step 3. The crude product was recrystallized (twice) from methanol to yield 0.81 g of the tide compound as a white solid: mp 221.5°–224° C. MS (m/z) 300 (M$^+$).

Elemental analysis for $C_{18}H_{24}N_2O_2$ Calc'd: C, 71.97; H, 8.05; N, 9.33. Found: C, 71.60; H, 7.95; N, 9.31.

EXAMPLE 88

3-(3,5-Dichloro-benzylamino)-4-(1,1-dimethyl-propylamino)-cyclobut-3-ene-1,2-dione A solution of 3-butoxy-4-(1,1-dimethyl-propylamino)-cyclobut-3-ene-1,2-dione (1.20 g, 5 mmol, Example 3), 3,5-dichlorobenzylamine (0.88 g, 5 mmol) and tetrahydrofuran (15 mL) was stirred at room temperature for 3 days. The reaction mixture was processed as in Example 2, Step 4. The crude product was recrystallized (twice) from methanol to provide 1.309 g of the title compound as a white solid: mp 257°–258° C. (dec). MS (m/z) 340/342/344 (M$^+$). HPLC indicates a major component (97%).

Elemental analysis for $C_{16}H_{18}Cl_2N_2O_2$ Calc'd: C, 56.32; H, 5.32; N, 8.21. Found: C, 56.26; H, 5.13; N, 8.06.

EXAMPLE 89

3-tert-Butylamino-4-(3,5-dichloro-benzylamino)-cyclobut-3-ene-1,2-dione

A mixture of 3-butoxy-4-tert-butylamino-cyclobut-3-ene-1,2-dione (1.13 g, 5 mmol, Example 1), 3,5- dichlorobenzylamine (0.88 g, 5 mmol) and tetrahydrofuran (15 mL) was stirred at room temperature overnight, and then was processed as in Example 2, Step 4. Recrystallization (twice) of the crude product from methanol gave 1.095 g of the title compound as a whte solid: mp 281°–283° C. (dec). MS (m/z) 326/328/330 (M$^+$). HPLC indicates a major component (99.2%).

Elemental analysis for $C_{15}H_{16}Cl_2N_6O_2$ Calc'd: C, 55.06; H, 4.93; N, 8.56. Found: C, 55.01; H, 4.77; N, 8.57.

EXAMPLE 90

3-tert-Butylamino-4-(3-chloro-4-methyl-benzylamino)-cyclobut-3-ene-1,2-dione Step 1) Preparation of 3-Chloro-4-methylbenzylamine hydrochloride The reduction of 3-chloro-4-methylbenzonitrile with diborane was conducted according to the procedure of R. Fuller et al., J. Med. Chem., 16 (2), 101 (1973), and the amine was converted to the hydrochloride salt with isopropanolic HCl. Recrystallization of the crude salt from ethanol, in the presence of a small amount of isopropanolic HCl, gave the title compound as a white solid: mp 260°–264° C. (softens 254° C.). MS (m/z) 155/157 (M$^+$ base).

Step 2) 3-tert-Butylamino-4-(3-chloro-4-methyl-benzylamino)-cyclobut-3-ene-1,3-dione.

The product from Example 90, Step 1 (0.96 g, 5 mmol), 3-butoxy-4-tert-butylamino-cyclobut-3-ene-1,2-dione (1.12 g, 5 mmol, Example 1), triethylamine (0.506 g, 5 mmol), and tetrahydrofuran (25 mL) were refluxed overnight and then was processed in a manner similar to that of Example 4, Step 3. The crude product (1.221 g) was recrystallized (twice) from ethanol to yield 1.06 g of the title compound as a white solid: mp 291°–292° C. (dec). MS (m/z) 306/308 (M$^+$).

Elemental analysis for $C_{16}H_{19}ClN_2O_2$ Calc'd: C, 62.64; H, 6.24; N, 9.13. Found: C, 62.30; H, 6.38; N, 9.04.

EXAMPLE 91

3-(3-Chloro-4-methyl-benzylamino)-4-(1,1-dimethyl-propylamino)-cyclobut-3-ene-1,2-dione The product from Example 90, Step 1 (0.96 g, 5 mmol), 3-butoxy-4-(1,1-dimethyl-propylamino)-cyclobut-3-ene-1,2-dione (1.20 g, 5 mmol, Example 3), triethylamine (0.56 g, 5 mmol), and tetrahydrofuran (15 mL) were refluxed for approximately 22 hours. Processing the reaction mixture in a manner similar to that of Example 4, Step 3 afforded 1.234 g of a white solid. Recrystallization (twice) of the crude product from methanol provided 0.963 g of the title compound as a white solid: mp 261°–263° C. MS (m/z) 320/322 (M$^+$).

Elemental analysis for $C_{17}H_{21}ClN_2O_2$ Calc'd: C, 63.65; H, 6.60; N, 8.73. Found: C, 63.67; H, 6.63; N, 8.70.

EXAMPLE 92

4-[(2-Butoxy-3,4-dioxo-cyclobut-1-enylamino)-methyl]-3-chloro-benzonitrile

A solution of 3,4-dibutoxy-3-cyclobutene-1,2-dione (2.263 g, 10 mmol) and 2-chloro-4-cyanobenzylamine (1.666 g, 10 mmol, Example 2, Step 3) in tetrahydrofuran (25 mL) was stirred at room temperature for 22 hours. The residue remaining after removal of solvent was dissolved in chloroform and was chromatographed (flash, ethyl acetate/hexane) on silica. The solid isolated from the appropriate fractions was recrystallized from ethyl acetate to provide 2.427 g of a white solid: mp 147.5°–149° C. MS (m/z) 318 (M$^+$). HPLC indicates a major component (>99%).

Elemental analysis for $C_{16}H_{15}ClN_2O_3$ Calc'd: C, 60.29; H, 4.74; N, 8.79. Found: C, 60.05; H, 4.54; N, 8.69.

EXAMPLE 93

3-Chloro-4-{[2-(2-hydroxy-1,1-dimethyl-ethylamino)-3,4-dioxo-cyclobut-1-enylamino]-methyl}-benzonitrile Step 1) Preparation of 3-butoxy-4-(2-hydroxy-1,1-dimethyl-ethylamino)-cyclobut-3-ene-1,2-dione With ice-bath cooling, a solution of 3,4-dibutoxy-3-cyclobutene-1,2-dione (4.526 g, 20 mmol) in tetrahydrofuran (35 mL) was stirred and treated dropwise with a solution of 2-amino-2-methylpropanol (1.783 g, 20 mmol) in tetrahydrofuran (20 mL). The solution then was stirred at room temperature overnight. The brown oil isolated after removal of solvent was chromatoraphed (flash, ethyl acetate/hexane) on silica. The appropriate fractions were freed of solvent and the residue dried to give 4.122 g of the title compound as a colorless oil: $^1$H NMR (DMSO-d$_6$) δ8.43 and 8.33 (two m, 1H, rotamers), 4.90 (t, 1H), 4.65 (m, 2H), 3.37 (m, 2H), 1.72 (m, 2H), 1.39 (m, 2H), 1.23 (m, 6H), 0.91 (t, 3H) ppm. IR (film): 3440, 3250, 1790, 1690 cm$^{-1}$. MS (m/z) 242 ([M+H]$^+$).

Step 2) 3-Chloro-4-{[2-(2-hydroxy-1,1-dimethyl-ethylamino)-3,4-dioxo-cyclobut-1-enylamino)-methyl}-benzonitrile Tetrahydrofuran (10 mL), the product from Example 93, Step 1 (1.031 g, 5 mmol), and 2-chloro-4-cyanobenzylamine (0.833 g, 5 mmol, Example 2, Step 3) were stirred together at room temperature for approximately 67 hours. Removal of solvent and trituration of the residue with diethyl eher gave 1.18 g of a white solid. mp 220°–223° C.; $^1$H NMR (DMSO-d$_6$) δ8.11 (d, 1H), 7.99 (t, 1H), 7.88 (m, 1H), 7.62 (d, 1H), 7.58 (s, 1H), 5.10 (t, 1H), 4.86 (d, 2H), 3.40 (d, 2H), 1.28 (s, 6H) ppm. IR (Kbr): 3320, 3200, 2240, 1790, 1665 cm$^{-1}$; MS (m/z) 334 ([M+H]$^+$).

Elemental analysis for $C_{16}H_{16}ClN_3O_3$ Calc'd: C, 57.58; H, 4.83; N, 12.59. Found: C, 57.51; H, 4.71; N, 12.74.

EXAMPLE 94

3-(2,5-Dimethyl-benzylamino)-4-(1,1-dimethyl-propylamino)-cyclobut-3-ene-1,2-dione Step 1) Preparation of N-(2,5-dimethylbenzyl) phthalimide N,N-Dimethylformamide (200 mL), 2,5-dimethylbenzyl chloride (15.5 g, 0.10 mol), and potassium phthalimide (20.38 g, 0.11 mol) were stirred together for 140 minutes. During this period, the reaction temperature rose from 22° C. to 31° C. and then receded to 27° C. Following removal of solvent in vacuo, the residue was thoroughly triturated with water and dried to give 25.69 g of a white solid. This solid was recrystallized from ethyl acetate and, prior to drying, a 0.99 g portion (wet weight) was further recrystallized from ethyl acetate to provide 0.68 g of N-(2,5-dimethylbenzyl)phthalimide as a white solid: mp 148°–150° C. (softens 145° C.). MS (m/z) 265 (M$^+$).

Elemental analysis for $C_{17}H_{15}NO_2$ Calc'd: C, 76.96; H, 5.70; N, 5.28. Found: C, 76.87; H, 5.57; N, 5.29.

The amount of dried, once recrystallized N-(2,5-dimethylbenzyl)phthalimide, also exhibiting mp 148°–150° C. (softens 145° C.), was 22.75 g.

41

Step 2) Preparation of 2.5-dimethylbenzylamine hydrochloride

With mechanical stirring N-(2.5-dimethylphthalimide (22.67 g, 85.5 mmol, Example 94, Step 1), hydrazine hydrate (8.6 g, 170 mmol), and absolute ethanol (200 mL) were refluxed for one hour. After cooling to room temperature, the stirred mixture was treated carefully with 2N hydrochloric acid (123 mL) and stirred forty minutes longer. The mixture was filtered and the insolubles were rinsed with ethanol and with water. Removal of solvent from the combined filtrate and rinsings gave a residue that was treated with ice-water (300 mL). The mixture was basified with 2.5 N sodium hydroxide (123 mL) and then was extracted with chloroform. The combined extracts were washed successively with 1N sodium hydroxide, with water, with brine, and then were dried (anhydrous sodium sulfate).

The brownish-yellow oil remaining after removal of solvent was dissolved in diethyl ether and treated with isopropanolc hydrogen chloride. The solid was collected, rinsed with diethyl ether and dried to yield 12.05 g of an off-white solid.

The crude salt was recrystallized from absolute ethanol and, prior to drying, a 1 g (wet weight) portion was further recrystallized from absolute ethanol to afford 0.464 g of 2.5-dimethylbenzylamine hydrochloride as a white solid: mp 234° C. (softens 231° C.).

Elemental analysis for $C_9H_{13}N \cdot HCl$ Calc'd: C, 62.97; H, 8.22; N, 8.16. Found: C, 63.06; H, 8.28; N, 8.06.

The yield of dried, once recrystallized 2.5-dimethylbenzylamine hydrochloride, mp 234° C. (softens 230° C.) was 5.66 g (H. Mix, et al., Z. Physiol. Chem., 343, 52 (1965) reported mp 233° C. for 2.5-dimethylbenzylamine hydrochloride).

Step 3) 3-(2.5-Dimethylbenzylamino)-4-(1,1-dimethyl-propylamino)-cyclobut-3-ene-1,2-dione Tetrahydrofuran (10 mL), 2,5-dimethylbenzylamine hydrochloride (0.858 g, 5.0 mmol, Example 94, Step 2), triethylamine (0.51 g, 5.0 mmol), and 3-butoxy-4-(1,1-dimethylpropylamino)-cyclobut-3-ene-1,2-dione (1.20 g, 5.0 mmol, Example 3) were stirred together at room temperature for approximately 18 hours. After removal of solvent the residue was triturated with water, with diethyl ether, and dried to give 1.31 g of a light yellow solid. Three recrystallizations of the crude product from acetonitrile provided 0.812 g of the title compound as a fluffy, white solid: mp 199°–200° C. (softens 195° C.). MS (m/z) 301 (|M+H|⁺). HPLC indicates a major component (>99%).

Elemental analysis for $C_{18}H_{24}N_2O_2$ Calc'd: C, 71.97; H, 8.05; N, 9.33. Found: C, 71.89; H, 8.01; N, 9.30.

EXAMPLE 95

3-(t-Butylamino)-4-(2.5-dimethyl-benzylamino)-cyclobut-3-ene-1,2-dione

Tetrahydrofuran (10 mL), 3-butoxy-4-tert-butylamino-cyclobut-3-ene-1,2-dione (1.13 g, 5.0 mmol, Example 1), 2.5-dimethylbenzylamine (0.858 g, 5.0 mmol), and triethylamine (0.51 g, 5.0 mmol) were stirred together at room temperature for approximately 18 hours. Following removal of solvent, the residue was triturated with water, with diethyl ether, and dried to give 0.698 g of a cream-colored solid. Three recrystallizations of this material from methanol afforded 0.444 g of the title compound as a white solid: mp 246°–247° C. (softens 242° C.). MS (m/z) 287 (|M+H|⁺). HPLC indicates a major component (>99%).

42

Elemental analysis for $C_{17}H_{22}N_2O_2$ Calc'd: C, 71.30; H, 7.74; N, 9.78. Found: C, 71.34; H, 7.76; N, 9.77.

EXAMPLE 96

3-tert-Butylamino-4-(3-chloro-2-methyl-benzylamino)-cyclobut-3-ene-1,2-dione

Step 1) Preparation of 3-Chloro-2-methylbenzylamine hydrochloride

A solution of 3-chloro-2-methylbenzonitrile (7.58 g, 50 mmol) in tetrahydrofuran (50 mL) was added slowly with stirring to 1.0M borane-tetrahydrofuran complex (150 mL, 150 mmol) and the mixture was refluxed for 21 hours. With cooling (ice-water bath) and stirring 2N hydrochloric acid (50 mL) was added cautiously and stirring was continued for 40 minutes longer. The reaction mixture was freed of solvent and the residue was partitioned between water and chloroform. As both phases contained solids, they were filtered. The aqueous filtrate was basified with dilute aqueous sodium hydroxide and was extracted with diethyl ether. The extracts were washed with water, with brine, dried (anhydrous sodium sulfate), and concentrated to give 3.21 g of the crude amine.

The solids collected from the original aqueous acidic and chloroform fractions were partially dissolved in water. The mixture was basified with dilute aqueous sodium hydroxide and were extracted thoroughly with diethyl ether. After drying (anhydrous sodium sulfate), the extracts were concentrated to give an additional 2.23 g of crude amine.

Dissolution of the two lots of crude amine in diethyl ether, and addition of isopropanolic hydrogen chloride gave a solid that was rinsed with diethyl ether and dried to yield 5.57 g of a light beige salt.

The crude salt was recrystallized from absolute ethanol in the presence of a small amount of isopropanolic hydrogen chloride. Prior to drying, a 0.98 g (wet weight) portion was recrystallized in the same manner and dried to afford 0.63 g of 3-chloro-2-methylbenzylamine hydrochloride as a white solid: mp 265°–266° C. (softens 263° C.). MS (m/z) 155/157 (|M+H|⁺).

Elemental analysis for $C_8H_{10}ClN \cdot HCl$ Calc'd: C, 50.02; H, 5.77; N, 7.29. Found: C, 49.86; H, 5.75; N, 7.23.

The amount of dried, once recrystallized 3-chloro-2-methylbenzylamine hydrochloride, mp 266°–267° C. (softens 263° C.) obtained was 3.76 g.

Step 2) 3-tert-Butylamino-4-(3-chloro-2-methyl-benzylamino)-cyclobut-3-ene-1,2-dione Tetrahydrofuran (10 mL), 3-chloro-2-methylbenzylamine hydrochloride (0.96 g, 5.0 mmol, Example 96, Step 1), triethylamine (0.51 g, 5.0 mmol), and 3-butoxy-4-tert-butylamino-cyclobut-3-ene-1,2-dione (1.13 g, 5.0 mmol) were stirred together at room temperature for 18.5 hours. The residue remaining after removal of solvent was triturated with water, with diethyl ether, and was dried to give 1.11 g of a cream-colored solid. Three recrystallizations of this material from acetonitrile provided 0.80 g of the title compound as a white, fluffy solid: mp 258°–259° C. (dec) (softens 242° C.). MS (m/z) 307 (|M+H|⁺). HPLC indicates a major component (>99%).

Elemental analysis for $C_{16}H_{19}ClN_2O_2$ Calc'd: C, 62.64; H, 6.24; N, 9.13. Found: C, 62.80; H, 6.18; N, 9.11.

EXAMPLE 97

3-(3-Chloro-2-methyl-benzylamino)-4-(1,1-dimethyl-propylamino)-cyclobut-3-ene-1,2-dione Tetrahydrofuran (10 mL), 3-butoxy-4-(1,1-dimethyl-propylamino)-cyclobut-3-ene-1,2-dione (1.20 g, 5.0 mmol, Example 3), 3-chloro-2-methylbenzylamine hydrochloride (0.96 g, 5.0 mmol, Example 96, Step 1), and triethylamine (0.51 g, 5.0 mmol) were stirred together at room temperature for 65 hours. Processing the reaction mixture as in Example 96, Step 2 provided 1.44 g of a white solid. Two recrystallizations of the crude product from methanol gave 1.12 g of the title compound as a fluffy, white solid: mp 236°–237° C. (softens 233° C.). MS (m/z) 321/323 (|M+H|$^+$). HPLC indicates a major component (99.6%).

Elemental analysis for $C_{17}H_{21}ClN_2O_2$ Calc'd: C, 63.65; H, 6.60; N, 8.73. Found: C, 63.63; H, 6.59; N, 8.78.

EXAMPLE 98

N-(2-tert-Butylamino-3,4-dioxo-cyclobut-1-enyl)-N-(2-chloro-4-cyano-benzyl)-acetamide Employing the procedure of Example 77, 4-|(tert-butylamino-3,4-dioxo-cyclobut-1-enylamino)-methyl|-3-chlorobenzonitrile (0.731 g, 2.30 mmol), sodium hydride (0.062 g, 2.6 mmol), and acetic anhydride (0.27 g, 2.6 mmol) were reacted in tetrahydrofuran (10 mL) and N,N-dimethylformamide (5 mL) to provide 0.592 g of a yellow solid. This material was chromatographed (flash, chloroform) on silica and the appropriate fractions were concentrated. The residue was solidified by addition-rotoevaporation of hexane (twice) and dried to give 0.353 g of crude product. Recrystallization (twice) of this material from dichloromethane-hexane afforded 0.125 g of the title compound as a pale yellow solid: mp 184°–185° C. (softens 181° C.); $^1$H NMR (DMSO-d$_6$) δ9.10–8.15 (broad hump, 1H), 8.10 (s 1H), 7.84 (m, 1H), 7.50 (d, 1H), 5.27 (br s, 2H), 2.16 (s, 3H), 1.40 (s, 9H) ppm. IR (KBr): 3270, 2230, 1780, 1720, 1680 cm$^{-1}$; MS (m/z) 359/361 (M$^+$). HPLC indicates a major component (>99.9%).

Elemental analysis for $C_{18}H_{18}ClN_3O_3$ Calc'd: C, 60.09; H, 5.04; N, 11.68. Found: C, 59.61; H, 4.72; N, 11.51. C, 59.93; H, 4.86; N, 11.50.

EXAMPLE 99

3-(2,3-Dichloro-benzylamino)-4-(1,1-dimethyl-propylamino)-cyclobut-3-ene-1,2-dione Tetrahydrofuran (12 mL), 3-butoxy-4-(1,1-dimethyl-propylamino)-cyclobut-3-ene-1,2-dione (1.20 g, 5.0 mmol) and 2,3-dichlorobenzylamine (0.88 g, 5.0 mmol) were stirred together at room temperature for 64 hours. The residue remaining after removal of solvent was trituated thoroughly with diethyl ether and dried to give 1.55 g of a white solid. Recrystallization (four times) of the crude product from acetonitrile provided 0.796 g of the title compound as a white solid: mp 222°–223° C. (softens 218° C.). MS (m/z) 340/342/344 (M$^+$). HPLC indicates a major component (96.2%).

Elemental analysis for $C_{16}H_{18}Cl_2N_2O_2$ Calc: C, 56.32; H, 5.32; N, 8.21. Found: C, 56.39; H, 5.28; N, 8.18.

EXAMPLE 100

3-(t-Butylamino)-4-(2,3-dichloro-benzylamino)-cyclobut-3-ene-1,2-dione

Tetrahydrofuran (12 mL), 3-butoxy-4-tert-butylamino-cyclobut-3-ene-1,2-dione (1.13 g, 5.0 mmol, Example 1), and 2,3-dichlorobenzylamine (0.88 g, 5.0 mmol) were stirred together at room temperature for 64 hours. After removal of solvent, trituation of the residue with diethyl ether and drying gave 1.46 g of a white solid. Four recrystallizations of this crude product from acetonitrile provided 0.927 g of the title compound as a white solid: mp 237°–243° C. (dec). MS (m/z) 327 (|M+H|$^+$).

Elemental analysis for $C_{15}H_{16}Cl_2N_2O_2$ Calc'd: C, 55.06; H, 4.93; N, 8.56. Found: C, 54.77; H, 4.81; N, 8.51.

EXAMPLE 101

N-(2-tert-Butylamino-3,4-dioxo-cyclobut-1-enyl)-N-(2-chloro-4-cyano-benzyl)-butylamine Employing the procedure of Example 77, 4-|(tert-butylamino-3,4-dioxo-cyclobut-1-enylamino)-methyl|-3-chlorobenzonitrile (0.887 g, 2.79 mmol), sodium hydride (0.076 g, 3.07 mmol), and butyric anhydride (0.486 g, 3.07 mmol) were reacted in tetrahydrofuran (10 mL) and N,N-dimethylformamide (5 mL) to provide 0.996 g of a golden yellow solid. This material was dissolved in chloroform and was chromatographed (flash, ethyl acetate-hexane) on silica and the appropriate fractions were concentrated. The residue was solidified by addition-rotoevaporation of hexane (twice). Recrystallization (twice) of the solid from t-butyl methyl ether provided 0.539 g of the title compound as a white solid: mp 133°–134° C. (softens 131° C.). MS (m/z) 388/390 (|M+H|$^+$).

Elemental analysis for $C_{20}H_{22}ClN_3O_3$ Calc'd: C, 61.93; H, 5.72; N, 10.83. Found: C, 61.59; H, 5.50; N, 10.68.

The smooth muscle relaxing activity of the compounds of this invention was established in accordance with standard pharmaceutically accepted test procedures with representative compounds as follows:

Sprague-Dawley rats (150–200 g) are rendered unconscious by $CO_2$ asphyxiation and then euthanized by cervical dislocation. The bladder is removed into warm (37 deg.C) physiological salt solution (PSS) of the following composition (mM): NaCl, 118.4; KCl, 4.7; $CaCl_2$, 2.5; $MgSO_4$, 4.7; $H_2O$, 1.2; $NaHCO_3$, 24.9; $KH_2PO_4$, 1.2; glucose, 11.1; EDTA, 0.023; gassed with 95% $O_2$; 2/5% $CO_2$; pH 7.4. The bladder is opened and then dut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity ($IC_{50}$ concentration) and is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips

| Compound | n | IC$_{50}$ (µM) |
|---|---|---|
| Example 2 | 3 | 0.14 ± 0.02 |
| Example 4 | 3 | 0.28 ± 0.03 |
| Example 6 | 3 | 0.66 ± 0.20 |
|  | 1 | I$^a$ = 41.2% |
| Example 7 | 4 | 0.86 ± 0.27 |
| Example 8 | 4 | 0.63 ± 0.15 |
| Example 9 | 3 | 1.8 ± 0.7 |
| Example 10 | 4 | 1.11 ± 0.41 |
| Example 12 | 2 | 6.6 ± 1.6 |
|  | 2 | I$^a$ = 37 ± 0.7% |
| Example 13 | 4 | I$^a$ = 19.1 ± 1.7% |
| Example 14 | 3 | I$^a$ = 27.2 ± 2.4% |
|  | 1 | C$^b$ = 54% |
| Example 15 | 4 | 11.1 ± 0.4 |
| Example 16 | 4 | 2.9 ± 0.1 |
| Example 17 | 4 | 9.6 ± 5.7 |
| Example 18 | 4 | 2.1 ± 0.9 |
| Example 19 | 4 | 7.5 ± 4.5 |
| Example 20 | 4 | 8.6 ± 3.5 |
| Example 21 | 4 | 3.9 ± 1.1 |
| Example 22 | 3 | 25 ± 10.0 |
| Example 23 | 4 | 2.7 ± 0.3 |
| Example 24 | 4 | 27.1 ± 4.0 |
| Example 25 | 4 | 31 ± 4.5 |
| Example 26 | 4 | 5.2 ± 0.6 |
| Example 27 | 4 | 0.24 ± 0.03 |
| Example 28 | 4 | 2.0 ± 0.2 |
| Example 29 | 4 | I$^a$ = 38.6 ± 3.6% |
| Example 30 | 4 | 0.18 ± 0.03 |
|  | 1 | I$^a$ = 23% |
| Example 31 | 4 | 1.1 ± 0.3 |
| Example 32 | 4 | 4.35 ± 4.1 |
| Example 33 | 2 | 0.16 ± 0.01 |
| Example 34 | 4 | 1.9 ± 1.1 |
| Example 35 | 3 | 8.9 ± 3.0 |
| Example 36 | 2 | 0.29 ± 0.02 |
| Example 37 | 3 | 1.2 ± 1.1 |
| Example 38 | 2 | C$^b$ = 200% |
| Example 39 | 3 | 0.71 ± 0.50 |
| Example 40 | 2 | 0.2 ± 0.08 |
| Example 41 | 2 | I$^a$ = 41 ± 2.9% |
| Example 42 | 4 | 4.7 ± 1.2 |
| Example 43 | 4 | 1.1 ± 0.1 |
| Example 44 | 2 | 0.26 ± 0.015 |
| Example 45 | 4 | I$^a$ = 25 ± 2.04% |
| Example 46 | 4 | 6.1 ± 3.8 |
| Example 47 | 3 | 16.7 ± 6.2 |
| Example 48 | 3 | 0.27 ± 0.08 |
| Example 49 | 2 | 1.0 ± 0.60 |
| Example 50 | 2 | 0.105 ± 0.005 |
| Example 51 | 1 | 5.6 |
|  | 1 | I$^a$ = 44% |
|  | 3 | C$^b$ = 22 ± 3.2% |
| Example 52 | 4 | 5.9 ± 1.8 |
| Example 53 | 2 | 0.83 ± 0.66 |
| Example 54 | 1 | 17.8 |
|  |  | I$^a$ = 46% |
| Example 55 | 4 | 1.5 ± 0.4 |
| Example 56 | 4 | 0.95 ± 0.75 |
| Example 57 | 3 | I$^a$ = 29.3 ± 2.3% |
|  | 1 | C$^b$ = 160% |
| Example 58 | 6 | 2.3 ± 0.24 |
|  | 1 | I$^a$ = 25% |
| Example 59 | 3 | 1.8 ± 0.6 |
| Example 60 | 4 | 1.4 ± 0.4 |
| Example 61 | 3 | 1.7 ± 1.0 |
| Example 62 | 2 | 0.22 ± 0.04 |
| Example 63 | 3 | 1.5 ± 1.0 |
| Example 64 | 5 | 4.9 ± 2.7 |
| Example 65 | 2 | 0.85 ± 0.41 |
| Example 66 | 2 | 0.98 ± 0.40 |
| Example 67 | 3 | 5.3 ± 1.2 |
|  | 1 | I$^a$ = 47.7% |
| Example 68 | 5 | 2.2 ± 0.8 |
| Example 69 | 3 | 5.4 ± 2.1 |
| Example 70 | 2 | 1.6 ± 0.77 |
| Example 71 | 4 | 2.6 ± 0.4 |
| Example 72 | 5 | 6.5 ± 3.6 |
| Example 73 | 2 | 23.5 ± 8.1 |
|  | 2 | I$^a$ = 35.8 ± 4.9% |
| Example 74 | 2 | 0.75 ± 0.45 |
| Example 75 | 2 | 1.59 ± 0.27 |
| Example 76 | 4 | 0.06 ± 0.014$^c$ |
| Example 77 | 3 | 2.2 ± 0.95 |
|  | 1 | I$^a$ = 25% |
| Example 78 | 3 | 2.8 ± 1.3 |
|  | 2 | I$^a$ = 18.0 ± 6.5% |
|  | 2 | C$^b$ = 28.5 ± 8.7% |
| Example 79 | 3 | 0.53 ± 0.23 |
| Example 80 | 2 | 5.0 ± 3.5 |
| Example 81 | 3 | 0.31 ± 0.08 |
| Example 82 | 2 | 0.68 ± 0.24 |
| Example 83 | 2 | 0.81 ± 0.32 |
| Example 84 | 2 | 1.6 ± 0.18 |
| Example 85 | 2 | I$^a$ = 35.1 ± 4.4% |
| Example 86 | 4 | 5.1 ± 0.96 |
| Example 87 | 2 | I$^a$ = 13.6 ± 8.4% |
| Example 88 | 4 | 7.3 ± 6.0 |
| Example 89 | 2 | 2.3 ± 0.85 |
| Example 90 | 4 | I$^a$ = 16.6 ± 3.6% |
| Example 91 | 4 | I$^a$ = 30.7 ± 6.7% |
| Example 93 | 3 | 8.1 ± 2 |
|  | 1 | I$^a$ = 44% |
| Example 94 | 6 | 1.91 ± 0.84 |
| Example 95 | 2 | 1.5 ± 0.3 |
| Example 96 | 2 | 1.3 ± 0.3 |
| Example 97 | 2 | 0.28 ± 0.025 |
| Example 98 | 4 | 20.3 ± 0.79 |
| Example 99 | 4 | 0.79 ± 0.47 |
| Example 100 | 2 | 1.24 ± 0.17 |
| Example 101 | 2 | 2.36 ± 1.6 |

$^a$Percent inhibition at 30 µM
$^b$Percent contraction at 30 µM
$^c$A second lot (mp 215.5–216.0° C. (softens 211.5° C.)) exhibited an IC$_{50}$ = 0.13 ± 0.03 µM (n = 6).

In addition, we tested the ability of compounds to inhibit the hyperactivity of hypertrophied bladder (detrussor) smooth muscle in conscious female rats with hypertrophied bladders and thereby alleviate urinary incontinence in rats according to the following protocol described by Malmgren (A. Malmgren, K. E. Andersson, C. Sjogren, P. O. Andersson, Effects of pinacidil and Cromakalim (BRL 34915) on Bladder Function in Rats with Detrusor Instability, J. Urol. 142: 1134, 1989.):

Female Sprague-Dawley rats, ranging in weight from 190–210 g are used. Up to 25 animals are prepared each time. After developemnt of bladder hypertrophy 4–8 animals are used per test.

Compounds are dissolved in PEG-200 and administered by gastric gavage or intraveneously in a volume of 5 ml/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4–0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals ar allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations. The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 min t rest before the saline infusion (20 ml/hr for 20 minutes) is started for the first cystometry period. Two hours after the first cystometry period, the rats are dosed with the vehicle or the test compound and one hour later a second cystometry is performed.

The following urodynamic variables are recorded:

Basal bladder pressure=the lowest bladder pressure during cystometry

Threshold pressure=bladder pressure immediately prior to micturition

Micturition volume=volume expelled

Micturition pressure=peak pressure during voiding

Spontaneous activity=mean amplitude of bladder pressure fluctuations during filling Presentation of results: The mean value of each variable is calculated before and after compound administration. For each compound the changes in the variables measured are compared to the values obtained before treatment and expressed as percent inhibition. The data are also subjected to 2-way analysis of variance to determine significant ($p<0.05$) changes in the variable measured.

Criteria for Activity: The most characteristic finding in this rat model is spontaneous bladder contractions which develop during filling. The compounds which inhibit spontaneous contractions by at least 50% at 10 mg/kg p.o. or i.v. (arbitrary chosen dose) are considered active.

The results of this study are shown in Table II.

TABLE II

Inhibition of Spontaneous Contractions In Vivo

| Compound | # of animals | dose mg/kg (p.o.) | % Red (F)[d] |
|---|---|---|---|
| Example 2 | 6 | 1 mg/kg | −34 ± 11[e] |
|  | 6 | 3 mg/kg | −49 ± 8[e] |
|  | 4 | 10 mg/kg | −93 ± 3[e] |
| Example 6 | 4 | 3 mg/kg | −51 ± 6 |
|  | 3 | 10 mg/kg | −71 ± 3 |
| Example 8 | 3 | 3 mg/kg | −38 ± 7 |
| Example 27 | 4 | 10 mg/kg | −20 ± 22 |
| Example 30 | 3 | 3 mg/kg | −68 ± 10 |
| Example 31 | 4 | 10 mg/kg | −38 ± 13 |
| Example 36 | 4 | 3 mg/kg | −83 ± 9 |
| Example 76 | 3 | 3 mg/kg | −57 ± 12 |

[d]Percent reduction in the total number of spontaneous contractions in the hypertrophied rat bladder model
[e]Determined on a prior lot of this compound (mp 234–236° C. (softens 225° C.)) exhibiting an $IC_{50} = 0.57 \pm 0.34 \mu M$ (n = 4)

Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally parenterally, or by aspiration to a patient in need thereof.

What is claimed is:

1. A compound of the formula

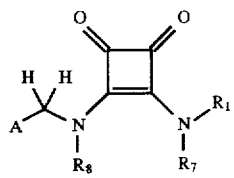

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_7$ and $R_8$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_8$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_7$ must be hydrogen;

A is a phenyl group with either two or three substituents of the following formula:

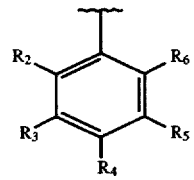

wherein:

the positions of substitution are $R_2,R_3$-, $R_2,R_4$-, $R_2,R_5$-, $R_2,R_6$-, $R_3,R_4$-, $R_3,R_5$-, and $R_2,R_4,R_6$- and $R_2$ is methyl, ethyl, fluoro, chloro, methoxy or trifluoromethyl;

$R_3$ is methyl, ethyl, fluoro, chloro, methoxy or trifluoromethyl;

$R_4$ is methyl, fluoro, bromo, methoxy or cyano;

$R_5$ is methyl, fluoro, chloro, methoxy, cyano or trifluoromethyl;

$R_6$ is methyl, fluoro, chloro, or methoxy; or a pharmaceutically acceptable salt thereof.

2. A compound of claim 1 of the formula:

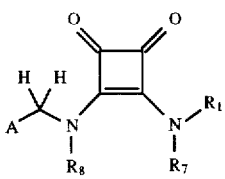
(I)

wherein
$R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a phenyl group with either two or three substituents of the following formula:

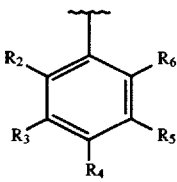

wherein:
the positions of substitution are $R_2,R_3$-, $R_2$-, $R_4$-, $R_2,R_5$-, $R_2,R_6$-, $R_3,R_4$-, $R_3,R_5$-, and $R_2,R_4,R_6$-positions and
$R_2$ is methyl, ethyl or chloro;
$R_3$ is methyl, ethyl or chloro;
$R_4$ is methyl, bromo or cyano;
$R_5$ is cyano, chloro, or methyl;
$R_6$ is methyl or choro; or a pharmaceutically acceptable salt thereof.

3. A compound of claim 1 of the formula:

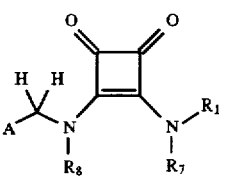
(I)

wherein
$R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

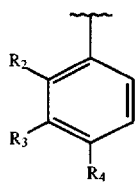

where the substitutional variations are at position combinations $R_2,R_4$- or $R_3,R_4$- and
$R_2$ is trifluoromethyl, fluoro or chloro;
$R_3$ is fluoro or chloro;
$R_4$ is fluoro; or a pharmaceutically acceptable salt thereof.

4. A compound of claim 1 of the formula:

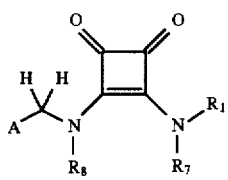
(I)

wherein
$R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

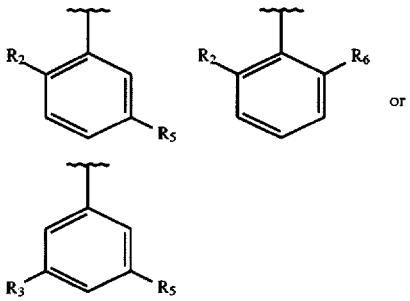

where the substitutional variations are at position combinations $R_2,R_5$-, $R_2,R_6$- or $R_3,R_5$- and
$R_2$ is methyl, fluoro or chloro;
$R_3$ is fluoro;
$R_5$ is fluoro or trifluoromethyl;

$R_6$ is fluoro; or a pharmaceutically acceptable salt thereof.

5. A compound of claim 1 of the formula:

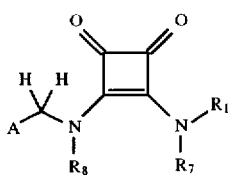

(I)

where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_2,R_3$-, $R_2,R_4$- or $R_2,R_4,R_6$-:

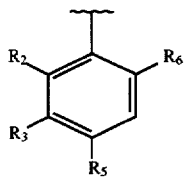

where $R_2$ is methyl, ethyl or chloro;

$R_3$ is methyl or chloro;

$R_4$ is methyl, bromo or cyano;

$R_6$ is methyl or chloro; or a pharmaceutically acceptable salt thereof.

6. A compound of claim 1 of the formula:

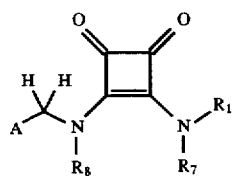

(I)

where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_3,R_4$-, $R_3,R_5$-, $R_2,R_5$-, or $R_2,R_6$-:

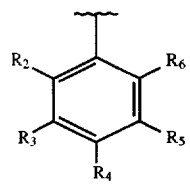

where $R_2$ is methyl or chloro;

$R_3$ is methyl, ethyl or chloro;

$R_4$ is cyano or methyl;

$R_5$ is cyano, chloro, or methyl;

$R_6$ is methyl or chloro; or a pharmaceutically acceptable salt thereof.

7. A compound of claim 1 which is 4-{|3,4-dioxo-2-(1,2,2-trimethyl-propylamino)-cyclobut-1-enylamino|-methyl}-3-methoxy-benzonitrile or a pharmaceutically acceptable salt thereof.

8. A compound of claim 2 which is 4-|(2-tert-butylamino-3,4-dioxo-cyclobut-1 -enylamino)-methyl|-3-chloro-benzonitrile or a pharmaceutically acceptable salt thereof.

9. A compound of claim 2 which is 3-(2,6-dichloro-benzylamino)-4-(1,1-dimethyl-propylamino)-cyclobut-3-ene-1,2-dione or a pharmaceutically acceptable salt thereof.

10. A compound of claim 2 which is 3-chloro-4-{|3,4-dioxo-2-(1,2,2-trimethylpropylamino)-cyclobut-1-enylamino|-methyl)-benzonitrile or a pharmaceutically acceptable salt thereof.

11. A compound of claim 2 which is 3-{|2-(1,1-dimethyl-propylamino)-3,4-dioxocyclobut-1-enylamino|-methyl}-5-methyl-benzonitrile or a pharmaceutically acceptable salt thereof.

12. A compound of claim 2 which is 3-tert-butylamino-4-(2,4-dimethyl-benzylamino)-cyclobut-3-ene-1,2-dione or a pharmaceutically acceptable salt thereof.

13. A compound of claim 2 which is 4-|(2-tert-butylamino-3,4-dioxo-cyclobut-1-enylamino)-methyl|-3-ethyl-benzonitrile or a pharmaceutically acceptable salt thereof.

14. A compound of claim 2 which is (R)-3-chloro-4-{|3,4-dioxo-2-(1,2,2-trimethyl-propylamino)-cyclobut-1-enylamino|-methyl}-benzonitrile or a pharmaceutically acceptable salt thereof.

15. A compound of claim 2 which is 3-chloro-4-{|2-(1,1-dimethyl-propylamino)-3,4-dioxo-cyclobut-1-enylamino|-methyl}-5-methyl-benzonitrile or a pharmaceutically acceptable salt thereof.

16. A compound of claim 2 which is 3-(4-bromo-2,6-dimethyl-benzylamino)-4-tert-butylamino-cyclobut-3-ene-1,2-dione or a pharmaceutically acceptable salt thereof.

17. A compound of claim 2 which is 3-tert-butylamino-4-(2-chloro-4,6-dimethyl-benzylamino)-cyclobut-3-ene-1,2-dione or a pharmaceutically acceptable salt thereof.

18. A compound of claim 2 which is 3-(2-chloro-4,6-dimethyl-benzylamino)-4-(1,1-dimethyl-propylamino)-cyclobut-3-ene-1,2-dione or a pharmaceutically acceptable salt thereof.

19. A compound of claim 2 which is 2-chloro-4-{|2-(1,1-dimethyl-propylamino|-3,4-dioxo-cyclobut-1-enylamino)-methyl}-benzonitrile or a pharmaceutically acceptable salt thereof.

20. A compound of claim 2 which is 3-(4-bromo-2-ethyl-benzylamino)-4-tert-butylamino-cyclobut-3-ene-1,2-dione or a pharmaceutically acceptable salt thereof.

21. A compound of claim 2 which is 4-|(1,1-dimethyl-propylamino-3,4-dioxo-cyclobut-1-enylamino)-methyl|-3-ethyl-benzonitrile or a pharmaceutically acceptable salt thereof.

22. A compound of claim 2 which is 3-(2,6-dimethyl-benzylamino)-4-(1,1-dimethyl-propylamino)-cyclobut-3-ene-1,2-dione or a pharmaceutically acceptable salt thereof.

23. A compound of claim 2 which is 3-chloro-4-{|2-(1,1-dimethyl-propylamino)-3,4-dioxo-cyclobut-1-enylamino|-methyl}-benzonitrile or a pharmaceutically acceptable salt thereof.

24. A compound of claim 2 which is 3-(2,4-dimethyl-benzylamino)-4-(1,1-dimethyl-propylamino)-cyclobut-3-ene-1,2-dione or a pharmaceutically acceptable salt thereof.

25. A compound of claim 2 which is 3-(1,1-dimethyl-propylamino)-4-(2,4,6-trimethyl-benzylamino)-cyclobut-3-ene-1,2-dione or a pharmaceutically acceptable salt thereof.

26. A compound of claim 2 which is 3-tert-butylamino-4-(2,5-dichloro-benzylamino)-cyclobut-3-ene-1,2-dione or a pharmaceutically acceptable salt thereof.

27. A compound of claim 2 which is 3-(2,5-dichloro-benzylamino)-4-(1,1-dimethyl-propylamino)-cyclobut-3-ene-1,2-dione or a pharmaceutically acceptable salt thereof.

28. A compound of claim 2 which is 3-(3-chloro-2-methyl-benzylamino)-4-(1,1-dimethyl-propylamino)-cyclobut-3-ene-1,2-dione or a pharmaceutically acceptable salt thereof.

29. A compound of claim 3 which is 3-(2,4-difluoro-benzylamino)-4-(1,1-dimethyl-propylamino)-cyclobut-3-ene-1,2-dione or a pharmaceutically acceptable salt thereof.

30. A compound of claim 4 which is 3-(2-chloro-5-fluoro-benzylamino)-4-(1,2,2-trimethyl-propylamino)-cyclobut-3-ene-1,2-dione or a pharmaceutically acceptable salt thereof.

31. A compound of claim 4 which is 3-(2,5-difluoro-benzylamino)-4-(1,2,2-trimethyl-propylamino)-cyclobut-3-ene-1,2-dione or a pharmaceutically acceptable salt thereof.

32. A compound of claim 4 which is 3-(3,5-difluoro-benzylamino)-4-(1,1-dimethyl-propylamino)-cyclobut-3-ene-1,2-dione or a pharmaceutically acceptable salt thereof.

33. A compound of claim 1 which is:

4-|(2-tert-butylamino-3,4-dioxo-cyclobut-1-enylamino)-methyl|-3-chloro-benzonitrile;

3-(2,6-dichloro-benzylamino)-4-(1,1-dimethyl-propylamino)-cyclobut-3-ene-1,2-dione;

3-chloro-4-{|3,4-dioxo-2-(1,2,2-trimethylpropylamino)-cyclobut-1-enylamino|-methyl}-benzonitrile;

3-{|2-(1,1-dimethyl-propylamino)-3,4-dioxo-cyclobut-1-enylamino|-methyl}-5-methyl-benzonitrile;

3-tert-butylamino-4-(2,4-dimethyl-benzylamino)-cyclobut-3-ene-1,2-dione;

3-tert-butylamino-4-(2,4,6-trimethyl-benzylamino)-cyclobut-3-ene-1,2-dione;

3-tert-butylamino-4-(2,6-dichloro-benzylamino)-cyclobut-3-ene-1,2-dione;

3-{|3,4-dioxo-2-(1,2,2-trimethyl-propylamino)-cyclobut-1-enylamino|-methyl}-5-methyl-benzonitrile;

3-{|2-(1-ethyl-propylamino)-3,4-dioxo-cyclobut-1-enylamino|-methyl}-5-methyl-benzonitrile;

3-(3,4-dimethoxy-benzylamino)-4-(1-ethyl-propylamino)-cyclobut-3-ene-1,2-dione;

3-tert-butylamino-4-(2,4,6-trimethoxy-benzylamino)-cyclobut-3-ene-1,2-dione;

3-|(2-tert-butylamino-3,4-dioxo-cyclobut-1-enylamino)-methyl|-5-methyl-benzonitrile;

3-tert-butylamino-4-(2,4-dimethoxy-benzylamino)-cyclobut-3-ene-1,2-dione;

3-tert-butylamino-4-(2,4-difluoro-benzylamino)-cyclobut-3-ene-1,2-dione;

3-tert-butylamino-4-(2,6-difluoro-benzylamino)-cyclobut-3-ene-1,2-dione;

3-tert-butylamino-4-(2,3-dimethoxy-benzylamino)-cyclobut-3-ene-1,2-dione;

3-tert-butylamino-4-(2,5-difluoro-benzylamino)-cyclobut-3-ene-1,2-dione;

3-tert-butylamino-4-(3,5-dimethoxy-benzylamino)-cyclobut-3-ene-1,2-dione;

3-tert-butylamino-4-(2,3-dimethyl-benzylamino)-cyclobut-3-ene-1,2-dione;

4-|(2-butylamino-3,4-dioxo-cyclobut-1-enylamino)-methyl|-3-ethyl-benzonitrile;

3-ethyl-4-|(2-isopropylamino-3,4-dioxo-cyclobut-1-enylamino)-methyl-benzonitrile;

3-ethyl-4-{|(2-(1-ethyl-propylamino)-3,4-dioxo-cyclobut-1-enylamino|-methyl}-benzonitrile;

4-|(2-tert-butylamino-3,4-dioxo-cyclobut-1-enylamino)-methyl|-3-ethyl-benzonitrile;

4-{|3,4-dioxo-2-(1,2,2-trimethyl-propylamino)-cyclobut-1-enylamino|-methyl}-3-ethyl-benzonitrile;

3-(2-chloro-6-methyl-benzylamino)-4-(1,2,2-trimethyl-propylamino)-cyclobut-3-ene-1,2-dione;

(R)-3-chloro-4-{|3,4-dioxo-2-(1,2,2-trimethyl-propylamino)-cyclobut-1-enylamino|-methyl}-benzonitrile;

3-tert-butylamino-4-(2-chloro-6-methyl-benzylamino)-cyclobut-3-ene-1,2-dione;

3-(2-chloro-6-methyl-benzylamino)-4-(1,1-dimethyl-propylamino)-cyclobut-3-ene-1,2-dione;

3-chloro-4-{|2-(1,1-dimethyl-propylamino)-3,4-dioxo-cyclobut-1-enylamino|-methyl}-5-methyl-benzonitrile;

3-chloro-4-(|3,4-dioxo-2-(1,2,2-trimethyl-propylamino)-cyclobut-1-enylamino|-methyl}-5-methyl-benzonitrile;

3-(4-bromo-2,6-dimethyl-benzylamino)-4-(1,2,2-trimethyl-propylamino)-cyclobut-3-ene-1,2-dione;

3-(4-bromo-2,6-dimethyl-benzylamino)-4-tert-butylamino-cyclobut-3-ene-1,2-dione;

3-(4-bromo-2,6-dimethyl-benzylamino)-4-(1,1-dimethyl-propylamino)-cyclobut-3-ene-1,2-dione;

3-(2-chloro-4,6-dimethyl-benzylamino)-4-(1,2,2-trimethyl-propylamino)-cyclobut-3-ene-1,2-dione;

3-tert-butylamino-4-(2-chloro-4,6-dimethyl-benzylamino)-cyclobut-3-ene-1,2-dione;

3-(2-chloro-4,6-dimethyl-benzylamino)-4-(1,1-dimethyl-propylamino)-cyclobut-3-ene-1,2-dione;

3-(2-chloro-4,6-dimethyl-benzylamino)-4-(2,2,3,3,3-pentafluoro-propylamino)-cyclobut-3-ene-1,2-dione;

2-chloro-4-(|3,4-dioxo-2-(1,2,2-trimethyl-propylamino)-cyclobut-1-enylamino|-methyl)-benzonitrile;

4-|(2-tert-butylamino-3,4-dioxo-cyclobut-1-enylamino)-methyl|-2-chloro-benzonitrile;

2-chloro-4-{|2-(1,1-dimethyl-propylamino)-3,4-dioxo-cyclobut-1-enylamino|-methyl}-benzonitrile;

4-{|3,4-dioxo-2-(1,2,2-trimethyl-propylamino)-cyclobut-1-enylamino|-methyl}-2-ethyl-benzonitrile;

4-|(2-tert-butylamino-3,4-dioxo-cyclobut-1-enylamino)-methyl|-2-ethyl-benzonitrile;

3-(4-bromo-2-ethyl-benzylamino)-4-(1,2,2-trimethyl-propylamino)-cyclobut-3-ene-1,2-dione;

3-(4-bromo-2-ethyl-benzylamino)-4-tert-butylamino-cyclobut-3-ene-1,2-dione;

3-(4-bromo-2-ethyl-benzylamino)-4-(1,1-dimethyl-propylamino)-cyclobut-3-ene-1,2-dione;

4-{(1,1-dimethyl-propylamino-3,4-dioxo-cyclobut-1-enylamino)-methyl]-3-ethyl-benzonitrile;

3-(2,6-dimethyl-benzylamino)-4-(1,2,2-trimethyl-propylamino)-cyclobut-3-ene-1,2-dione;

3-tert-butylamino-4-(2,6-dimethyl-benzylamino)-cyclobut-3-ene-1,2-dione;

3-(2,6-dimethyl-benzylamino)-4-(1,1-dimethyl-propylamino)-cyclobut-3-ene-1,2-dione;

3-(2,6-dimethyl-benzylamino)-4-(2,2,3,3,3-pentafluoro-propylamino)-cyclobut-3-ene-1,2-dione;

4-{|3,4-dioxo-2-(1,2,2-trimethyl-propylamino)-cyclobut-1-enylamino|-methyl}-3-methyl-benzonitrile;

4-{|3,4-dioxo-2-(1,2,2-trimethyl-propylamino)-cyclobut-1 -enylamino|-methyl}-3-methoxy-benzonitrile;

3-(2-methoxy-6-methyl-benzylamino)-4-(1,2,2-trimethyl-propylamino)-cyclobut-3-ene-1,2-dione;

3-tert-butylamino-4-(2-ethyl-6-methyl-benzylamino)-cyclobut-3-ene-1,2-dione;

3-tert-butylamino-4-(4-fluoro-2-trifluoromethyl-benzylamino)-cyclobut-3-ene-1,2-dione;

3-tert-butylamino-4-(2-chloro-4-fluoro-benzylamino)-cyclobut-3-ene-1,2-dione;

3-(4-fluoro-2-trifluoromethyl-benzylamino)-4( 1,2,2-trimethyl-propylamino)-cyclobut-3-ene-1,2-dione;

3-(2,4-difluoro-benzylamino)-4-(1,1-dimethyl-propylamino)-cyclobut-3-ene-1,2-dione;

3-(2-chloro-4-fluoro-benzylamino)-4-(1,1-dimethyl-propylamino)-cyclobut-3-ene-1,2-dione;

3-tert-butylamino-4-(2-fluoro-5-trifluoromethyl-benzylamino)-cyclobut-3-ene-1,2-dione;

3-(2-chloro-5-fluoro-benzylamino)-4-(1,2,2-trimethyl-propylamino)-cyclobut-3-ene-1,2-dione;

3-(2,5-difluoro-benzylamino)-4-(1,2,2-trimethyl-propylamino)-cyclobut-3-ene-1,2-dione;

3-tert-butylamino-4-(3-chloro-4-fluoro-benzylamino)-cyclobut-3-ene-1,2-dione;

3-tert-butylamino-4-(3,4-difluoro-benzylamino)-cyclobut-3-ene-1,2-dione;

3-(3-chloro-4-fluoro-benzylamino)-4-(1,2,2-trimethyl-propylamino)-cyclobut-3-ene-1,2-dione;

3-(3,4-difluoro-benzylamino)-4-(1,1-dimethyl-propylamino)-cyclobut-3-ene-1,2-dione;

3-tert-butylamino-4-(3,5-difluoro-benzylamino)-cyclobut-3-ene-1,2-dione;

3-tert-butylamino-4-(3-fluoro-5-trifluoromethyl-benzylamino)-cyclobut-3-ene-1,2-dione;

3-(3,5-bis-trifluoromethyl-benzylamino)-4-tert-butylamino-cyclobut-3-ene-1,2-dione;

3-(3,5-difluoro-benzylamino)-4-( 1,1-dimethyl-propylamino)-cyclobut-3-ene-1,2-dione;

3-chloro-4-{|2-(2-fluoro-1,2-dimethyl-propylamino)-3,4-dioxo-cyclobut-1-enylamino|-methyl}-benzonitrile;

3-chloro-4-{|2-(1,1-dimethyl-propylamino)-3,4-dioxo-cyclobut-1-enylamino|-methyl}-benzonitrile;

N-(2-chloro-4-cyano-benzyl)-N-|2-(1,1-dimethyl-propylamino)-3,4-dioxo-cyclobut-1-enyl)-acetamide;

N-(2-chloro-4-cyano-benzyl)-N-|2-(1,1-dimethyl-propylamino)-3,4-dioxo-cyclobut-1-enyl|-butylamine;

3-(2,4-dimethyl-benzylamino)-4-(1,1-dimethyl-propylamino)-cyclobut-3-ene-1,2-dione;

3-(2,3-dimethyl-benzylamino)-4-(1,1-dimethyl-propylamino)-cyclobut-3-ene-1,2-dione;

3-(1,1 -dimethyl-propylamino)-4-(2,4,6-trimethyl-benzylamino)-cyclobut-3-ene-1,2-dione;

3-tert-butylamino-4-(2,5-dichloro-benzylamino)-cyclobut-3-ene-1,2-dione;

3-(2,5-dichloro-benzylamino)-4-(1,1-dimethyl-propylamino)-cyclobut-3-ene-1,2-dione;

3-tert-butylamino-4-(3,4-dimethyl-benzylamino)-cyclobut-3-ene-1,2-dione;

3-(3,4-dimethyl-benzylamino)-4-(1,1-dimethyl-pronylamino)-cyclobut-3-ene-1,2-dione;

3-tert-butylamino-4-(3,5-dimethyl-benzylamino)-cyclobut-3-ene-1,2-dione;

3-(3,5-dimethyl-benzylamino)-4-(1,1-dimethyl-propylamino)-cyclobut-3-ene-1,2-dione;

3-(3,5-dichloro-benzylamino)-4-(1,1-dimethyl-propylamino)-cyclobut-3-ene-1,2-dione;

3-tert-butylamino-4-(3,5-dichloro-benzylamino)-cyclobut-3-ene-1,2-dione;

3-tert-butylamino-4-(3-chloro-4-methyl-benzylamino)-cyclobut-3-ene-1,2-dione;

3-(3-chloro-4-methyl-benzylamino)-4-(1,1-dimethyl-propylamino)-cyclobut-3-ene-1,2-dione;

3-chloro-4-{|2-(2-hydroxy-1,1-dimethyl-ethylamino)-3,4-dioxo-cyclobut-1-enylamino|-methyl}-benzonitrile;

3-(2,5-dimethyl-benzylamino)-4-(1,1-dimethyl-propylamino)-cyclobut-3-ene-1,2-dione;

3-tert-butylamino-4-(2,5-dimethyl-benzylamino)-cyclobut-3-ene-1,2-dione;

3-tert-butylamino-4-(3-chloro-2-methyl-benzylamino)-cyclobut-3-ene-1,2-dione;

3-(3-chloro-2-methyl-benzylamino)-4-(1,1-dimethyl-propylamino-cyclobut-3-ene-1,2-dione;

N-(2-tert-butylamino-3,4-dioxo-cyclobut-1-enyl)-N-(2-chloro-4-cyano-benzyl)-acetamide;

3-(2,3-dichloro-benzylamino)-4-(1,1-dimethyl-propylamino)-cyclobut-3-ene-1,2-dione;

3-(t-butylamino)-4-(2,3-dichloro-benzylamino)-cyclobut-3-ene-1,2-dione;

N-(2-tert-butylamino-3,4-dioxo-cyclobut-1-enyl)-N-(2-chloro-4-cyano-benzyl)-butylamine; or a pharmaceutically acceptable salt thereof.

34. A pharmaceutical composition of matter comprising a compound of the formula:

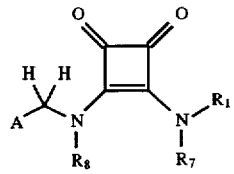

(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_7$ and $R_8$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_8$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_7$ must be hydrogen;

A is a phenyl group with either two or three substituents of the following formula:

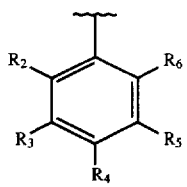

wherein:
the positions of substitution are $R_2,R_3$-, $R_2,R_4$-, $R_2,R_5$-, $R_2,R_6$-, $R_3,R_4$-, $R_3,R_5$-, and $R_2,R_4,R_6$- and $R_2$ is methyl, ethyl, fluoro, chloro, methoxy or trifluoromethyl;

$R_3$ is methyl, ethyl, fluoro, chloro, methoxy or trifluoromethyl;

$R_4$ is methyl, fluoro, bromo, methoxy or cyano;

$R_5$ is methyl, fluoro, chloro, methoxy, cyano or trifluoromethyl;

$R_6$ is methyl, fluoro, chloro, or methoxy; or a pharmaceutically acceptable salt thereof and a pharmaceutically acceptable carrier therefor; or, wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a phenyl group with either two or three substituents of the following formula:

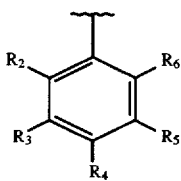

wherein:
the positions of substitution are $R_2,R_3$-, $R_2,R_4$-, $R_2,R_5$-, $R_2,R_6$-, $R_3,R_4$-, $R_3,R_5$-, and $R_2,R_4,R_6$-positions and $R_2$ is methyl, ethyl or chloro;

$R_3$ is methyl ethyl or chloro;

$R_4$ is methyl, bromo or cyano;

$R_5$ is cyano, chloro, or methyl;

$R_6$ is methyl or choro; or a pharmaceutically acceptable salt thereof; and a pharmaceutically acceptable carrier therefor; or, wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

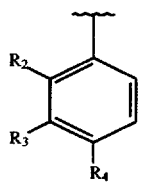

where the substitutional variations are at position combinations $R_2,R_4$- or $R_3,R_4$- and $R_2$ is trifluoromethyl, fluoro or chloro;

$R_3$ is fluoro or chloro;

$R_4$ is fluoro; or a pharmaceutically acceptable salt thereof; and a pharmaceutically acceptable carrier therefor; or wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

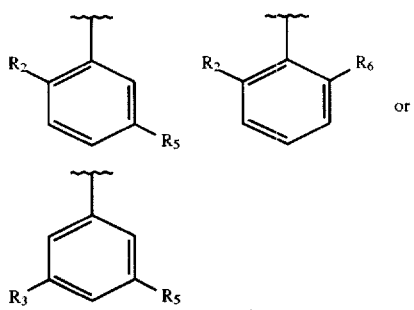

or

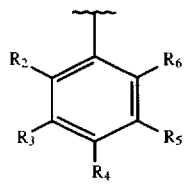

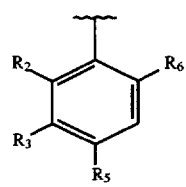

where the substitutional variations are at position combinations $R_2,R_5$-, $R_2,R_6$- or $R_3,R_5$- and $R_2$ is methyl, fluoro or chloro;

$R_3$ is fluoro;

$R_5$ is fluoro or trifluoromethyl;

$R_6$ is fluoro; or a pharmaceutically acceptable salt thereof; and a pharmaceutically acceptable carrier therefor; or where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_2,R_3$-, $R_2,R_4$- or $R_2, R_4,R_6$-:

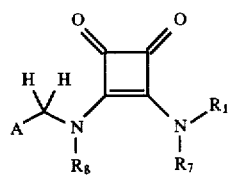

where $R_2$ is methyl, ethyl or chloro;

$R_3$ is methyl or chloro;

$R_4$ is methyl, bromo or cyano;

$R_6$ is methyl or chloro; or a pharmaceutically acceptable salt thereof and a pharmaceutically acceptable carrier therefor; or where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_3,R_4$-, $R_3,R_5$-, $R_2,R_5$-, or $R_2,R_6$-:

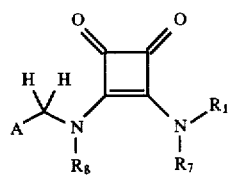

where $R_2$ is methyl or chloro;

$R_3$ is methyl, ethyl or chloro;

$R_4$ is cyano or methyl;

$R_5$ is cyano, chloro, or methyl;

$R_6$ is methyl or chloro; or a pharmaceutically acceptable salt thereof and a pharmaceutically acceptable carrier therefor.

35. A method for reducing the adverse effects of smooth muscle contractions which comprises administering, orally or parenterally, to a patient in need thereof, a compound of the formula:

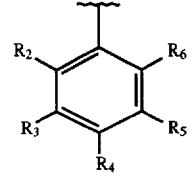
(I)

wherein:

$R_1$ is straight chain alkyl of 1 to 10 carbon atoms, branched chain alkyl of 3 to 10 carbon atoms, cycloalkyl of 3 to 10 carbon atoms, hydroxyalkyl of 2 to 10 carbon atoms, fluoroalkyl of 1 to 10 carbon atoms or polyfluoroalkyl of 1 to 10 carbon atoms;

$R_7$ and $R_8$ are, independently, hydrogen or an acyl substituent selected from the group consisting of formyl, alkanoyl of 2 to 7 carbon atoms, alkenoyl of 3 to 7 carbon atoms, straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms, aralkoxycarbonyl of 6 to 12 carbon atoms, alkylsulfonyl of 1 to 7 carbon atoms, aroyl of 7 to 12 carbon atoms, arylalkenoyl of 9 to 20 carbon atoms, arylsulfonyl of 6 to 12 carbon atoms, arylalkanoyl of 8 to 12 carbon atoms or arylalkylsulfonyl of 7 to 12 carbon atoms; with the proviso that when $R_8$ is straight chain alkoxycarbonyl of 2 to 11 carbon atoms, branched chain alkoxycarbonyl of 4 to 11 carbon atoms, cycloalkoxycarbonyl of 4 to 11 carbon atoms, alkenoxycarbonyl of 2 to 11 carbon atoms or aralkoxycarbonyl of 6 to 12 carbon atoms, $R_7$ must be hydrogen;

A is a phenyl group with either two or three substituents of the following formula:

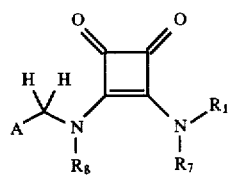

wherein:

the positions of substitution are $R_2,R_3$-, $R_2,R_4$-, $R_2,R_5$-, $R_2,R_6$-, $R_3,R_4$-, $R_3,R_5$-, and $R_2,R_4,R_6$- and $R_2$ is methyl, ethyl, fluoro, chloro, methoxy or trifluoromethyl;

$R_3$ is methyl, ethyl, fluoro, chloro, methoxy or trifluoromethyl;

$R_4$ is methyl, fluoro, bromo, methoxy or cyano;

$R_5$ is methyl, fluoro, chloro, methoxy, cyano or trifluoromethyl;

$R_6$ is methyl, fluoro, chloro, or methoxy; or a pharmaceutically acceptable salt thereof; or, wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a phenyl group with either two or three substituents of the following formula:

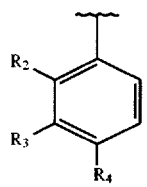

wherein:

the positions of substitution are $R_2,R_3$-, $R_2,R_4$-, $R_2,R_5$-, $R_2,R_6$-, $R_3,R_4$-, $R_3,R_5$-, and $R_2,R_4,R$-positions and $R_2$ is methyl, ethyl or chloro;

$R_3$ is methyl ethyl or chloro;

$R_4$ is methyl, bromo or cyano;

$R_5$ is cyano, chloro, or methyl;

$R_6$ is methyl or choro; or a pharmaceutically acceptable salt thereof; or, wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

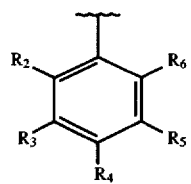

where the substitutional variations are at position combinations $R_2,R_4$- or $R_3,R_4$- and $R_2$ is trifluoromethyl, fluoro or chloro;

$R_3$ is fluoro or chloro;

$R_4$ is fluoro; or a pharmaceutically acceptable salt thereof; or wherein $R_1$ is straight chain alkyl of 1 to 10 carbon atoms, branched chain alkyl of 3 to 10 carbon atoms, fluoroalkyl of 1 to 10 carbon atoms or perfluoroalkyl of 1 to 10 carbon atoms;

$R_7$ and $R_8$ are, independently, hydrogen, alkanoyl of 2 to 7 carbon atoms, alkenoyl of 3 to 7 carbon atoms, aroyl of 7 to 12 carbon atoms, arylalkenoyl of 9 to 20 carbon atoms; straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms; with the proviso that when $R_8$ is straight chain alkoxycarbonyl of 2 to 7 carbon atoms, branched chain alkoxycarbonyl of 4 to 7 carbon atoms, alkenoxycarbonyl of 4 to 7 carbon atoms, or aralkoxycarbonyl of 6 to 12 carbon atoms, $R_7$ must be hydrogen;

A is a group of the formula:

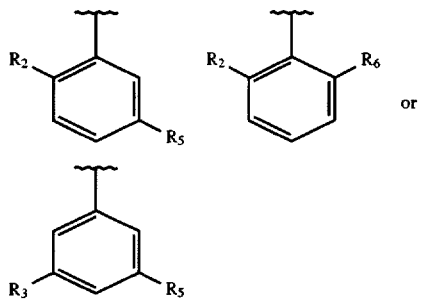

where the substitutional variations are at position combinations $R_2,R_5$-, $R_2,R_6$- or $R_3,R_5$- and $R_2$ is methyl, fluoro or chloro;

$R_3$ is fluoro;

$R_5$ is fluoro or trifluoromethyl;

$R_6$ is fluoro; or a pharmaceutically acceptable salt thereof; or where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_2,R_3$-, $R_2,R_4$- or $R_2, R_4,R_6$-:

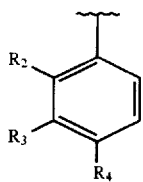

where $R_2$ is methyl, ethyl or chloro;

$R_3$ is methyl or chloro;

$R_4$ is methyl, bromo or cyano;

$R_6$ is methyl or chloro; or a pharmaceutically acceptable salt thereof; or where $R_1$ is a straight chain alkyl of 1 to 10 carbon atoms, branched chain alkyl of 3 to 10 carbon atoms or fluoroalkyl of 1 to 10 carbon atoms;

$R_7$ is hydrogen;

$R_8$ is hydrogen, alkanoyl of 2 to 7 carbon atoms or alkenoyl of 3 to 7 carbon atoms, straight chain alkoxycarbonyl of 3 or 5 carbon atoms, branched chain alkoxycarbonyl of 5 carbon atoms, alkenoxycarbonyl of 4 carbon atoms, or aralkoxycarbonyl of 8 carbon atoms;

A is a phenyl group with either two or three substituents of the following formula, in which the positions of substitution are $R_3,R_4$-, $R_3,R_5$-, $R_2,R_5$-, or $R_2,R_6$-:

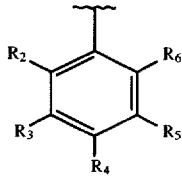

where $R_2$ is methyl or chloro;

$R_3$ is methyl, ethyl or chloro;

$R_4$ is cyano or methyl;

$R_5$ is cyano, chloro, or methyl;

$R_6$ is methyl or chloro;

or a pharmaceutically acceptable salt thereof.

* * * * *